US008383799B2

(12) United States Patent
Guo et al.

(10) Patent No.: US 8,383,799 B2
(45) Date of Patent: Feb. 26, 2013

(54) TRANSLOCATION AND MUTANT ROS KINASE IN HUMAN NON-SMALL CELL LUNG CARCINOMA

(75) Inventors: Ailan Guo, Burlington, MA (US); Anthony Possemato, Worcester, MA (US)

(73) Assignee: Cell Signaling Technology, Inc., Danvers, MA (US)

( * ) Notice: Subject to any disclaimer, the term of this patent is extended or adjusted under 35 U.S.C. 154(b) by 695 days.

(21) Appl. No.: 12/218,834

(22) Filed: Jul. 18, 2008

(65) Prior Publication Data

US 2010/0298404 A1 Nov. 25, 2010

Related U.S. Application Data

(63) Continuation of application No. PCT/US2007/001360, filed on Jan. 19, 2007, now abandoned.

(60) Provisional application No. 60/760,634, filed on Jan. 20, 2006.

(51) Int. Cl.
*C07H 21/04* (2006.01)
*C12Q 1/68* (2006.01)
*G01N 33/53* (2006.01)
*C12P 21/02* (2006.01)
*C12N 15/09* (2006.01)
*C12N 5/10* (2006.01)
*C12N 1/21* (2006.01)
*A61P 35/00* (2006.01)
*C12N 1/15* (2006.01)
*C12N 15/63* (2006.01)
*C07K 14/47* (2006.01)
*C07K 16/18* (2006.01)
*A61K 31/713* (2006.01)

(52) U.S. Cl. ............... 536/23.4; 536/23.1; 536/23.5; 435/69.1; 435/69.7; 435/320.1

(58) Field of Classification Search .................. None
See application file for complete search history.

(56) References Cited

FOREIGN PATENT DOCUMENTS

| WO | 01/00811 A2 | 1/2001 |
| WO | 2004011496 A2 | 2/2004 |
| WO | 2004/023973 A2 | 3/2004 |
| WO | 2005/076010 A2 | 8/2005 |

OTHER PUBLICATIONS

Kurzrock, R. et al., "The Molecular Genetics of Philadelphia Chromosome-Positive Leukemias" The New England Journal of Medicine (1988) pp. 990-998, vol. 319, No. 15.
Falini, B. et al., "Proteins Encoded by Genes Involved in Chromosomal Alterations in Lymphoma and Leukemia: Clinical Value of Their Detection by Immunocytochemistry" Blood (Jan. 2002) pp. 409-426, vol. 99, No. 2.
Dang, T. et al., "Cromosome 19 Translocation, Over expression of Notch3, and Human Lung Cancer" Journal of the National Cancer Institute (Aug. 16, 2000) pp. 1355-1357, vol. 92, No. 16.
Drabkin, H.A. et al., "DEF-3(g16/NT-LU-12), an RNA Binding Protein From the 3p21.3 Homozygous Deletion Region in SCLC" Oncogene (1999) pp. 2589-2597, vol. 18, No. 16.
Rangel, L.B. et al., "Characterization of Novel Human Ovarian Cancer-Specific Transcripts (HOSTs) Identified by Serial Analysis of Gene Expression" Oncogene (2003) pp. 7225-7232, vol. 22, No. 46.
Charest, A. et al., "Fusion of FIG to the Receptor Tyrosine Kinase ROS in a Glioblastoma with an Interstitial del(6) (q21Q21)" Genes Chromosomes and Cancer (May 2003) pp. 58-71, vol. 37, No. 1.
Birchmeier, C. et al., "Characterization of an Activated Human ros Gene" Molecular and Cellular Biology (Sep. 1986) pp. 3109-3116, vol. 6, No. 9.
International Search Report dated Oct. 27, 2008 issued in corresponding International Publication No. WO 2007/084631 A3.
Charest, A. et al., "Oncogenic Targeting of an Activated Tyrosine Kinase to the Golgi Apparatus in a Glioblastoma" PNAS (Feb. 4, 2003), pp. 916-921, vol. 100, No. 3.
Nagarajan, L. et al., "The Human C-ROS Gene ROS is Located at Chromosome Region 6Q16-6Q22" PNAS (1986) pp. 6568-6572, vol. 83, No. 17.
Birchmeier, C. et al., "Tyrosine Kinase Receptors in the Control of Epithelial Growth and Morphogenesis During Development" Bioessays: News and Reviews in Molecular, Cellular and Developmental Biology (Mar. 1993) pp. 185-190, vol. 15, No. 3.
Rikova, K. et al., "Global Survey of Phosphotyrosine Signaling Identifies Oncogenic Kinases in Lung Cancer" Cell (Dec. 14, 2007) pp. 1190-1203, vol. 131, No. 6.
Acquaviva, J. et al., "The Multifaceted Roles of the Receptor Tyrosine Kinase ROS in Development and Cancer" Biochimica et Biophysica ACTA—Reviews on Cancer (Jan. 2009) pp. 37-52, vol. 1795-, No. 1.
Extended European Search Report dated Jul. 13, 2010 issued in European Application No. 07718104.8.
European Office Action dated Jul. 15, 2011 issued in European Application No. 07718104.8.
Database accession No. 281 151, "S.scrofa mRNA; Expressed Sequence Tag (5'; clone c5a1 O)" Database EMBL [Online] (Oct. 23, 1996), retrieved from EBI accession No. EMBL:Z81151.
European Office Action dated Jun. 11, 2012 issued in European Application No. 07718104.8.

(Continued)

*Primary Examiner* — Robert A Zeman
(74) *Attorney, Agent, or Firm* — Scully, Scott, Murphy & Presser, P.C.

(57) ABSTRACT

In accordance with the invention, a novel gene translocation, (4p15, 6q22), in human non-small cell lung carcinoma (NSCLC) that results in a fusion proteins combining part of Sodium-dependent Phosphate Transporter Isoform NaPi-3b protein (SLC34A2) with Proto-oncogene Tyrosine Protein Kinase ROS Precursor (ROS) kinase has now been identified. The SLC34A2-ROS fusion protein is anticipated to drive the proliferation and survival of a subgroup of NSCLC tumors. The invention therefore provides, in part, isolated polynucleotides and vectors encoding the disclosed mutant ROS kinase polypeptides, probes for detecting it, isolated mutant polypeptides, recombinant polypeptides, and reagents for detecting the fusion and truncated polypeptides. The disclosed identification of the new fusion protein enables new methods for determining the presence of these mutant ROS kinase polypeptides in a biological sample, methods for screening for compounds that inhibit the proteins, and methods for inhibiting the progression of a cancer characterized by the mutant polynucleotides or polypeptides, which are also provided by the invention.

5 Claims, 16 Drawing Sheets
(4 of 16 Drawing Sheet(s) Filed in Color)

OTHER PUBLICATIONS

SSC5A10 Porcine small intestine cDNA library Sus scrofa cDNA clone c5a10 5—similar to ros proto-oncogene tyrosine kinase, mRNA sequence, GenBank Accession No. Z81151 (Oct. 24, 1996) [retrieved on Jul. 31, 2012] URL:http://www.ncbi.nlm.nih.gov/nucest/z81151.

Official Action dated Aug. 7, 2012 received from the Japanese Patent Office, issued in Japanese Patent Application No. 2008-551396, and an English translation.

Xu, H. et al., "Molecular Cloning, Functional Characterization, Tissue Distribution, and Chromosomal Localization of a Human, Small Intestinal Sodium-Phosphate (Na + -Pi) Transporter (SLC34A2)" Genomics (Dec. 1, 1999) pp. 281-284, vol. 62, No. 2.

Database accession No. AQ625138, "CITBI-EI-2650M18.TR CITBI-EI *Homo sapiens* Genomic Clone 2650M18, Genomic Survey Sequence" Database EMBL [Online] (Jun. 21, 1999), retrieved from EBI accession No. EMBL:AQ625138.

Fig. 2A

MAPWPELGDAQPNPDKYLEGAAGQQPTAPDKSKETNKTDNTEAPVTKIELLPSYSTATLIDEPTEVDDPWNLPTLQDSGI
KWSERDTKGKILCFFQGIGRLILLLGFLYFFVCSLDILSSAFQLVGAGVPNKPGIPKLLEGSKNSIQWEKAEDNGCRITY
YILEIRKSTSNNLQNQNLRWKMTFNGSCSSVCTWKSKNLKGIFQFRVVAANNLGFGEYSGISENIILVGDDFWIPETSFI
LTIIVGIFLVVTIPLTFVWHRRLKNQKSAKEGVTVLINEDKELAELRGLAAGVGLANACYAIHTLPTQEEIENLPAFPRE
KLTLRLLLGSGAFGEVYEGTAVDILGVGSGEIKVAVKTLKKGSTDQEKIEFLKEAHLMSKFNHPNILKQLGVCLLNEPQY
IILELMEGGDLLTYLRKARMATFYGPLLTLVDLVDLCVDISKGCVYLERMHFIHRDLAARNCLVSVKDYTSPRIVKIGDF
GLARDIYKNDYYRKRGEGLLPVRWMAPESLMDGIFTTQSDVWSFGILIWEILTLGHQPYPAHSNLDVLNYVQTGGRLEPP
RNCPDDLWNLMTQCWAQEPDQRPTFHRIQDQLQLFRNFFLNSIYKSRDEANNSGVINESFEGEDGDVICLNSDDIMPVAL
METKNREGLNYMVLATECGQGEEKSEGPLGSQESESCGLRKEEKEPHADKDFCQEKQVAYCPSGKPEGLNYACLTHSGYG
DGSD

*atggctccctggcctgaattgggagatgcccagcccaacccgataagtacctcgaaggggccgcaggtcagcagcccac*
*tgcccctgataaaagcaaagagaccaacaaaacagataacactgaggcacctgtaaccaagattgaacttctgccgtcct*
*actccacggctacactgatagatgagcccactgaggtggatgaccctggaacctacccactcttcaggactcggggatc*
*aagtggtcagagagagacaccaaagggaagattctctgtttcttccaagggattgggagattgattttacttctcggatt*
*tctctacttttcgtgtgctccctggatattcttagtagcgccttccagctggttggagctggagtcccaaataaaccag*
*gcattcccaaattactagaagggagtaaaaattcaatacagtgggagaaagctgaagataatggatgtagaattacatac*
*tatatccttgagataagaaagagcacttcaaataatttacagaaccagaatttaaggtggaagatgacatttaatggatc*
*ctgcagtagtgtttgcacatggaagtccaaaaacctgaaaggaatatttcagttcagagtagtagctgcaaataatctag*
*ggtttggtgaatatagtggaatcagtgagaatattatattagttggagatgattttttggataccagaaacaagtttcata*
*cttactattatagttggaatatttctggttgttacaatcccactgacctttgtctggcatagaagattaaagaatcaaaa*
*aagtgccaaggaagggtgacagtgcttataaacgaagacaaagagttggctgagctgcgaggtctggcagccggagtag*
*gcctggctaatgcctgctatgcaatacatactcttccaacccaagaggagattgaaaatcttcctgccttccctcgggaa*
*aaactgactctgcgtctcttgctgggaagtggagcctttggagaagtgtatgaaggaacagcagtggacatcttaggagt*
*tggaagtggagaaatcaaagtagcagtgaagactttgaagaagggttccacagaccaggagaagattgaattcctgaagg*
*aggcacatctgatgagcaaatttaatcatcccaacattctgaagcagcttggagtttgtctgctgaatgaacccaatac*
*attatcctggaactgatggaggaggaggagaccttcttactatttgcgtaaagcccggatggcaacgttttatggtcctt*
*actcaccttggttgaccttgtagacctgtgtgtagatatttcaaaaggctgtgtctacttggaacggatgcatttcattc*
*acagggatctggcagctagaaattgccttgtttccgtgaaagactataccagtccacggatagtgaagattggagacttt*
*ggactcgccagagacatctataaaaatgattactatagaaagagaggggaaggcctgctcccagttcggtggatggctcc*
*agaaagtttgatggatggaatcttcactactcaatctgatgtatggtcttttggaattctgatttgggagattttaactc*
*ttggtcatcagccttatccagctcattccaaccttgatgtgttaaactatgtgcaaacaggagggagactggagccacca*
*agaaattgtcctgatgatctgtggaatttaatgacccagtgctgggctcaagaacccgaccaagacctactttccatag*
*aattcaggaccaacttcagttattcagaaattttttcttaaatagcatttataagtccagagatgaagcaaacaacagtg*
*gagtcataaatgaaagctttgaaggtgaagatggcgatgtgatttgtttgaattcagatgacattatgccagttgcttta*
*atggaaacgaagaaccgagaagggttaaactatatggtacttgctacagaatgtggccaaggtgaagaaaagtctgaggg*
*tcctctaggctcccaggaatctgaatcttgtggtctgaggaagaagagaaggaaccacatgcagacaaagatttctgcc*
*aagaaaaacaagtggcttactgccttctggcaagcctgaaggcctgaactatgcctgtctcactcacagtggatatgga*
*gatgggtctgattaa*

Fig. 2B

MAPWPELGDAQPNPDKYLEGAAGQQPTAPDKSKETNKTDNTEAPVTKIELLPSYSTATLIDEPTEVDDPWNLPTLQDSGI
KWSERDTKGKILCFFQGIGRLILLLGFLYFFVCSLDILSSAFQLVGDDFWIPETSFILTIIVGIFLVVTIPLTFVWHRRL
KNQKSAKEGVTVLINEDKELAELRGLAAGVGLANACYAIHTLPTQEEIENLPAFPREKLTLRLLLGSGAFGEVYEGTAVD
ILGVGSGEIKVAVKTLKKGSTDQEKIEFLKEAHLMSKFNHPNILKQLGVCLLNEPQYIILELMEGGDLLTYLRKARMATF
YGPLLTLVDLVDLCVDISKGCVYLERMHFIHRDLAARNCLVSVKDYTSPRIVKIGDFGLARDIYKNDYYRKRGEGLLPVR
WMAPESLMDGIFTTQSDVWSFGILIWEILTLGHQPYPAHSNLDVLNYVQTGGRLEPPRNCPDDLWNLMTQCWAQEPDQRP
TFHRIQDQLQLFRNFFLNSIYKSRDEANNSGVINESFEGEDGDVICLNSDDIMPVALMETKNREGLNYMVLATECGQGEE
KSEGPLGSQESESCGLRKEEKEPHADKDFCQEKQVAYCPSGKPEGLNYACLTHSGYGDGSD atggctccctggcctgaattgggagatgcccagcccaaccccgataagtacctcgaaggggccgcaggtcagcagcccac
tgcccctgataaaagcaaagagaccaacaaaacagataacactgaggcacctgtaaccaagattgaacttctgccgtcct
actccacggctacactgatagatgagcccactgaggtggatgaccccctggaacctacccactcttcaggactcgggatc
aagtggtcagagagagacaccaaagggaagattctctgttcttccaagggattgggagattgattttacttctcggatt
tctctacttttcgtgtgctccctggatattcttagtagcgccttccagctggttggagatgattttggataccagaaa
caagtttcatacttactattatagttggaatatttctggttgttacaatcccactgacctttgtctggcatagaagatta
aagaatcaaaaaagtgccaaggaaggggtgacagtgcttataaacgaagacaaagagttggctgagctgcgaggtctggc
agccggagtaggcctggctaatgcctgctatgcaatacatactcttccaacccaagaggagattgaaaatcttcctgcct
tccctcgggaaaaactgactctgcgtctcttgctgggaagtggagcctttggagaagtgtatgaaggaacagcagtggac
atcttaggagttggaagtggagaaatcaaagtagcagtgaagactttgaagaagggttccacagaccaggagaagattga
attcctgaaggaggcacatctgatgagcaaatttaatcatccaacattctgaagcagcttggagtttgtctgctgaatg
aaccccaatacattatcctggaactgatggagggaggagaccttcttacttatttgcgtaaagcccggatggcaacgttt
tatggtcctttactcaccttggttgaccttgtagacctgtgtgtagatatttcaaaaggctgtgtctacttggaacggat
gcatttcattcacagggatctggcagctagaaattgccttgtttccgtgaaagactataccagtccacggatagtgaaga
ttggagactttggactcgccagagacatctataaaaatgattactatagaaagagaggggaaggcctgctcccagttcgg
tggatggctccagaaagtttgatggatggaatcttcactactcaatctgatgtatggtcttttggaattctgatttggga
gattttaactcttggtcatcagccttatccagctcattccaaccttgatgtgttaaactatgtgcaaacaggagggagac
tggagccaccaagaaattgtcctgatgatctgtggaatttaatgacccagtgctgggctcaagaacccgaccaaagacct
actttttcatagaattcaggaccaacttcagttattcagaaatttttttcttaaatagcatttataagtccagagatgaagc
aaacaacagtggagtcataaatgaaagctttgaaggtgaagatggcgatgtgatttgtttgaattcagatgacattatgc
cagttgctttaatggaaacgaagaaccgagaagggttaaactatatggtacttgctacagaatgtggccaaggtgaagaa
aagtctgagggtcctctaggctcccaggaatctgaatcttgtggtctgaggaaagaagagaaggaaccacatgcagacaa
agatttctgccaagaaaaacaagtggcttactgcccttctggcaagcctgaaggcctgaactatgcctgtctcactcaca
gtggatatggagatgggtctgattaa

Fig. 3

MAPWPELGDAQPNPDKYLEGAAGQQPTAPDKSKETNKTDNTEAPVTKIELLPSYSTATLI
DEPTEVDDPWNLPTLQDSGIKWSERDTKGKILCFFQGIGRLILLLGFLYFFVCSLDILSS
AFQLVGGKMAGQFFSNSSIMSNPLLGLVIGVLVTVLVQSSSTSTSIVVSMVSSSLLTVRA
AIPIIMGANIGTSITNTIVALMQVGDRSEFRRAFAGATVHDFFNWLSVLVLLPVEVATHY
LEIITQLIVESFHFKNGEDAPDLLKVITKPFTKLIVQLDKKVISQIAMNDEKAKNKSLVK
IWCKTFTNKTQINVTVPSTANCTSPSLCWTDGIQNWTMKNVTYKENIAKCQHIFVNFHLP
DLAVGTILLILSLLVLCGCLIMIVKILGSVLKGQVATVIKKTINTDFPFPFAWLTGYLAI
LVGAGMTFIVQSSSVFTSALTPLIGIGVITIERAYPLTLGSNIGTTTTAILAALASPGNA
LRSSLQIALCHFFFNISGILLWYPIPFTRLPIRMAKGLGNISAKYRWFAVFYLIIFFFLI
PLTVFGLSLAGWRVLVGVGVPVVFIIILVLCLRLLQSRCPRVLPKKLQNWNFLPLWMRSL
KPWDAVVSKFTGCFQMRCCYCCRVCCRACCLLCGCPKCCRCSKCCEDLEEAQEGQDVPVK
APETFDNITISREAQGEVPASDSKTECTAL

```
   1 cgggccaggt tccaggctc ggccgccgcc tccatcccag cacctgcgga gggagcgctg
  61 accatggctc cctggcctga attgggagat gccagccca accccgataa gtacctcgaa
 121 ggggccgcag gtcagcagcc cactgcccct gataaaagca agagaccaa caaaacagat
 181 aacactgagg cacctgtaac caagattgaa cttctgccgt cctactccac ggctacactg
 241 atagatgagc ccactgaggt ggatgacccc tggaacctac ccactcttca ggactcgggg
 301 atcaagtggt cagagagaga caccaaaggg aagattctct gtttcttcca agggattggg
 361 agattgattt tacttctcgg atttctctac tttttcgtgt gctccctgga tattcttagt
 421 agcgccttcc agctggttgg aggaaaaatg gcaggacagt tcttcagcaa cagctctatt
 481 atgtccaacc ctttgttggg gctggtgatc ggggtgctgg tgaccgtctt ggtgcagagc
 541 tccagcacct caacgtccat cgttgtcagc atggtgtcct cttcattgct cactgttcgg
 601 gctgccatcc ccattatcat ggggccaac attggaacgt caatcaccaa cactattgtt
 661 gcgctcatgc aggtgggaga tcggagtgag ttcagaagag cttttgcagg agccactgtc
 721 catgacttct tcaactggct gtccgtgttg gtgctcttgc ccgtggaggt ggccacccat
 781 tacctcgaga tcataaccca gcttatagtg gagagcttcc acttcaagaa tggagaagat
 841 gccccagatc ttctgaaagt catcactaag cccttcacaa agctcattgt ccagctggat
 901 aaaaagtta tcagccaaat tgcaatgaac gatgaaaaag cgaaaaacaa gagtcttgtc
 961 aagattttggt gcaaaacttt taccaacaag acccagatta acgtcactgt tccctcgact
1021 gctaactgca cctcccttc cctctgttgg acggatggca tccaaaactg gaccatgaag
1081 aatgtgacct acaaggagaa catcgccaaa tgccagcata tctttgtgaa tttccacctc
1141 ccggatcttg ctgtgggcac catcttgctc atactctccc tgctggtcct ctgtggttgc
1201 ctgatcatga ttgtcaagat cctgggctct gtgctcaagg ggcaggtcgc cactgtcatc
1261 aagaagacca tcaacactga tttccccttt cccttgcat ggttgactgg ctacctggcc
1321 atcctcgtcg gggcaggcat gaccttcatc gtacagagca gctctgtgtt cacgtcggcc
1381 ttgacccccc tgattggaat cggcgtgata accattgaga gggcttatcc actcacgctg
1441 ggctccaaca tcggcaccac caccaccgcc atcctggccg cttagccag ccctggcaat
1501 gcattgagga gttcactcca gatcgccctg tgccactttt tcttcaacat ctccggcatc
1561 ttgctgtggt acccgatccc gttcactcgc ctgcccatcc gcatggccaa ggggctgggc
1621 aacatctctg ccaagtatcg ctggttcgcc gtcttctacc tgatcatctt cttcttcctg
1681 atcccgctga cggtgtttgg cctctcgctg gccggctggc gggtgctggt tggtgtcggg
1741 gttcccgtcg tcttcatcat catcctggta ctgtgcctcc gactcctgca gtctcgctgc
1801 ccacgcgtcc tgccgaagaa actccagaac tggaacttcc tgccgctgtg gatgcgctcg
1861 ctgaagccct gggatgccgt cgtctccaag ttcaccggct gcttccagat gcgctgctgc
1921 tactgctgcc gcgtgtgctg ccgcgcgtgc tgcttgctgt gtggctgccc caagtgctgc
1981 cgctgcagca gtgctgcga ggacttggag gaggcgcagg agggcagga tgtccctgtc
2041 aaggctcctg agacctttga taacataacc attagcagag aggctcaggg tgaggtccct
2101 gcctcggact caaagaccga atgcacggcc ttgtaggga cgcccagat tgtcagggat
2161 gggggatgg tccttgagtt ttgcatgctc tcctccctcc cacttctgca ccctttcacc
2221 acctcgagga gatttgctcc ccattagcga atgaaattga tgcagtccta aaaaaaaaa
```

Fig. 4A

MKNIYCLIPKLVNFATLGCLWISVVQCTVLNSCLKSCVTNLGQQLDLGTPHNLSEPCIQG
CHFWNSVDQKNCALKCRESCEVGCSSAEGAYEEEVLENADLPTAPFASSIGSHNMTLRWK
SANFSGVKYIIQWKYAQLLGSWTYTKTVSRPSYVVKPLHPFTEYIFRVVWIFTAQLQLYS
PPSPSYRTHPHGVPETAPLIRNIESSSPDTVEVSWDPPQFPGGPILGYNLRLISKNQKLD
AGTQRTSFQFYSTLPNTIYRFSIAAVNEVGEGPEAESSITTSSSAVQQEEQWLFLSRKTS
LRKRSLKHLVDEAHCLRLDAIYHNITGISVDVHQQIVYFSEGTLIWAKKAANMSDVSDLR
IFYRGSGLISSISIDWLYQRMYFIMDELVCVCDLENCSNIEEITPPSISAPQKIVADSYN
GYVFYLLRDGIYRADLPVPSGRCAEAVRIVESCTLKDFAIKPQAKRIIYFNDTAQVFMST
FLDGSASHLILPRIPFADVKSFACENNDFLVTDGKVIFQQDALSFNEFIVGCDLSHIEEF
GFGNLVIFGSSSQLHPLPGRPQELSVLFGSHQALVQWKPPALAIGANVILISDIIELFEL
GPSAWQNWTYEVKVSTQDPPEVTHIFLNISGTMLNVPELQSAMKYKVSVRASSPKRPGPW
SEPSVGTTLVPASEPPFIMAVKEDGLWSKPLNSFGPGEFLSSDIGNVSDMDWYNNSLYYS
DTKGDVFVWLLNGTDISENYHLPSIAGAGALAFEWLGHFLYWAGKTYVIQRQSVLTGHTD
IVTHVKLLVNDMVVDSVGGYLYWTTLYSVESTRLNGESSLVLQTQPWFSGKKVIALTLDL
SDGLLYWLVQDSQCIHLYTAVLRGQSTGDTTITEFAAWSTSEISQNALMYYSGRLFWING
FRIITTQEIGQKTSVSVLEPARFNQFTIIQTSLKPLPGNFSFTPKVIPDSVQESSFRIEG
NASSFQILWNGPPAVDWGVVFYSVEFSAHSKFLASEQHSLPVFTVEGLEPYALFNLSVTP
YTYWGKGPKTSLSLRAPETVPSAPENPRIFILPSGKCCNKNEVVVEFRWNKPKHENGVLT
KFEIFYNISNQSITNKTCEDWIAVNVTPSVMSFQLEGMSPRCFIAFQVRAFTSKGPGPYA
DVVKSTTSEINPFPHLITLLGNKIVFLDMDQNQVVWTFSAERVISAVCYTADNEMGYYAE
GDSLFLLHLHNRSSSELFQDSLVFDITVITIDWISRHLYFALKESQNGMQVFDVDLEHKV
KYPREVKIHNRNSTIISFSVYPLLSRLYWTEVSNFGYQMFYYSIISHTLHRILQPTATNQ
QNKRNQCSCNVTEFELSGAMAIDTSNLEKPLIYFAKAQEIWAMDLEGCQCWRVITVPAML
AGKTLVSLTVDGDLIYWIITAKDSTQIYQAKKGNGAIVSQVKALRSRHILAYSSVMQPFP
DKAFLSLASDTVEPTILNATNTSLTIRLPLAKTNLTWYGITSPTPTYLVYYAEVNDRKNS
SDLKYRILEFQDSIALIEDLQPFSTYMIQIAVKNYYSDPLEHLPPGKEIWGKTKNGVPEA
VQLINTTVRSDTSLIISWRESHKPNGPKESVRYQLAISHLALIPETPLRQSEFPNGRLTL
LVTRLSGGNIYVLKVLACHSEEMWCTESHPVTVEMFNTPEKPYSLVPENTSLQFNWKAPL
NVNLIRFWVELQKWKYNEFYHVKTSCSQGPAYVCNITNLQPYTSYNVRVVVYKTGENST
SLPESFKTKAGVPNKPGIPKLLEGSKNSIQWEKAEDNGCRITYYILEIRKSTSNNLQNQN
LRWKMTFNGSCSSVCTWKSKNLKGIFQFRVVAANNLGFGEYSGISENIILVGDDFWIPET
SFILTIIVGIFLVVTIPLTFVWHRRLKNQKSAKEGVTVLINEDKELAELRGLAAGVGLAN
ACYAIHTLPTQEEIENLPAFPREKLTLRLLLGSGAFGEVYEGTAVDILGVGSGEIKVAVK
TLKKGSTDQEKIEFLKEAHLMSKFNHPNILKQLGVCLLNEPQYIILELMEGGDLLTYLRK
ARMATFYGPLLTLVDLVDLCVDISKGCVYLERMHFIHRDLAARNCLVSVKDYTSPRIVKI
GDFGLARDIYKNDYYRKRGEGLLPVRWMAPESLMDGIFTTQSDVWSFGILIWEILTLGHQ
PYPAHSNLDVLNYVQTGGRLEPPRNCPDDLWNLMTQCWAQEPDQRPTFHRIQNQLQLFRN
FFLNSIYQCRDEANNSGVINESFEGEDGDVICLNSDDIMPVVLMETKNREGLNYMVLATE
CGQGEEKSEGPLGSQESESCGLRKEEKEPHADKDFCQEKQVAYCPSGKPEGLNYACLTHS
GYGDGSD

(Bolding distinguish two different fusion proteins.)

Fig. 4B

```
   1 caagctttca agcattcaaa ggtctaaatg aaaaaggcta agtattattt caaaaggcaa
  61 gtatatccta atatagcaaa acaaacaaag caaaatccat cagctactcc tccaattgaa
 121 gtgatgaagc ccaaataatt catatagcaa aatggagaaa attagaccgg ccatctaaaa
 181 atctgccatt ggtgaagtga tgaagaacat ttactgtctt attccgaagc ttgtcaattt
 241 tgcaactctt ggctgcctat ggatttctgt ggtgcagtgt acagttttaa atagctgcct
 301 aaagtcgtgt gtaactaatc tgggccagca gcttgacctt ggcacaccac ataatctgag
 361 tgaaccgtgt atccaaggat gtcacttttg aactctgta gatcagaaaa actgtgctttt
 421 aaagtgtcgg gagtcgtgtg aggttggctg tagcagcgcg gaaggtgcat atgaagagga
 481 agtactggaa aatgcagacc taccaactgc tcccttttgct tcttccattg gaagccacaa
 541 tatgacatta cgatggaaat ctgcaaactt ctctggagta aaatacatca ttcagtggaa
 601 atatgcacaa cttctgggaa gctggactta tactaagact gtgtccagac cgtcctatgt
 661 ggtcaagccc ctgcacccct tcactgagta catttttccga gtggtttgga tcttcacagc
 721 gcagctgcag ctctactccc ctccaagtcc cagttacagg actcatcctc atggagttcc
 781 tgaaactgca cctttgatta ggaatattga gagctcaagt ccgacactg tggaagtcag
 841 ctgggatcca cctcaattcc caggtggacc tatttgggt tataacttaa ggctgatcag
 901 caaaaatcaa aaattagatg cagggacaca gagaaccagt ttccagtttt actccacttt
 961 accaaatact atctacaggt tttctattgc agcagtaaat gaagttggtg agggtccaga
1021 agcagaatct agtattacca cttcatcttc agcagttcaa caagaggaac agtggctctt
1081 tttatccaga aaaacttctc taagaaagag atctttaaaa catttagtag atgaagcaca
1141 ttgccttcgg ttggatgcta tataccataa tattacagga atatctgttg atgtccacca
1201 gcaaattgtt tatttctctg aaggaactct catatgggcg aagaaggctg ccaacatgtc
1261 tgatgtatct gacctgagaa tttttttacag aggttcagga ttaatttctt ctatctccat
1321 agattggctt tatcaaagaa tgtatttcat catggatgaa ctggtatgtg tctgtgattt
1381 agagaactgc tcaaacatcg aggaaattac tccaccctct attagtgcac ctcaaaaaat
1441 tgtggctgat tcatacaatg ggtatgtctt ttacctcctg agagatggca tttatagagc
1501 agaccttcct gtaccatctg gccggtgtgc agaagctgtg cgtattgtgg agagttgcac
1561 gttaaaggac tttgcaatca agccacaagc caagcgaatc atttacttca atgacactgc
1621 ccaagtcttc atgtcaacat ttctggatgg ctctgcttcc catctcatcc tacctcgcat
1681 cccctttgct gatgtgaaaa gttttgcttg tgaaaacaat gactttcttg tcacagatgg
1741 caaggtcatt ttccaacagg atgctttgtc ttttaatgaa ttcatcgtgg gatgtgacct
1801 gagtcacata gaagaatttg ggtttggtaa cttggtcatc tttggctcat cctcccagct
1861 gcaccctctg ccaggccgcc cgcaggagct ttcggtgctg tttggctctc accaggctct
1921 tgttcaatgg aagcctcctg cccttgccat aggagccaat gtcatcctga tcagtgatat
1981 tattgaactc tttgaattag gcccttctgc ctggcagaac tggacctatg aggtgaaagt
2041 atccacccaa gaccctcctg aagtcactca tatttttcttg aacataagtg gaaccatgct
2101 gaatgtacct gagctgcaga gtgctatgaa atacaaggtt tctgtgagag caagttctcc
2161 aaagaggcca ggccctggt cagagccctc agtgggtact accctggtgc cagctagtga
2221 accaccattt atcatggctg tgaaagaaga tgggctttgg agtaaaccat taaatagctt
2281 tggcccagga gagttcttat cctctgatat aggaaatgtg tcagacatgg attggtataa
2341 caacagcctc tactacagtg acacgaaagg cgacgttttt gtgtggctgc tgaatgggac
2401 ggatatctca gagaattatc acctacccag cattgcagga gcaggggctt tagctttga
2461 gtggctgggt cacttttctct actgggctgg aaagacatat gtgatacaaa ggcagtctgt
2521 gttgacggga cacacagaca ttgttaccca cgtgaagcta ttggtgaatg acatggtggt
2581 ggattcagtt ggtggatatc tctactggac cacactctat tcagtggaaa gcaccagact
2641 aaatggggaa agttcccttg tactacagac acagccttgg ttttctggga aaaagtaat
2701 tgctctaact ttagacctca gtgatgggct cctgtattgg ttggtcaag acagtcaatg
2761 tattcacctg tacacagctg ttcttcgggg acagagcact ggggatacca ccatcacaga
2821 atttgcagcc tggagtactt ctgaaatttc ccagaatgca ctgatgtact atagtggtcg
2881 gctgttctgg atcaatggct ttaggattat cacaactcaa gaaataggtc agaaaaccag
2941 tgtctctgtt ttggaaccag ccagatttaa tcagttcaca attattcaga catcccttaa
3001 gcccctgcca gggaactttt ccttttacccc taaggttatt ccagattctg ttcaagagtc
3061 ttcatttagg attgaaggaa atgcttcaag ttttcaaatc ctgtggaatg gtcccctgc
3121 ggtagactgg ggtgtagttt tctacagtgt agaatttagt gctcattcta agttcttggc
3181 tagtgaacaa cactctttac ctgtatttac tgtggaagga ctggaacctt atgccttatt
3241 taatctttct gtcactcctt atacctactg gggaaagggc cccaaaacat ctctgtcact
3301 tcgagcaccct gaaacagttc catcagcacc agagaaccc agaatattta tattaccaag
3361 tggaaaatgc tgcaacaaga atgaagttgt ggtggaattt aggtggaaca aacctaagca
3421 tgaaaatggg gtgttaacaa aatttgaaat ttctacaat atatccaatc aaagtattac
3481 aaacaaaaca tgtgaagact ggattgctgt caatgtcact ccctcagtga tgtcttttca
3541 acttgaaggc atgagtccca gatgctttat tgccttccag gttagggcct ttacatctaa
3601 ggggccagga ccatatgctg acgttgtaaa gtctacaaca tcagaaatca ccccatttcc
3661 tcacctcata actcttcttg gtaacaagat agttttttta gatatggatc aaaatcaagt
3721 tgtgtggacg tttttcagcag aaagagttat cagtgccgtt tgctacacag ctgataatga
```

Fig. 4B (cont.)

```
3781 gatgggatat tatgctgaag gggactcact ctttcttctg cacttgcaca atcgctctag
3841 ctctgagctt ttccaagatt cactggtttt tgatatcaca gttattacaa ttgactggat
3901 ttcaaggcac ctctactttg cactgaaaga atcacaaaat ggaatgcaag tatttgatgt
3961 tgatcttgaa cacaaggtga aatatcccag agaggtgaag attcacaata ggaattcaac
4021 aataatttct ttttctgtat atcctctttt aagtcgcttg tattggacag aagtttccaa
4081 ttttggctac cagatgttct actacagtat tatcagtcac accttgcacc gaattctgca
4141 acccacagct acaaaccaac aaaacaaaag gaatcaatgt tcttgtaatg tgactgaatt
4201 tgagttaagt ggagcaatgg ctattgatac ctctaaccta gagaaaccat tgatatactt
4261 tgccaaagca caagagatct gggcaatgga tctggaaggc tgtcagtgtt ggagagttat
4321 cacagtacct gctatgctcg caggaaaaac ccttgttagc ttaactgtgg atggagatct
4381 tatatactgg atcatcacag caaaggacag cacacagatt tatcaggcaa agaaaggaaa
4441 tggggccatc gtttcccagg tgaaggccct aaggagtagg catatcttgg cttacagttc
4501 agttatgcag ccttttccag ataaagcgtt tctgtctcta gcttcagaca ctgtggaacc
4561 aactatactt aatgccacta acactagcct cacaatcaga ttacctctgg ccaagacaaa
4621 cctcacatgg tatggcatca ccagccctac tccaacatac ctggtttatt atgcagaagt
4681 taatgacagg aaaaacagct ctgacttgaa atatagaatt ctggaatttc aggacagtat
4741 agctcttatt gaagatttac aaccattttc aacatacatg atacagatag ctgtaaaaaa
4801 ttattattca gatcctttgg aacatttacc accaggaaaa gagatttggg gaaaaactaa
4861 aaatggagta ccagaggcag tgcagctcat taatacaact gtgcggtcag acaccagcct
4921 cattatatct tggagagaat ctcacaagcc aaatggacct aaagaatcag tccgttatca
4981 gttggcaatc tcacacctgg ccctaattcc taagacaaa ctaagacaaa gtgaatttcc
5041 aaatggaagg ctcactctcc ttgttactag actgtctggt ggaaatattt atgtgttaaa
5101 ggttcttgcc tgccactctg aggaaatgtg gtgtacagag agtcatcctg tcactgtgga
5161 aatgtttaac acaccagaga aaccttattc cttggttcca gagaacacta gtttgcaatt
5221 taattggaag gctccattga atgttaacct catcagattt tgggttgagc tacagaagtg
5281 gaaatacaat gagttttacc atgttaaaac ttcatgcagc caaggtcctg cttatgtctg
5341 taatatcaca aatctacaac cttatacttc atataatgtc agagtagtgg tggtttataa
5401 gacgggagaa aatagcacct cacttccaga aagctttaag acaaaagctg gagtcccaaa
5461 taaaccaggc attcccaaat tactagaagg agtaaaaat tcaatacagt gggagaaagc
5521 tgaagataat ggatgtagaa ttacatacta tatccttgag ataagaaaga gcacttcaaa
5581 taatttacag aaccagaatt taaggtggaa gatgacattt aatggatcct gcagtagtgt
5641 ttgcacatgg aagtccaaaa acctgaaagg aatatttcag ttcagagtag tagctgcaaa
5701 taatctaggg tttggtgaat atagtggaat cagtgagaat attatattag ttggagatga
5761 tttttggata ccagaaacaa gtttcatact tactattata gttggaatat ttctggttgt
5821 tacaatccca ctgacctttg tctggcatag aagattaaag aatcaaaaaa gtgccaagga
5881 aggggtgaca gtgcttataa acgaagacaa agagttggct gagctgcgag gtctggcagc
5941 cggagtaggc ctggctaatg cctgctatgc aatacatact cttccaaccc aagaggagat
6001 tgaaaatctt cctgccttcc ctcgggaaaa actgactctg cgtctcttgc tgggaagtgg
6061 agcctttgga gaagtgtatg aaggaacagc agtggacatc ttaggagttg gaagtggaga
6121 aatcaaagta gcagtgaaga ctttgaagaa gggttccaca gaccaggaga agattgaatt
6181 cctgaaggag gcacatctga tgagcaaatt taatcatccc aacattctga agcagcttgg
6241 agtttgtctg ctgaatgaac cccaatacat tatcctggaa ctgatggagg gaggagacct
6301 tcttacttat ttgcgtaaag cccggatggc aacgttttat ggtcctttac tcaccttggt
6361 tgacctgta gacctgtgtg tagatatttg aaaaggctgt gtctatcttgg aacggatgca
6421 tttcattcac agggatctgg cagctagaaa ttgccttgtt tccgtgaaag actataccag
6481 tccacggata gtgaagattg gagactttgg actcgccaga gacatctata aaaatgatta
6541 ctatagaaag agaggggaag gcctgctccc agttcggtgg atggctccag aaagtttgat
6601 ggatggaatc ttcactactc aatctgatgt atggtctttt ggaattctga tttgggagat
6661 tttaactctt ggtcatcagc cttatccagc tcattccaac cttgatgtgt taaactatgt
6721 gcaaacagga gggagactgg agccaccaag aaattgtcct gatgatctgt ggaatttaat
6781 gacccgttgt tgggctcaag aacccgacca aagacctact ttcataaga ttcaggacca
6841 acttcagtta ttcagaaatt ttttcttaaa tagcatttat aagtccagag atgaagcaaa
6901 caacagtgga gtcataaatg aaagctttga aggtgaagat ggcgatgtga tttgtttgaa
6961 ttcagatgac attatgccag ttgctttaat ggaaacgaag aaccgagaag ggttaaacta
7021 tatggtactt gctacagaat gtggccaagg tgaaaaaag tctgagggtc ctctaggctc
7081 ccaggaatct gaatcttgtg gtctgaggaa agaagagaag gaaccacatg cagacaaaga
7141 tttctgccaa gaaaaacaag tggcttactg cccttctggc aagcctgaag gcctgaacta
7201 tgcctgtctc actcacagtg gatatggaga tgggtctgat taatagcgtt gtttgggaaa
7261 tagagagttg agataaacac tctcattcag tagttactga aagaaaactc tgctagaatg
7321 ataaatgtca tggtggtcta taactccaaa taaacaatgc aacgttcc
```

Primers used for RACE
ROS-GSP1: ACCCTTCTCGGTTCTTCGTTTCCA
ROS-GSP2: GCAGCTCAGCCAACTCTTTGTCTT
ROS-GSP3: TGCCAGACAAAGGTCAGTGGGATT RACE was performed using Invitrogen 5' RACE System — SLC34A2/ROS (long)
— SLC34A2/ROS (short)

TRANSLOCATION AND MUTANT ROS KINASE IN HUMAN NON-SMALL CELL LUNG CARCINOMA

RELATED APPLICATIONS

This application is a continuation of PCT/US2007/001360 filed Jan. 19, 2007 (now abandoned), which itself claims priority to and the benefit of U.S. Ser. No. 60/760,634, filed Jan. 20, 2006 (now abandoned). The entire contents of PCT/US2007/001360 and U.S. Ser. No. 60/760,634 are hereby incorporated herein by reference.

FIELD OF THE INVENTION

The invention relates generally to proteins and genes involved in cancer, and to the detection, diagnosis and treatment of cancer.

BACKGROUND OF THE INVENTION

Many cancers are characterized by disruptions in cellular signaling pathways that lead to aberrant control of cellular processes, or to uncontrolled growth and proliferation of cells. These disruptions are often caused by changes in the activity of particular signaling proteins, such as kinases. Among these cancers is non-small cell lung carcinoma (NSCLC). NSCLC is the leading cause of cancer death in the United States, and accounts for about 87% of all lung cancers. There are about 151,000 new cases of NSCLC in the United States annually, and it is estimated that over 120,000 patients will die annually from the disease in the United States alone. See "Cancer Facts and Figures 2005," American Cancer Society. NSCLC, which comprises three distinct subtypes, is often only detected after it has metastasized, and thus the mortality rate is 75% within two years of diagnosis.

It is known that gene translocations resulting in kinase fusion proteins with aberrant signaling activity can directly lead to certain cancers. For example, it has been directly demonstrated that the BCR-ABL oncoprotein, a tyrosine kinase fusion protein, is the causative agent in human chronic myelogenous leukemia (CML). The BCR-ABL oncoprotein, which is found in at least 90-95% of CML cases, is generated by the translocation of gene sequences from the c-ABL protein tyrosine kinase on chromosome 9 into BCR sequences on chromosome 22, producing the so-called Philadelphia chromosome. See, e.g. Kurzock et al., *N. Engl. J. Med.* 319: 990-998 (1988). The translocation is also observed in acute lymphocytic leukemia and AML cases.

Gene translocations leading to mutant or fusion proteins implicated in a variety of other cancers have been described. For example, Falini et al., *Blood* 99(2): 409-426 (2002), review translocations known to occur in hematological cancers. To date, only a limited number of gene translocations and mutant proteins occurring in lung cancers have been described, including the t(15; 19) translocation involving Notch3. See Dang et al., *J. Natl. Can. Instit.* 92(16): 1355-1357 (2000). Defects in RNA Binding Protein-6 (RBM-6) expression and/or activity have been found in small cell and non-small cell lung carcinomas. See Drabkin et al., *Oncogene* 8(16): 2589-97 (1999). However, to date, no translocations in human NSCLC cancer that involve protein kinases have been described.

Defects in SLC34A2 expression and/or activation have been found in human ovarian cancer. See Rangel et al., *Oncogene* 22(46): 7225-7232 (2003). Similarly, defects in ROS kinase expression resulting from the FIG-ROS del(6)(q21, q21) translocation in glioblastoma have been described. See Charest et al., *Genes Chromos. Canc.* 37(1): 58-71 (2003). A truncated form of ROS kinase able to drive tumor growth in mice has also been described. See Birchmeier et al., *Mol. Cell. Bio.* 6(9): 3109-3115 (1986). To date, there are no known activating point mutations that occur in ROS kinase.

Identifying translocations and mutations in human cancers is highly desirable because it can lead to the development of new therapeutics that target such fusion or mutant proteins, and to new diagnostics for identifying patients that have such gene translocations. For example, BCR-ABL has become a target for the development of therapeutics to treat leukemia. Most recently, Gleevec® (Imatinib mesylate, STI-571), a small molecule inhibitor of the ABL kinase, has been approved for the treatment of CML. This drug is the first of a new class of anti-proliferative agents designed to interfere with the signaling pathways that drive the growth of tumor cells. The development of this drug represents a significant advance over the conventional therapies for CML and ALL, chemotherapy and radiation, which are plagued by well known side-effects and are often of limited effect since they fail to specifically target the underlying causes of the malignancies. Likewise, reagents and methods for specifically detecting BCR-ABL fusion protein in patients, in order to identify patients most likely to respond to targeted inhibitors like Gleevec®, have been described.

Accordingly, there remains a need for the identification of novel gene translocations or mutations resulting in fusion or mutant proteins implicated in the progression of human cancers, including lung cancers like NSCLC, and the development of new reagents and methods for the study and detection of such fusion proteins. Identification of such fusion proteins will, among other things, desirably enable new methods for selecting patients for targeted therapies, as well as for the screening of new drugs that inhibit such mutant/fusion proteins.

SUMMARY OF THE INVENTION

In accordance with the invention, a novel gene translocation, (4p15, 6q22), in human non-small cell lung carcinoma (NSCLC) that results in fusion proteins combining part of Sodium-Dependent Phosphate Transporter Isoform NaPi-3b protein (SLC34A2) with Proto-Oncogene Tyrosine Protein Kinase ROS precursor (ROS) kinase have now been identified. The two SLC34A2-ROS fusion proteins are expected to retain ROS tyrosine kinase activity and to drive the proliferation and survival of NSCLC in a subset of such cancers in which the fusion protein is expressed.

The invention therefore provides, in part, isolated polynucleotides and vectors encoding the disclosed mutant ROS polypeptides, probes and assays for detecting them, isolated mutant ROS polypeptides, recombinant mutant polypeptides, and reagents for detecting the mutant ROS polynucleotides and polypeptides. The disclosed identification of the new mutant ROS kinase proteins and SLC34A2 translocation enables new methods for determining the presence of mutant ROS polynucleotides or polypeptides in a biological sample, methods for screening for compounds that inhibit the mutant kinase proteins, and methods for inhibiting the progression of a cancer characterized by the expression of mutant ROS polynucleotides or polypeptides, which are also provided by the invention. The aspects and embodiments of the invention are described in more detail below.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2A—is the amino acid sequence (1 letter code) of the first (long) variant of human SLC34A2-ROS fusion protein (SEQ ID NO: 1) (top panel) with coding DNA sequence also indicated (SEQ ID NO: 2) (bottom panel); the residues of the SLC34A2 moiety are in italics, while the residues of the kinase domain of ROS are in bold.

FIG. 2B—is the amino acid sequence (1 letter code) of the second (short) variant of human SLC34A2-ROS fusion protein (SEQ ID NO: 3) (top panel) with coding DNA sequence also indicated (SEQ ID NO: 4) (bottom panel); the residues of the SLC34A2 moiety are in italics, while the residues of the kinase domain of ROS are in bold.

FIG. 3—is the amino acid sequence (1 letter code) of human SLC34A2 protein (SEQ ID NO: 5) (SwissProt Accession No. O95436) (top panel) with coding DNA sequence also indicated (SEQ ID NO: 6) (GeneBank Accession No. NM_006424) (bottom panel); the residues involved in the translocation are underlined.

FIG. 4A—is the amino acid sequence (1 letter code) of human ROS kinase (SEQ ID NO: 7) (SwissProt Accession No. P08922); the residues involved in the first (long) variant translocation are underlined, while the underlined bold residues are those involved in the second (short) variant translocation.

FIG. 4B—is the coding DNA sequence of human ROS kinase (SEQ ID NO: 8) (GeneBank Accession No. NM_002944); the residues involved in the first (long) variant translocation are underlined, while the underlined bold residues are those involved in the second (short) variant translocation.

DETAILED DESCRIPTION OF THE INVENTION

Figure 1A:
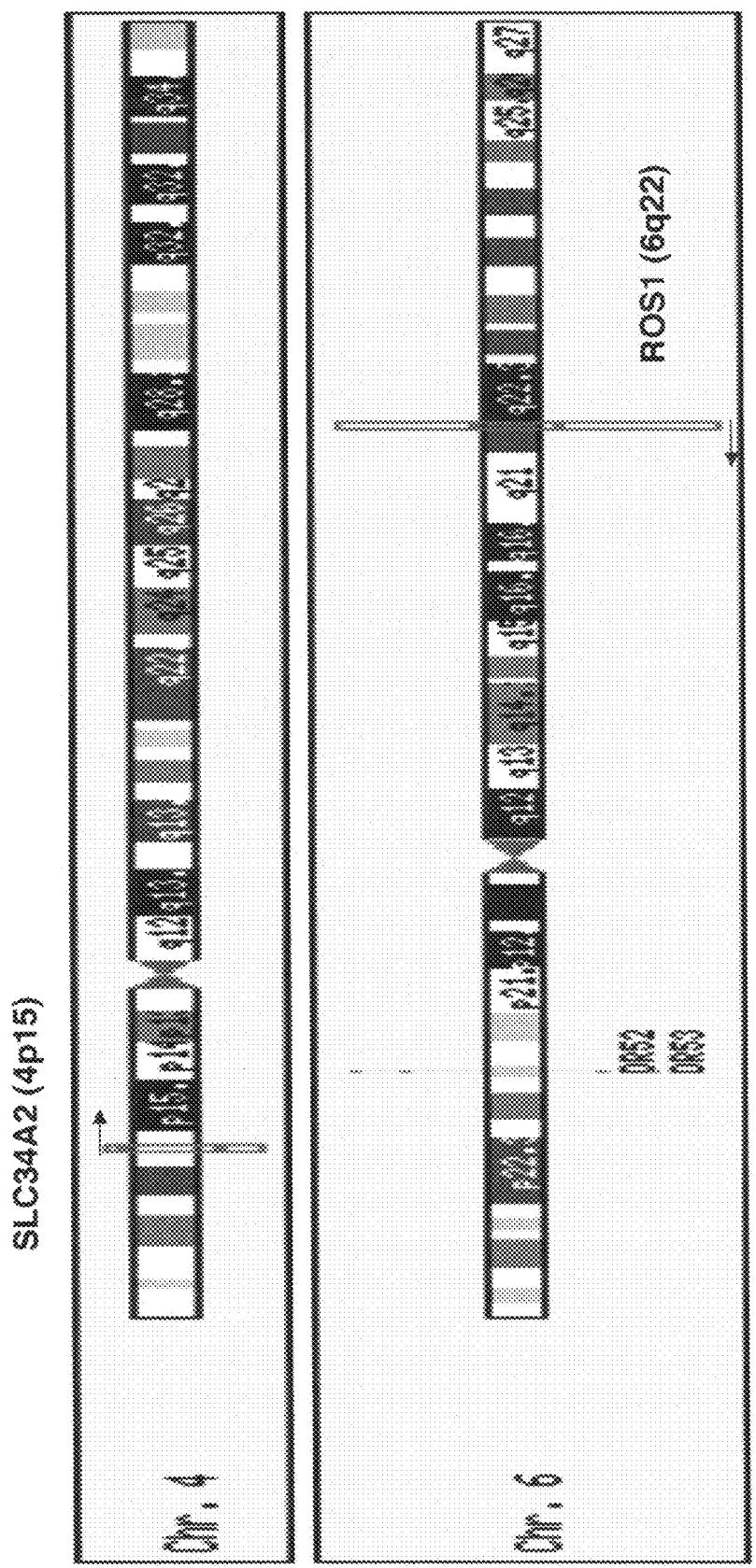
FIG. 1A—shows the location of the SLC34A2 gene and ROS gene on chromosomes 4p and 6q respectively.
Figure 1B:
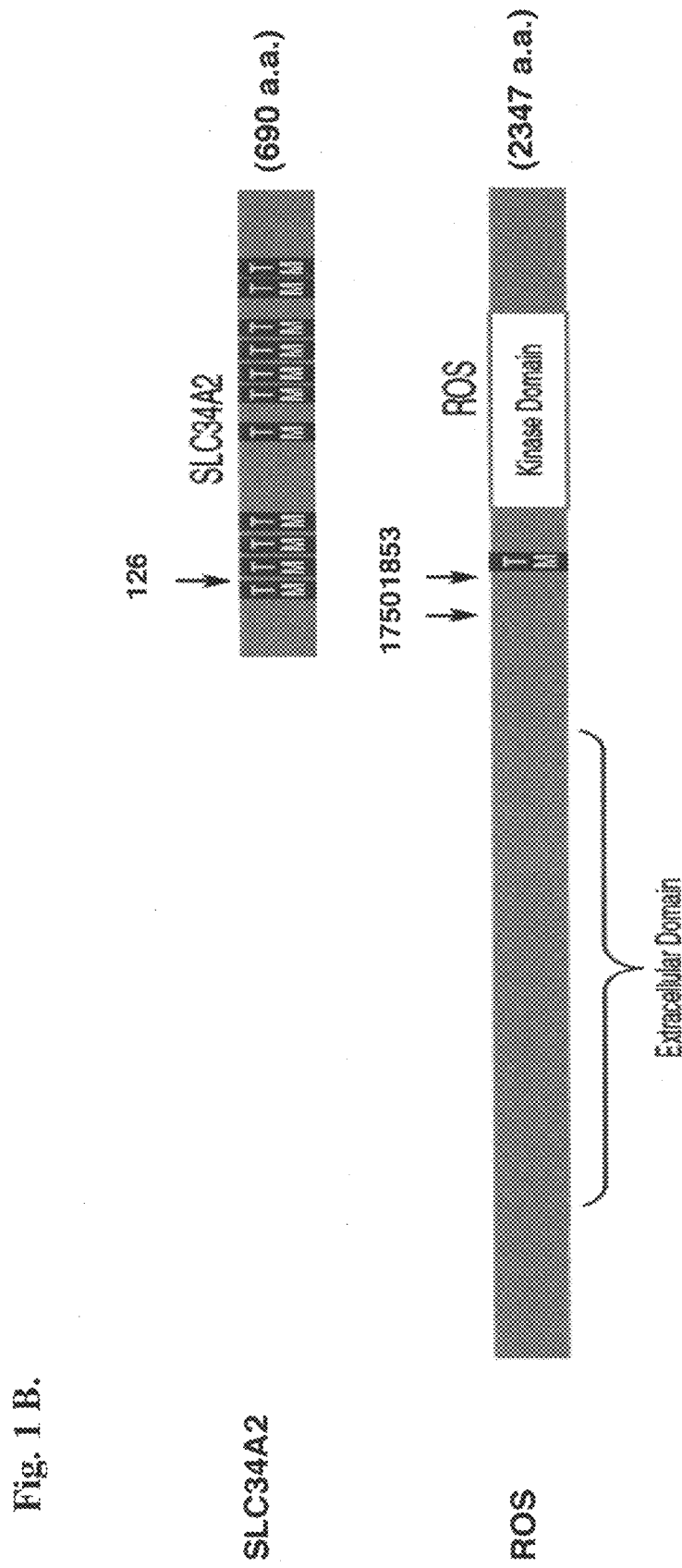
FIG. 1B—shows the domain locations of full length SLC34A2 and ROS proteins.

In accordance with the invention, a previously unknown gene translocation that results in a mutant kinase fusion protein, SLC34A2-ROS, has now been identified in human non-small cell lung carcinoma (NSCLC), a subtype of lung carcinoma. The translocation, which occurs between chromosome (4p15) and chromosome (6q22), produces two fusion protein variants that combine the N-terminus of Sodium-Dependent Phosphate Transporter Isoform NaPi-3b protein (SLC34A2), a 690 amino acid phosphate transporter protein, with the transmembrane and kinase domains of Proto-Oncogene Tyrosine Protein Kinase ROS precursor (ROS) kinase, a 2347 amino acid receptor tyrosine kinase. The resulting SLC34A2-ROS fusion proteins, which are 724 amino acids (long variant) and 621 amino acids (short variant), respectively, are expected to retain kinase activity and to drive the proliferation and survival of a subset of human NSCLC tumors in which the fusion protein is expressed.

Although a few gene translocations that result in aberrant fusion proteins involving ROS kinase have been described, including the FIG-ROS del(6)(q21,q21) translocation in glioblastoma (see Charest et al., (2003), supra.) and a truncated, active form of ROS (see Birchmeier et al., supra.), the presently disclosed SLC34A2-ROS translocation and fusion proteins are novel, and this fusion kinase is the first reported in human NSCLC. SLC34A2 is a phosphate transporter protein that is expressed in human lung and small intestine, and which has sodium-dependent activity. Defects in SLC34A2 expression and/or activity have been found in ovarian cancer. See Rangel et al., supra. ROS is a transmembrane receptor tyrosine kinase that belongs to the insulin receptor subfamily, and is involved in cell proliferation and differentiation processes. ROS is expressed, in humans, in epithelial cells of a variety of different tissues. Defects in ROS expression and/or activation have been found in glioblastoma, as well as tumors of the central nervous system. See e.g. Charest et al. (2003), supra.

As further described below, the SLC34A2-ROS translocation gene and fusion protein have presently been isolated and sequenced, and cDNAs for expressing the mutant kinase protein produced. Accordingly, the invention provides, in part, isolated polynucleotides that encode SLC34A2-ROS fusion polypeptides, nucleic acid probes that hybridize to such polynucleotides, and methods, vectors, and host cells for utilizing such polynucleotides to produce recombinant mutant ROS polypeptides. The invention also provides, in part, isolated polypeptides comprising amino acid sequences encoding SLC34A2-ROS fusion polypeptides, recombinant mutant polypeptides, and isolated reagents that specifically bind to and/or detect SLC34A2-ROS fusion polypeptides, but do not bind to or detect either wild type SLC34A2 or wild type ROS. These aspects of the invention, which are described in further detail below, will be useful, inter alia, in further studying the mechanisms of cancers driven by mutant ROS kinase expression/activity, for identifying lung carcinomas and other cancers characterized by the SLC34A2-ROS translocation and/or fusion proteins, and in practicing methods of the invention as further described below.

The identification of the novel ROS kinase mutants and translocation has important implications for the potential diagnosis and treatment of diseases, such as NSCLC, that are characterized by this translocation and/or fusion protein. NSCLC is the leading cause of cancer death in the United States, and is often difficult to diagnose until after it has metastasized, increasing the difficulty of effectively treating or curing this disease. The mortality rate of NSCLC is therefore 75% within two years of diagnosis. See American Cancer Society, supra. Although targeted EGFR-inhibitors are presently approved for the treatment of NSCLC, it is anticipated that this therapy may be partially or wholly ineffective against those patients having tumors in which mutant ROS kinase (rather than or in addition to EGFR) is expressed and driving the disease, in whole or in part.

Therefore, the present discovery of the SLC34A2-ROS fusion proteins resulting from gene translocation in NSCLC, which is expected to drive proliferation and survival in a subset of NSCLC tumors, enables important new methods for accurately identifying mammalian lung cancers (such as NSCLC), as well as other cancers, in which SLC34A2-ROS fusion protein or truncated ROS kinase is expressed. These tumors are most likely to respond to inhibitors of the kinase activity of the mutant ROS kinases. The ability to identify, as early as possible, cancers that are driven by a mutant ROS kinase will greatly assist in clinically determining which therapeutic, or combination of therapeutics, will be most appropriate for a particular patient, thus helping to avoid prescription of inhibitors targeting other kinases that are not, in fact, the primary signaling molecule driving the cancer.

Accordingly, the invention provides, in part, methods for detecting the presence of a SLC34A2-ROS translocation (t(4, 6)(p15, q22)) and/or fusion polypeptide in a cancer using fusion-specific and mutant-specific reagents of the invention. Such methods may be practiced, for example, to identify a cancer, such as a NSCLC tumor, that is likely to respond to an inhibitor of the ROS kinase activity of the mutant protein. The invention also provides, in part, methods for determining whether a compound inhibits the progression of a cancer characterized by a SLC34A2-ROS fusion polypeptide. Further provided by the invention is a method for inhibiting the progression of a cancer that expresses a SLC34A2-ROS fusion polypeptide by inhibiting the expression and/or activity of the mutant polypeptide. Such methods are described in further detail below.

The further aspects, advantages, and embodiments of the invention are described in more detail below. All references cited herein are hereby incorporated by reference in their entirety.

DEFINITIONS

As used herein, the following terms have the meanings indicated.

"Antibody" or "antibodies" refers to all types of immunoglobulins, including IgG, IgM, IgA, IgD, and IgE, including $F_{ab}$ or antigen-recognition fragments thereof, including chimeric, polyclonal, and monoclonal antibodies. The term "humanized antibody", as used herein, refers to antibody molecules in which amino acids have been replaced in the non-antigen binding regions in order to more closely resemble a human antibody, while still retaining the original binding ability.

The term "biologically active" refers to a protein having structural, regulatory, or biochemical functions of a naturally occurring molecule. Likewise, "immunologically active" refers to the capability of the natural, recombinant, or synthetic SLC34A2-ROS fusion polypeptide or truncated ROS polypeptide, or any oligopeptide thereof, to induce a specific immune response in appropriate animals or cells and to bind with specific antibodies.

The term "biological sample" is used in its broadest sense, and means any biological sample suspected of containing SLC34A2-ROS fusion or truncated ROS polynucleotides or polypeptides or fragments thereof, and may comprise a cell, chromosomes isolated from a cell (e.g., a spread of metaphase chromosomes), genomic DNA (in solution or bound to a solid support such as for Southern analysis), RNA (in solution or bound to a solid support such as for northern analysis), cDNA (in solution or bound to a solid support), an extract from cells, blood, urine, marrow, or a tissue, and the like.

"Characterized by" with respect to a cancer and mutant ROS polynucleotide or polypeptide is meant a cancer in which the SLC34A2-ROS gene translocation and/or expressed fusion polypeptide are present, as compared to a cancer in which such translocation and/or fusion polypeptide are not present. The presence of such fusion polypeptide may drive, in whole or in part, the growth and survival of such cancer.

"Consensus" refers to a nucleic acid sequence which has been re-sequenced to resolve uncalled bases, or which has been extended using XL-PCR™ (Perkin Elmer, Norwalk, Conn.) in the 5' and/or the 3' direction and re-sequenced, or which has been assembled from the overlapping sequences of more than one Incyte clone using the GELVIEW™ Fragment Assembly system (GCG, Madison, Wis.), or which has been both extended and assembled.

"ROS kinase-inhibiting therapeutic" means any composition comprising one or more compounds, chemical or biological, which inhibits, either directly or indirectly, the expression and/or activity of wild type or truncated ROS, either alone and/or as part of the SLC34A2-ROS fusion proteins.

"Derivative" refers to the chemical modification of a nucleic acid sequence encoding SLC34A2-ROS fusion polypeptide or the encoded polypeptide itself. Illustrative of such modifications would be replacement of hydrogen by an alkyl, acyl, or amino group. A nucleic acid derivative would encode a polypeptide that retains essential biological characteristics of the natural molecule.

"Detectable label" with respect to a polypeptide, polynucleotide, or reagent disclosed herein means a chemical, biological, or other modification, including but not limited to fluorescence, mass, residue, dye, radioisotope, label, or tag modifications, etc., by which the presence of the molecule of interest may be detected.

"Expression" or "expressed" with respect to SLC34A2-ROS fusion polypeptide in a biological sample means significantly expressed as compared to control sample in which this fusion polypeptide is not significantly expressed.

"Heavy-isotope labeled peptide" (used interchangeably with AQUA peptide) means a peptide comprising at least one heavy-isotope label, which is suitable for absolute quantification or detection of a protein as described in WO/03016861, "Absolute Quantification of Proteins and Modified Forms Thereof by Multistage Mass Spectrometry" (Gygi et al.), further discussed below. The term "specifically detects" with respect to such an AQUA peptide means the peptide will only detect and quantify polypeptides and proteins that contain the AQUA peptide sequence and will not substantially detect polypeptides and proteins that do not contain the AQUA peptide sequence.

"Isolated" (or "substantially purified") refers to nucleic or amino acid sequences that are removed from their natural environment, isolated or separated. They preferably are at least 60% free, more preferably 75% free, and most preferably 90% or more free from other components with which they are naturally associated.

"Mimetic" refers to a molecule, the structure of which is developed from knowledge of the structure of SLC34A2-ROS fusion polypeptide or portions thereof and, as such, is able to effect some or all of the actions of translocation associated protein-like molecules.

"Mutant ROS" polynucleotide or polypeptide means a SLC34A2-ROS fusion polynucleotide or polypeptide as described herein.

"Polynucleotide" (or "nucleotide sequence") refers to an oligonucleotide, nucleotide, or polynucleotide, and fragments or portions thereof, and to DNA or RNA of genomic or synthetic origin, which may be single- or double-stranded, and represent the sense or anti-sense strand.

"Polypeptide" (or "amino acid sequence") refers to an oligopeptide, peptide, polypeptide, or protein sequence, and fragments or portions thereof, and to naturally occurring or synthetic molecules. Where "amino acid sequence" is recited herein to refer to an amino acid sequence of a naturally occurring protein molecule, "amino acid sequence" and like terms, such as "polypeptide" or "protein", are not meant to limit the amino acid sequence to the complete, native amino acid sequence associated with the recited protein molecule.

"SLC34A2-ROS fusion polynucleotide" refers to the nucleic acid sequence of a substantially purified SLC34A2-ROS translocation gene product or fusion polynucleotide as described herein, obtained from any species, particularly mammalian, including bovine, ovine, porcine, murine, equine, and preferably human, from any source whether natural, synthetic, semi-synthetic, or recombinant.

"SLC34A2-ROS fusion polypeptide" refers to the amino acid sequence of a substantially purified SLC34A2-ROS fusion polypeptide described herein, obtained from any species, particularly mammalian, including bovine, ovine, porcine, murine, equine, and preferably human, from any source whether natural, synthetic, semi-synthetic, or recombinant.

The terms "specifically binds to" (or "specifically binding" or "specific binding") in reference to the interaction of an antibody and a protein or peptide, mean that the interaction is dependent upon the presence of a particular structure (i.e. the antigenic determinant or epitope) on the protein; in other words, the antibody is recognizing and binding to a specific protein structure rather than to proteins in general. The term "does not bind" with respect to an antibody's binding to sequences or antigenic determinants other than that for which it is specific means does not substantially react with as compared to the antibody's binding to antigenic determinant or sequence for which the antibody is specific.

The term "stringent conditions" with respect to sequence or probe hybridization conditions is the "stringency" that occurs within a range from about $T_m$ minus 5° C. (5° C. below the melting temperature ($T_m$) of the probe or sequence) to about 20° C. to 25° C. below $T_m$. Typical stringent conditions are: overnight incubation at 42° C. in a solution comprising: 50% formamide, 5×.SSC (750 mM NaCl, 75 mM trisodium citrate), 50 mM sodium phosphate (pH 7.6), 5×Denhardt's solution, 10% dextran sulfate, and 20 micrograms/ml denatured, sheared salmon sperm DNA, followed by washing the filters in 0.1×SSC at about 65° C. As will be understood by those of skill in the art, the stringency of hybridization may be altered in order to identify or detect identical or related polynucleotide sequences.

A "variant" of SLC34A2-ROS fusion polypeptide polypeptide refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Similar minor variations may also include amino acid deletions or insertions, or both. Guidance in determining which amino acid residues may be substituted, inserted, or deleted without abolishing biological or immunological activity may be found using computer programs well known in the art, for example, DNASTAR software.

A. Identification Mutant ROS Kinase in Human NSCLC.

Figure 1:
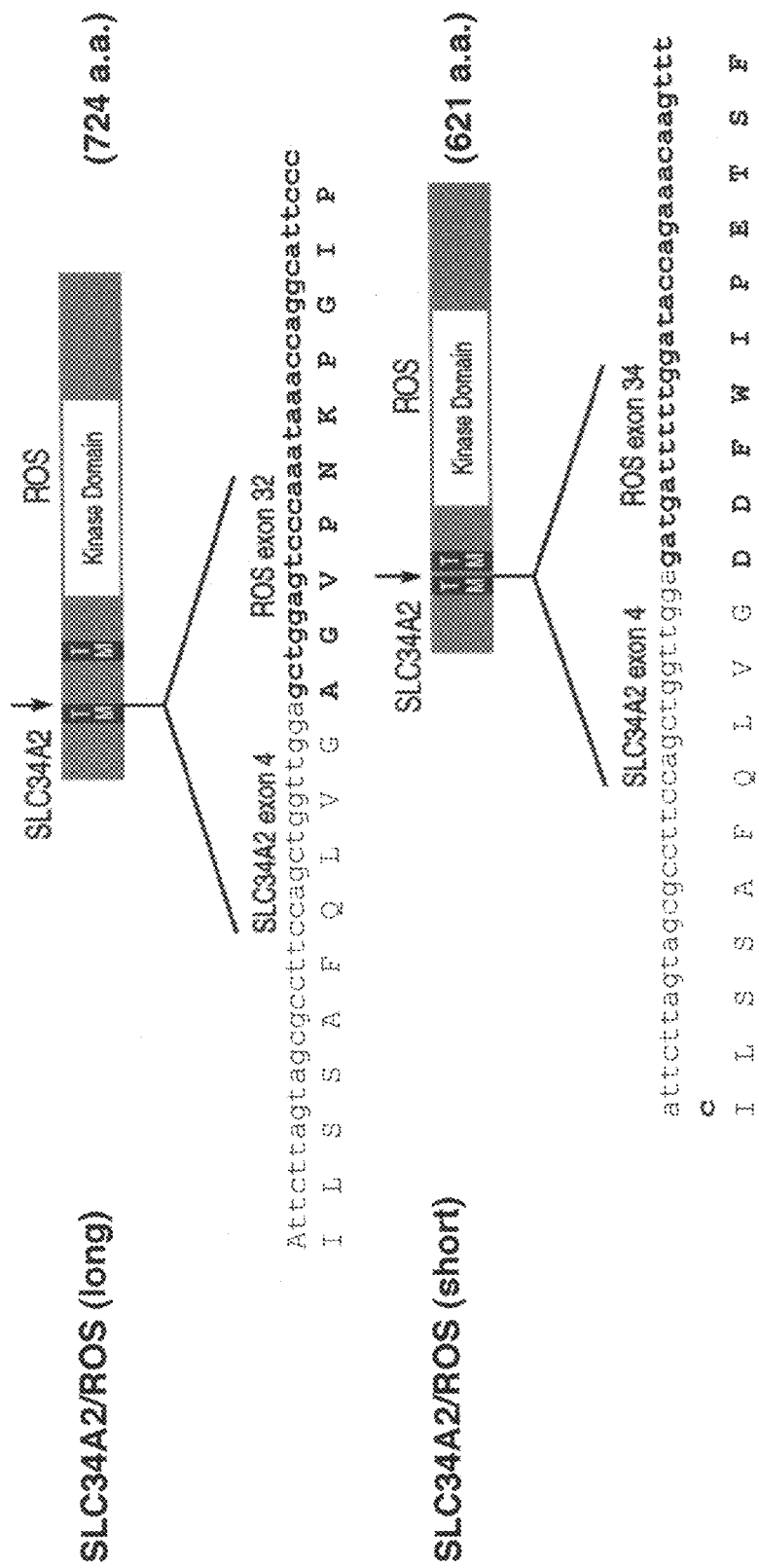
FIG. 1C—shows the location of the two SLC34A2-ROS fusion protein variants. In the first (long) variant, the fusion junction occurs at residue 1750 upstream of the transmembrane domain of ROS, while in the second (short) variant it occurs at residue 1853.

The novel human gene translocation disclosed herein, which occurs between chromosome (4p15) and chromosome (6q22) in human NSCLC and results in expression of two variant fusion proteins that combine the N-terminus (exons 1-4) of SLC34A2 with the transmembrane and kinase domains (exons 32-43 or exons 34-43, respectively) of ROS, was surprisingly identified during examination of global phosphorylated peptide profiles in extracts from a cell line (HCC78) of human non-small cell lung carcinoma (NSCLC), a subtype of lung cancers. The chromosomes, genes, and alternative splice products (long and short) involved in this translocation are shown in FIG. 1.

The phosphorylation profile of this cell line was elucidated using a recently described technique for the isolation and mass spectrometric characterization of modified peptides from complex mixtures (see U.S. Patent Publication No. 20030044848, Rush et al., "Immunoaffinity Isolation of Modified Peptides from Complex Mixtures" (the "IAP" technique), as further described in Example 1 herein. Application of the IAP technique using a phosphotyrosine-specific antibody (CELL SIGNALING TECHNOLOGY, INC., Beverly, Mass., 2003/04 Cat. #9411), identified that the HCC78 cell line expresses ROS kinase (in contrast to most of the other cell lines, which do not), but that the kinase was apparently truncated (see FIG. 5). The screen identified many other activated kinases in the cell line including ROS. Analysis of the sequence 5' to ROS by 5' RACE then identified that the kinase was fused to the N-terminus of SLC34A2 (see FIG. 6).

Figure 5:
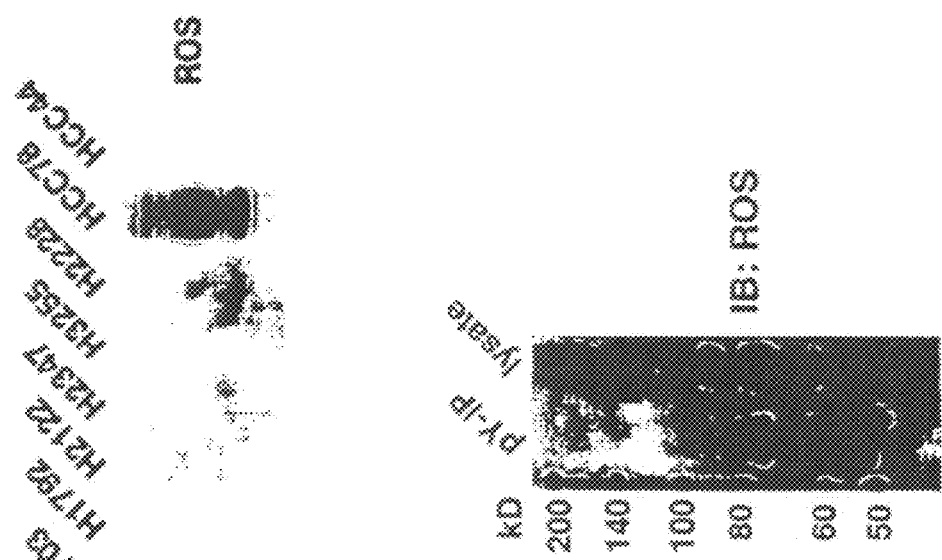
FIG. 5—is a Western blot analysis of extracts from a human NSCLC cell line (HCC78) showing expression of form of ROS having much lower molecular weight than full length/wild-type ROS.
Figure 6:
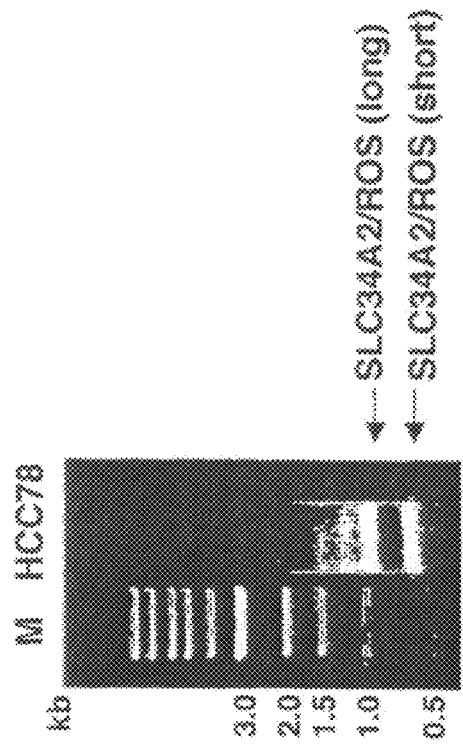
FIG. 6—is a gel depicting detection of ROS via the 5' RACE product with ROS primers after 2 rounds of PCR; the primers employed (SEQ ID NOs: 13-15) are shown.
Figure 7:
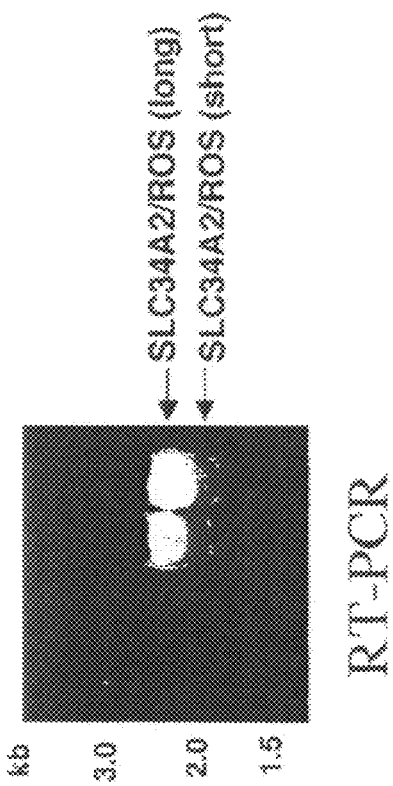
FIG. 7—are gels depicting the detection of the fusion gene formed by the SLC34A2 and ROS translocation by RT-PCR; the protein (and DNA) sequences of the exon 4/exon 32 fusion junction (SEQ ID NO: 9 and SEQ ID NO: 10) and the exon 4/exon34 fusion junction (SEQ ID NO: 11 and SEQ ID NO: 12) of the two respective variants (long and short) are shown.
Figure 8:
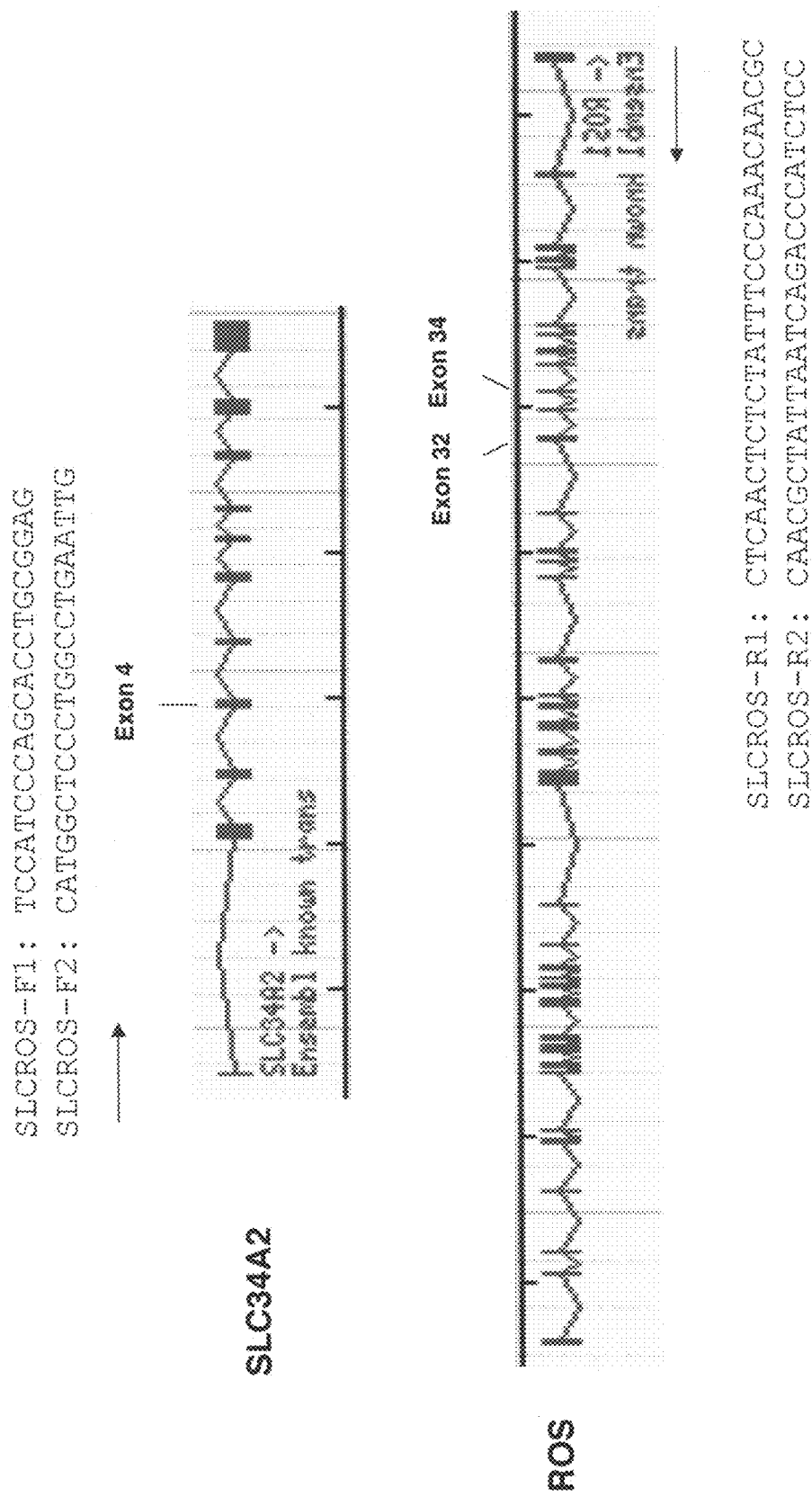
FIG. 8—presents (top) diagrams showing the location of exons 1-4 in the SLC34A2 gene and exons 32-34 in the ROS gene that are involved in the translocation resulting in the fusion protein; arrows indicate the primer locations used for PCR amplification of the fusion protein variants, with primer sequences shown (SEQ ID NOs: 17-20).

Expression of SLC34A2-ROS fusion polypeptide in the HCC78 cell line was then confirmed by Western blot analysis, to examine both ROS kinase expression (fusion protein in the HCC78 cells), and by immunoprecipitation with a p-tyrosine specific antibody to confirm its phosphorylation (see Example 2; FIG. 5). The SLC34A2-ROS fusion gene was amplified by PCR, isolated, and sequenced (see Example 4; FIG. 7 (top panel)). As shown in panel B of FIG. 1, the SLC34A2-ROS translocation combines the N-terminus of SLC34A2 (amino acids 1-126) with the transmembrane and kinase domains of ROS (amino acids 1750-2347 or amino acids 1853-2347, respectively) (see also SEQ ID NOs: 3 and 5), to produce two fusion variants (long and short) (see panel C of FIG. 1). The translocation retains the 5'-most transmembrane domain of SLC34A2. The resulting SLC34A2-ROS fusion proteins, which comprise 724 amino acids and 621 amino acids, respectively, (see panel C of FIG. 1 and FIGS. 2A-B (SEQ ID NOs: 1 and 3)) and are expected to retain kinase activity of ROS. The exons involved and the fusion junctions are shown in FIG. 8.

cDNA encoding the long variant of SLC34A2-ROS fusion protein was then transfected into 293 cells (human embryonic kidney cells) to establish that a fusion protein was expressed with the expected molecular weight as SLC34A2-ROS, which occurs in HCC78 cells. See FIG. 9.

Inhibition of the ROS kinase activity of the SLC34A2-ROS fusion protein may be demonstrated on the HCC78 cell line by using siRNA silencing according to well-known techniques, or by using a targeted kinase inhibitor with activity against ROS. The results of such testing (see Example 3) confirm that the fusion protein is in fact driving the proliferation and survival of this NSCLC cell line. Global phosphopeptide profiling and FISH analysis of human NSCLC tumors indicate that a small percentage of patients do in fact harbor this mutation (see Examples 7 and 9), and these patients may benefit from ROS inhibitor therapy.

B. Isolated Polynucleotides.

The present invention provides, in part, isolated polynucleotides that encode SLC34A2-ROS fusion polypeptides, nucleotide probes that hybridize to such polynucleotides, and methods, vectors, and host cells for utilizing such polynucleotides to produce recombinant fusion polypeptides.

Unless otherwise indicated, all nucleotide sequences determined by sequencing a DNA molecule herein were determined using an automated DNA sequencer (such as the Model 373 from Applied Biosystems, Inc.), and all amino acid sequences of polypeptides encoded by DNA molecules determined herein were determined using an automated peptide sequencer. As is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

Unless otherwise indicated, each nucleotide sequence set forth herein is presented as a sequence of deoxyribonucleotides (abbreviated A, G, C and T). However, by "nucleotide sequence" of a nucleic acid molecule or polynucleotide is intended, for a DNA molecule or polynucleotide, a sequence of deoxyribonucleotides, and for an RNA molecule or polynucleotide, the corresponding sequence of ribonucleotides (A, G, C and U), where each thymidine deoxyribonucleotide (T) in the specified deoxyribonucleotide sequence is replaced by the ribonucleotide uridine (U). For instance, reference to an RNA molecule having the sequence of SEQ ID NOs: 2 or 4 or set forth using deoxyribonucleotide abbreviations is intended to indicate an RNA molecule having a sequence in which each deoxyribonucleotide A, G or C of SEQ ID NOs: 2 or 4 has been replaced by the corresponding ribonucleotide A, G or C, and each deoxyribonucleotide T has been replaced by a ribonucleotide U.

In one embodiment, the invention provides an isolated polynucleotide comprising a nucleotide sequence at least 95% identical to a sequence selected from the group consisting of:

(a) a nucleotide sequence encoding a SLC34A2-ROS fusion polypeptide comprising the amino acid sequence of SEQ ID NO: 1 or SEQ ID NO: 3;

(b) a nucleotide sequence encoding a SLC34A2-ROS fusion polypeptide, said nucleotide sequence comprising the nucleotide sequence of SEQ ID NO: 2 or SEQ ID NO: 4;

(c) a nucleotide sequence encoding a SLC34A2-ROS fusion polypeptide comprising the N-terminal amino acid sequence of SLC34A2 (residues 1-126 of SEQ ID NO: 5) and the kinase domain of ROS (residues 1945-2222 of SEQ ID NO: 7);

(d) a nucleotide sequence comprising the N-terminal nucleotide sequence of SLC34A2 (residues 1-378 of SEQ ID NO: 6) and the kinase domain nucleotide sequence of ROS (residues 6032-6865 of SEQ ID NO: 8);

(e) a nucleotide sequence comprising at least six contiguous nucleotides encompassing the fusion junction (residues 376-381 of SEQ ID NO: 2 or residues 376-381 of SEQ ID NO: 4) of a SLC34A2-ROS fusion polynucleotide;

(f) a nucleotide sequence encoding a polypeptide comprising at least six contiguous amino acids encompassing the fusion junction (residues 126-127 of SEQ ID NO: 1 or residues 126-127 of SEQ ID NO: 3) of a SLC34A2-ROS fusion polypeptide; and (g) a nucleotide sequence complementary to any of the nucleotide sequences of (a)-(f).

Using the information provided herein, such as the nucleotide sequences in FIGS. 2A-B (SEQ ID NOs: 2 and 4), a nucleic acid molecule of the present invention encoding a mutant ROS polypeptide of the invention may be obtained using standard cloning and screening procedures, such as those for cloning cDNAs using mRNA as starting material. Illustrative of the invention, the polynucleotides described in FIGS. 2A-2B (SEQ ID NOs: 2 and 4) were isolated from genomic DNA from a human NSCLC cell line (as further described in Example 4 below). The fusion gene can also be identified in genomic DNA or cDNA libraries in other lung carcinomas or cancers in which the SLC34A2-ROS translocation (4p15, 6q22) occurs, or in which a deletion or alternative translocation results in expression of a truncated ROS kinase lacking the extracellular domain of the wild type kinase.

The determined nucleotide sequence of the SLC34A2-ROS translocation gene products (SEQ ID NO: 2 and SEQ ID NO: 4) encode two kinase fusion protein variants (long and short) of 724 amino acids (see FIG. 2A (SEQ ID NO: 1) and FIG. 1) and 621 amino acids (see FIG. 2B (SEQ ID NO: 3) and FIG. 1), respectively. The SLC34A2-ROS fusion polynucleotides comprise the portion of the nucleotide sequence of wild type SLC34A2 (see FIG. 3 (SEQ ID NO: 6)) that encodes the N-terminus of that protein (exons 1-4) with the portion of the nucleotide sequence of wild type ROS (see FIG. 4 (SEQ ID NO: 8) that encodes the transmembrane and kinase domains of that protein (exons 32-43 or exons 34-43, respectively). See FIG. 1. The kinase domain comprises residues 322-599 in the first (long) variant fusion protein (encoded by nucleotides 964-1797 of the first variant fusion polynucleotide) and residues 219-496 in the second (short) variant fusion protein (encoded by nucleotides 655-1488 of the second variant fusion polynucleotide).

As indicated, the present invention provides, in part, the mature form of the SLC34A2-ROS fusion proteins. According to the signal hypothesis, proteins secreted by mammalian cells have a signal or secretory leader sequence which is cleaved from the mature protein once export of the growing protein chain across the rough endoplasmic reticulum has been initiated. Most mammalian cells and even insect cells cleave secreted proteins with the same specificity. However, in some cases, cleavage of a secreted protein is not entirely uniform, which results in two or more mature species on the protein. Further, it has long been known that the cleavage specificity of a secreted protein is ultimately determined by the primary structure of the complete protein, that is, it is inherent in the amino acid sequence of the polypeptide. Therefore, the present invention provides, in part, nucleotide sequences encoding a mature SLC34A2-ROS fusion polypeptide having the amino acid sequence encoded by the cDNA clone identified as ATCC Deposit No. PTA-7877, which was deposited with the American Type Culture Collection (Manassas, Va., U.S.A.) on Sep. 20, 2006 in accordance with the provisions of the Budapest Treaty.

By the mature SLC34A2-ROS polypeptide having the amino acid sequence encoded by the deposited cDNA clone is meant the mature form of this fusion protein produced by expression in a mammalian cell (e.g., COS cells, as described below) of the complete open reading frame encoded by the human DNA sequence of the clone contained in the vector in the deposited host cell.

As indicated, polynucleotides of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the antisense strand.

Isolated polynucleotides of the invention are nucleic acid molecules, DNA or RNA, which have been removed from their native environment. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

Isolated polynucleotides of the invention include the DNA molecules shown in FIGS. 2A-B (SEQ ID NOs: 2 and 4), DNA molecules comprising the coding sequence for the mature SLC34A2-ROS fusion proteins shown in FIG. 1 (SEQ ID NOs: 1 and 3), and DNA molecules that comprise a sequence substantially different from those described above but which, due to the degeneracy of the genetic code, still a mutant ROS polypeptide of the invention. The genetic code is well known in the art, thus, it would be routine for one skilled in the art to generate such degenerate variants.

In another embodiment, the invention provides an isolated polynucleotide encoding the SLC34A2-ROS fusion polypeptide comprising the SLC34A2-ROS translocation nucleotide sequence contained in the above-described deposited cDNA clone. Preferably, such nucleic acid molecule will encode the mature fusion polypeptide encoded by the deposited cDNA clone. In another embodiment, the invention provides an isolated nucleotide sequence encoding a SLC34A2-ROS fusion polypeptide comprising the N-terminal amino acid sequence of SLC34A2 (residues 1-126 of SEQ ID NO: 5) and the kinase domain of ROS (residues 1945-2222 of SEQ ID NO: 7). In one embodiment, the polypeptide comprising the kinase domain of ROS comprises residues 1750-2347 or 1853-2347 of SEQ ID NO: 7 (see FIG. 1, panel B). In another embodiment, the aforementioned N-terminal amino acid sequence of SLC34A2 and kinase domain of ROS are encoded by nucleotide sequences comprising nucleotides 1-378 of SEQ ID NO: 6 and nucleotides 6032-6865 of SEQ ID NO: 8, respectively.

The invention further provides isolated polynucleotides comprising nucleotide sequences having a sequence complementary to one of the mutant ROS fusion polypeptides of the invention. Such isolated molecules, particularly DNA molecules, are useful as probes for gene mapping, by in situ hybridization with chromosomes, and for detecting expression of the SLC34A2-ROS fusion protein or truncated ROS kinase polypeptide in human tissue, for instance, by Northern blot analysis.

The present invention is further directed to fragments of the isolated nucleic acid molecules described herein. By a fragment of an isolated SLC34A2-ROS polynucleotide or truncated ROS polynucleotide of the invention is intended fragments at least about 15 nucleotides, and more preferably at least about 20 nucleotides, still more preferably at least about 30 nucleotides, and even more preferably, at least about 40 nucleotides in length, which are useful as diagnostic probes and primers as discussed herein. Of course, larger fragments of about 50-1500 nucleotides in length are also useful according to the present invention, as are fragments corresponding to most, if not all, of the SLC34A2-ROS nucleotide sequence of the deposited cDNA or as shown in FIGS. 2A-B (SEQ ID NOs: 2 and 4). By a fragment at least 20 nucleotides in length, for example, is intended fragments that include 20 or more contiguous bases from the respective nucleotide sequences from which the fragments are derived.

Generation of such DNA fragments is routine to the skilled artisan, and may be accomplished, by way of example, by restriction endonuclease cleavage or shearing by sonication of DNA obtainable from the deposited cDNA clone or synthesized according to the sequence disclosed herein. Alternatively, such fragments can be directly generated synthetically.

Preferred nucleic acid fragments or probes of the present invention include nucleic acid molecules encoding the fusion junction of the SLC34A2-ROS translocation gene products (see FIG. 1, panels B and C, and FIG. 7, bottom panel). For example, in certain preferred embodiments, an isolated polynucleotide of the invention comprises a nucleotide sequence/fragment comprising at least six contiguous nucleotides encompassing the fusion junction (residues 376-381 of SEQ ID NO: 2 or residues 376-381 of SEQ ID NO: 4) of a SLC34A2-ROS fusion polynucleotide (see FIG. 7, bottom panel). In another preferred embodiment, an isolated polynucleotide of the invention comprises a nucleotide sequence/fragment that encodes a polypeptide comprising at least six contiguous amino acids encompassing the fusion junction (residues 126-127 of SEQ ID NO: 1 or residues 126-127 of SEQ ID NO: 3) of a SLC34A2-ROS fusion polypeptide (see also FIG. 7, bottom panel (SEQ ID NOs: 9 and 11)).

In another aspect, the invention provides an isolated polynucleotide that hybridizes under stringent hybridization conditions to a portion of an mutant ROS kinase polynucleotide of the invention as described herein. By "stringent hybridization conditions" is intended overnight incubation at 42° C. in a solution comprising: 50% formamide, 5×.SSC (750 mM NaCl, 75 mM trisodium citrate), 50 mM sodium phosphate (pH 7.6), 5×Denhardt's solution, 10% dextran sulfate, and 20 micrograms/ml denatured, sheared salmon sperm DNA, followed by washing the filters in 0.1×SSC at about 65° C.

By a polynucleotide that hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30-70 nt of the reference polynucleotide. These are useful as diagnostic probes and primers (e.g. for PCR) as discussed above and in more detail below.

Of course, polynucleotides hybridizing to a larger portion of the reference polynucleotide (e.g. the mature SLC34A2-ROS fusion polynucleotides described in FIGS. 2A-B (SEQ ID NOs: 2 and 4)), for instance, a portion 50-750 nt in length, or even to the entire length of the reference polynucleotide, are also useful as probes according to the present invention, as are polynucleotides corresponding to most, if not all, of the nucleotide sequence of the deposited cDNA or the nucleotide sequences shown in FIGS. 2A-2B (SEQ ID NOs: 2 or 4) or FIG. 7 (bottom panel) (SEQ ID NOs: 10 and 12).

By a portion of a polynucleotide of "at least 20 nucleotides in length," for example, is intended 20 or more contiguous nucleotides from the nucleotide sequence of the reference polynucleotide. As indicated, such portions are useful diagnostically either as a probe according to conventional DNA hybridization techniques or as primers for amplification of a target sequence by the polymerase chain reaction (PCR), as described, for instance, in MOLECULAR CLONING, A LABORATORY MANUAL, 2nd. edition, Sambrook, J., Fritsch, E. F. and Maniatis, T., eds., Cold Spring Harbor Laboratory Press, Cold Spring Harbor, N.Y. (1989), the entire disclosure of which is hereby incorporated herein by reference. Of course, a polynucleotide which hybridizes only to a poly A sequence (such as the 3' terminal poly(A) tract of the SLC34A2-ROS sequences shown in FIG. 2 (SEQ ID NOs: 2 or 4)) or to a complementary stretch of T (or U) resides, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA clone).

As indicated, nucleic acid molecules of the present invention, which encode a mutant ROS kinase polypeptide of the invention, may include but are not limited to those encoding the amino acid sequence of the mature polypeptide, by itself; the coding sequence for the mature polypeptide and additional sequences, such as those encoding the leader or secretory sequence, such as a pre-, or pro- or pre-pro-protein sequence; the coding sequence of the mature polypeptide, with or without the aforementioned additional coding sequences, together with additional, non-coding sequences, including for example, but not limited to introns and non-coding 5' and 3' sequences, such as the transcribed, non-translated sequences that play a role in transcription, mRNA processing, including splicing and polyadenylation signals, for example—ribosome binding and stability of mRNA; an additional coding sequence which codes for additional amino acids, such as those which provide additional functionalities.

Thus, the sequence encoding the polypeptide may be fused to a marker sequence, such as a sequence encoding a peptide that facilitates purification of the fused polypeptide. In certain preferred embodiments of this aspect of the invention, the marker amino acid sequence is a hexa-histidine peptide, such as the tag provided in a pQE vector (Qiagen, Inc.), among others, many of which are commercially available. As described in Gentz et al., Proc. Natl. Acad. Sci. USA 86: 821-824 (1989), for instance, hexa-histidine provides for convenient purification of the fusion protein. The "HA" tag is another peptide useful for purification which corresponds to an epitope derived from the influenza hemagglutinin protein, which has been described by Wilson et al., Cell 37: 767 (1984). As discussed below, other such fusion proteins include the SLC34A2-ROS fusion polypeptide itself fused to Fc at the N- or C-terminus.

The present invention further relates to variants of the nucleic acid molecules of the present invention, which encode portions, analogs or derivatives of a SLC34A2-ROS fusion polypeptide or truncated ROS kinase polypeptide disclosed herein. Variants may occur naturally, such as a natural allelic variant. By an "allelic variant" is intended one of several alternate forms of a gene occupying a given locus on a chromosome of an organism. See, e.g. GENES II, Lewin, B., ed., John Wiley & Sons, New York (1985). Non-naturally occurring variants may be produced using art-known mutagenesis techniques.

Such variants include those produced by nucleotide substitutions, deletions or additions. The substitutions, deletions or additions may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities (e.g. kinase activity) of the mutant ROS kinase polypeptides disclosed herein. Also especially preferred in this regard are conservative substitutions.

Further embodiments of the invention include isolated polynucleotides comprising a nucleotide sequence at least 90% identical, and more preferably at least 95%, 96%, 97%, 98% or 99% identical, to a mutant ROS polynucleotide of the invention (for example, a nucleotide sequence encoding the RB-ROS fusion polypeptide having the complete amino acid sequence shown in FIGS. 2A-B (SEQ ID NOs: 1 or 3; or a nucleotide sequence encoding the N-terminal of SLC34A2 and the kinase domain of ROS (see FIG. 1, panel B; and FIGS. 3 and 4); or a nucleotide complementary to such exemplary sequences).

By a polynucleotide having a nucleotide sequence at least, for example, 95% "identical" to a reference nucleotide sequence encoding a mutant ROS kinase polypeptide is intended that the nucleotide sequence of the polynucleotide is identical to the reference sequence except that the polynucleotide sequence may include up to five point mutations per each 100 nucleotides of the reference nucleotide sequence encoding the mutant ROS polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 90%, 95%, 96%, 97%, 98% or 99% identical to, for instance, the nucleotide sequences shown in FIGS. 2A-B (SEQ ID NOs: 2 or 4) or to the nucleotide sequence of the deposited cDNA clone described above can be determined conventionally using known computer programs such as the Bestfit program (Wisconsin Sequence Analysis Package, Version 8 for Unix, Genetics Computer Group, University Research Park, 575 Science Drive, Madison, Wis. 53711. Bestfit uses the local homology algorithm of Smith and Waterman, Advances in Applied Mathematics 2: 482-489 (1981), to find the best segment of homology between two sequences. When using Bestfit or any other sequence alignment program to determine whether a particular sequence is, for instance, 95% identical to a reference SLC34A2-ROS fusion polynucleotide sequence according to the present invention, the parameters are set, of course, such that the percentage of identity is calculated over the full length of the reference nucleotide sequence and that gaps in homology of up to 5% of the total number of nucleotides in the reference sequence are allowed.

The present invention includes in its scope nucleic acid molecules at least 90%, 95%, 96%, 97%, 98% or 99% identical to the nucleic acid sequences shown in FIGS. 2A-2B (SEQ ID NOs: 2 or 4), or to nucleotides 379-2172 of SEQ ID NO: 2 or nucleotides 379-1863 of SEQ ID NO: 4, or to the nucleic acid sequence of the deposited cDNA, irrespective of whether they encode a polypeptide having ROS kinase activity. This is because even where a particular nucleic acid molecule does not encode a fusion polypeptide having ROS kinase activity, one of skill in the art would still know how to use the nucleic acid molecule, for instance, as a hybridization probe or a polymerase chain reaction (PCR) primer. Uses of the nucleic acid molecules of the present invention that do not encode a polypeptide having kinase include, inter alia, (1) isolating the SLC34A2-ROS translocation gene or allelic variants thereof in a cDNA library; (2) in situ hybridization (e.g., "FISH") to metaphase chromosomal spreads to provide precise chromosomal location of the SLC34A2-ROS translocation gene, as described in Verma et al., HUMAN CHROMOSOMES: A MANUAL OF BASIC TECHNIQUES, Pergamon Press, New York (1988); and Northern Blot analysis for detecting SLC34A2-ROS fusion protein mRNA expression in specific tissues.

Preferred, however, are nucleic acid molecules having sequences at least 95% identical to a mutant ROS kinase polypeptide of the invention or to the nucleic acid sequence of the deposited cDNA, which do, in fact, encode a fusion polypeptide having ROS kinase activity. Such activity may be similar, but not necessarily identical, to the activity of the SLC34A2-ROS fusion protein disclosed herein (either the full-length protein, the mature protein, or a protein fragment that retains kinase activity), as measured in a particular biological assay. For example, the kinase activity of ROS can be examined by determining its ability to phosphorylate one or more tyrosine containing peptide substrates, for example, "Src-related peptide" (RRLIEDAEYAARG), which is a substrate for many receptor and nonreceptor tyrosine kinases.

Due to the degeneracy of the genetic code, one of ordinary skill in the art will immediately recognize that a large number of the nucleic acid molecules having a sequence at least 90%, 95%, 96%, 97%, 98%, or 99% identical to the nucleic acid sequence of the deposited cDNA or the nucleic acid sequence shown in FIGS. 2A-B (SEQ ID NOs: 2 and 4) will encode a fusion polypeptide having ROS kinase activity. In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide that retains ROS kinase activity. This is because the skilled artisan is fully aware of amino acid substitutions that are either less likely or not likely to significantly effect protein function (e.g., replacing one aliphatic amino acid with a second aliphatic amino acid).

For example, guidance concerning how to make phenotypically silent amino acid substitutions is provided in Bowie et al., "Deciphering the Message in Protein Sequences: Tolerance to Amino Acid Substitutions," Science 247: 1306-1310 (1990), which describes two main approaches for studying the tolerance of an amino acid sequence to change. The first method relies on the process of evolution, in which mutations are either accepted or rejected by natural selection. The second approach uses genetic engineering to introduce amino acid changes at specific positions of a cloned gene and selections or screens to identify sequences that maintain functionality. These studies have revealed that proteins are surprisingly tolerant of amino acid substitutions. Skilled artisans familiar with such techniques also appreciate which amino acid changes are likely to be permissive at a certain position of the protein. For example, most buried amino acid residues require nonpolar side chains, whereas few features of surface side chains are generally conserved. Other such phenotypically silent substitutions are described in Bowie et al., supra., and the references cited therein.

Methods for DNA sequencing that are well known and generally available in the art may be used to practice any polynucleotide embodiments of the invention. The methods may employ such enzymes as the Klenow fragment of DNA polymerase I, SEQUENASE® (US Biochemical Corp, Cleveland, Ohio), Taq polymerase (Perkin Elmer), thermostable T7 polymerase (Amersham, Chicago, Ill.), or combinations of recombinant polymerases and proofreading exonucleases such as the ELONGASE Amplification System marketed by Gibco BRL (Gaithersburg, Md.). Preferably, the process is automated with machines such as the Hamilton Micro Lab 2200 (Hamilton, Reno, Nev.), Peltier Thermal Cycler (PTC200; MJ Research, Watertown, Mass.) and the ABI 377 DNA sequencers (Perkin Elmer).

Polynucleotide sequences encoding a mutant ROS polypeptide of the invention may be extended utilizing a partial nucleotide sequence and employing various methods known in the art to detect upstream sequences such as promoters and regulatory elements. For example, one method that may be employed, "restriction-site" PCR, uses universal primers to retrieve unknown sequence adjacent to a known locus (Sarkar, G., PCR Methods Applic. 2: 318-322 (1993)). In particular, genomic DNA is first amplified in the presence of primer to linker sequence and a primer specific to the known region. Exemplary primers are those described in Example 4 herein. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia et al., Nucleic Acids Res. 16: 8186 (1988)). The primers may be designed using OLIGO 4.06 Primer Analysis software (National Biosciences Inc., Plymouth, Minn.), or another appropriate program, to be 22-30 nucleotides in length, to have a GC content of 50% or more, and to anneal to the target sequence at temperatures about 68-72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom et al., PCR Methods Applic. 1: 111-119 (1991)). In this method, multiple restriction enzyme digestions and ligations may also be used to place an engineered double-stranded sequence into an unknown portion of the DNA molecule before performing PCR. Another method which may be used to retrieve unknown sequences is that described in Parker et al., Nucleic Acids Res. 19: 3055-3060 (1991)). Additionally, one may use PCR, nested primers, and PROMOTERFINDER® libraries to walk in genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences that contain the 5' regions of genes. Use of a randomly primed library may be especially preferable for situations in which an oligo d(T) library does not yield a full-length cDNA. Genomic libraries may be useful for extension of sequence into the 5' and 3' non-transcribed regulatory regions.

Capillary electrophoresis systems, which are commercially available, may be used to analyze the size or confirm the nucleotide sequence of sequencing or PCR products. In particular, capillary sequencing may employ flowable polymers for electrophoretic separation, four different fluorescent dyes (one for each nucleotide) that are laser activated, and detection of the emitted wavelengths by a charge coupled device camera. Output/light intensity may be converted to electrical signal using appropriate software (e.g. GENOTYPER™ and SEQUENCE NAVIGATOR™, Perkin Elmer) and the entire process from loading of samples to computer analysis and electronic data display may be computer controlled. Capillary electrophoresis is especially preferable for the sequencing of small pieces of DNA that might be present in limited amounts in a particular sample.

C. Vectors and Host Cells.

The present invention also provides recombinant vectors that comprise an isolated polynucleotide of the present invention, host cells which are genetically engineered with the recombinant vectors, and the production of recombinant SLC34A2-ROS polypeptides or fragments thereof by recombinant techniques.

Recombinant constructs may be introduced into host cells using well-known techniques such infection, transduction, transfection, transvection, electroporation and transformation. The vector may be, for example, a phage, plasmid, viral or retroviral vector. Retroviral vectors may be replication competent or replication defective. In the latter case, viral propagation generally will occur only in complementing host cells.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

Preferred are vectors comprising cis-acting control regions to the polynucleotide of interest. Appropriate trans-acting factors may be supplied by the host, supplied by a complementing vector or supplied by the vector itself upon introduction into the host. In certain preferred embodiments in this regard, the vectors provide for specific expression, which may be inducible and/or cell type-specific. Particularly preferred among such vectors are those inducible by environmental factors that are easy to manipulate, such as temperature and nutrient additives.

Expression vectors useful in the present invention include chromosomal-, episomal- and virus-derived vectors, e.g., vectors derived from bacterial plasmids, bacteriophage, yeast episomes, yeast chromosomal elements, viruses such as baculoviruses, papova viruses, vaccinia viruses, adenoviruses, fowl pox viruses, pseudorabies viruses and retroviruses, and vectors derived from combinations thereof, such as cosmids and phagemids.

The DNA insert comprising a SLC34A2-ROS polynucleotide or truncated ROS polynucleotide of the invention should be operatively linked to an appropriate promoter, such as the phage lambda PL promoter, the *E. coli* lac, trp and tac promoters, the SV40 early and late promoters and promoters of retroviral LTRs, to name a few. Other suitable promoters are known to the skilled artisan. The expression constructs will further contain sites for transcription initiation, termination and, in the transcribed region, a ribosome binding site for translation. The coding portion of the mature transcripts expressed by the constructs will preferably include a translation initiating at the beginning and a termination codon (UAA, UGA or UAG) appropriately positioned at the end of the polypeptide to be translated.

As indicated, the expression vectors will preferably include at least one selectable marker. Such markers include dihydrofolate reductase or neomycin resistance for eukaryotic cell culture and tetracycline or ampicillin resistance genes for culturing in *E. coli* and other bacteria. Representative examples of appropriate hosts include, but are not limited to, bacterial cells, such as *E. coli, Streptomyces* and *Salmonella typhimurium* cells; fungal cells, such as yeast cells; insect cells such as *Drosophila* S2 and *Spodoptera* Sf9 cells; animal cells such as CHO, COS and Bowes melanoma cells; and plant cells. Appropriate culture mediums and conditions for the above-described host cells are known in the art.

Among vectors preferred for use in bacteria include pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Among known bacterial promoters suitable for use in the present invention include the *E. coli* lacI and lacZ promoters, the T3 and T7 promoters, the gpt promoter, the lambda PR and PL promoters and the trp promoter. Suitable eukaryotic promoters include the CMV immediate early promoter, the HSV thymidine kinase promoter, the early and late SV40 promoters, the promoters of retroviral LTRs, such as those of the Rous sarcoma virus (RSV), and metallothionein promoters, such as the mouse metallothionein-I promoter.

In the yeast, *Saccharomyces cerevisiae*, a number of vectors containing constitutive or inducible promoters such as alpha factor, alcohol oxidase, and PGH may be used. For reviews, see Ausubel et al. (1989) CURRENT PROTOCOLS IN MOLECULAR BIOLOGY, John Wiley & Sons, New York, N.Y., and Grant et al., *Methods Enzymol.* 153: 516-544 (1997).

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., BASIC METHODS IN MOLECULAR BIOLOGY (1986).

Transcription of DNA encoding a SLC34A2-ROS fusion polypeptide of the present invention by higher eukaryotes may be increased by inserting an enhancer sequence into the vector. Enhancers are cis-acting elements of DNA, usually about from 10 to 300 bp that act to increase transcriptional activity of a promoter in a given host cell-type. Examples of enhancers include the SV40 enhancer, which is located on the late side of the replication origin at basepairs 100 to 270, the cytomegalovirus early promoter enhancer, the polyoma enhancer on the late side of the replication origin, and adenovirus enhancers.

For secretion of the translated protein into the lumen of the endoplasmic reticulum, into the periplasmic space or into the extracellular environment, appropriate secretion signals may be incorporated into the expressed polypeptide. The signals may be endogenous to the polypeptide or they may be heterologous signals.

The polypeptide may be expressed in a modified form, such as a fusion protein (e.g. a GST-fusion), and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunoglobulin that is useful to solubilize proteins.

For example, EP-A-0 464 533 (Canadian counterpart 2045869) discloses fusion proteins comprising various portions of constant region of immunoglobin molecules together with another human protein or part thereof. In many cases, the Fc part in a fusion protein is thoroughly advantageous for use in therapy and diagnosis and thus results, for example, in improved pharmacokinetic properties (EP-A 0232 262). On the other hand, for some uses it would be desirable to be able to delete the Fc part after the fusion protein has been expressed, detected and purified in the advantageous manner described. This is the case when Fc portion proves to be a hindrance to use in therapy and diagnosis, for example when the fusion protein is to be used as antigen for immunizations. In drug discovery, for example, human proteins, such as, hIL-5 has been fused with Fc portions for the purpose of high-throughput screening assays to identify antagonists of hIL-5. See Bennett et al., *Journal of Molecular Recognition* 8: 52-58 (1995) and Johanson et al., *The Journal of Biological Chemistry* 270(16): 9459-9471 (1995).

SLC34A2-ROS polypeptides can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

Accordingly, in one embodiment, the invention provides a method for producing a recombinant SLC34A2-ROS fusion polypeptide by culturing a recombinant host cell (as described above) under conditions suitable for the expression of the fusion polypeptide and recovering the polypeptide. Culture conditions suitable for the growth of host cells and the expression of recombinant polypeptides from such cells are well known to those of skill in the art. See, e.g., CURRENT PROTOCOLS IN MOLECULAR BIOLOGY, Ausubel F M et al., eds., Volume 2, Chapter 16, Wiley Interscience.

D. Isolated Polypeptides.

The invention also provides, in part, isolated SLC34A2-ROS fusion polypeptides and fragments thereof. In one embodiment, the invention provides an isolated polypeptide comprising an amino acid sequence at least 95% identical to a sequence selected from the group consisting of:

(a) an amino acid sequence encoding a SLC34A2-ROS fusion polypeptide comprising the amino acid sequence of SEQ ID NO: 1 or SEQ ID NO: 3;

(b) an amino acid sequence encoding a SLC34A2-ROS fusion polypeptide comprising the N-terminal amino acid sequence of SLC34A2 (residues 1-126 of SEQ ID NO: 5) and the kinase domain of ROS (residues 1945-2222 of SEQ ID NO: 7); and (c) an amino acid sequence encoding a polypeptide comprising at least six contiguous amino acids encompassing the fusion junction (residues 126-127 of SEQ ID NO: 1 or residues 126-127 of SEQ ID NO: 3) of a SLC34A2-ROS fusion polypeptide;

In one preferred embodiment, the invention provides an isolated SLC34A2-ROS fusion polypeptide having the amino acid sequence encoded by the deposited cDNA described above (ATCC Deposit No. PTA-7877). In another preferred embodiment, recombinant mutant polypeptides of the invention are provided, which may be produced using a recombinant vector or recombinant host cell as described above.

It will be recognized in the art that some amino acid sequences of a SLC34A2-ROS fusion polypeptide can be varied without significant effect of the structure or function of the mutant protein. If such differences in sequence are contemplated, it should be remembered that there will be critical areas on the protein which determine activity (e.g. the kinase domain of ROS). In general, it is possible to replace residues that form the tertiary structure, provided that residues performing a similar function are used. In other instances, the type of residue may be completely unimportant if the alteration occurs at a non-critical region of the protein.

Thus, the invention further includes variations of a SLC34A2-ROS fusion polypeptide that show substantial ROS kinase activity or that include regions of SLC34A2 and ROS proteins, such as the protein portions discussed below. Such mutants include deletions, insertions, inversions, repeats, and type substitutions (for example, substituting one hydrophilic residue for another, but not strongly hydrophilic for strongly hydrophobic as a rule). Small changes or such "neutral" amino acid substitutions will generally have little effect on activity.

Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr. Examples of conservative amino acid substitutions known to those skilled in the art are: Aromatic: phenylalanine tryptophan tyrosine; Hydrophobic: leucine isoleucine valine; Polar: glutamine asparagines; Basic: arginine lysine histidine; Acidic: aspartic acid glutamic acid; Small: alanine serine threonine methionine glycine. As indicated in detail above, further guidance concerning which amino acid changes are likely to be phenotypically silent (i.e., are not likely to have a significant deleterious effect on a function) can be found in Bowie et al., Science 247, supra.

The polypeptides of the present invention are preferably provided in an isolated form, and preferably are substantially purified. A recombinantly produced version of a SLC34A2-ROS fusion polypeptide of the invention can be substantially purified by the one-step method described in Smith and Johnson, *Gene* 67: 31-40 (1988).

The polypeptides of the present invention include the SLC34A2-ROS fusion polypeptides of FIGS. 2A-B (SEQ ID NOs: 1 and 3) (whether or not including a leader sequence), the fusion polypeptide encoded by the deposited cDNA clone (ATCC No. PTA-7877), an amino acid sequence encoding a SLC34A2-ROS fusion polypeptide comprising the N-terminal amino acid sequence of SLC34A2 (residues 1-126 of SEQ ID NO: 5) and the kinase domain of ROS (residues 1945-2222 of SEQ ID NO: 7), and an amino acid sequence encoding a polypeptide comprising at least six contiguous amino acids encompassing the fusion junction (residues 126-127 of SEQ ID NO: 1 or residues 126-127 of SEQ ID NO: 3) of a SLC34A2-ROS fusion polypeptide (see also FIG. 7, bottom panel), as well as polypeptides that have at least 90% similarity, more preferably at least 95% similarity, and still more preferably at least 96%, 97%, 98% or 99% similarity to those described above.

By "% similarity" for two polypeptides is intended a similarity score produced by comparing the amino acid sequences of the two polypeptides using the Bestfit program (Wisconsin Sequence Analysis Package, Version 8 for Unix, Genetics Computer Group, University Research Park, 575 Science Drive, Madison, Wis. 53711) and the default settings for determining similarity. Bestfit uses the local homology algorithm of Smith and Waterman (*Advances in Applied Mathematics* 2: 482-489 (1981)) to find the best segment of similarity between two sequences.

By a polypeptide having an amino acid sequence at least, for example, 95% "identical" to a reference amino acid sequence of a mutant ROS polypeptide of the invention is intended that the amino acid sequence of the polypeptide is identical to the reference sequence except that the polypeptide sequence may include up to five amino acid alterations per each 100 amino acids of the reference amino acid sequence of the SLC34A2-ROS fusion polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

A SLC34A2-ROS fusion polypeptide of the present invention could be used as a molecular weight marker on SDS-PAGE gels or on molecular sieve gel filtration columns, for example, using methods well known to those of skill in the art.

As further described in detail below, the polypeptides of the present invention can also be used to generate fusion polypeptide specific reagents, such as polyclonal and monoclonal antibodies, which are useful in assays for detecting mutant ROS polypeptide expression as described below or as agonists and antagonists capable of enhancing or inhibiting mutant ROS protein function/activity. Further, such polypeptides can be used in the yeast two-hybrid system to "capture" SLC34A2-ROS fusion polypeptide binding proteins, which are also candidate agonist and antagonist according to the present invention. The yeast two hybrid system is described in Fields and Song, *Nature* 340: 245-246 (1989).

In another aspect, the invention provides a peptide or polypeptide comprising an epitope-bearing portion of a polypeptide of the invention, namely an epitope comprising the fusion junction of a SLC34A2-ROS fusion polypeptide variant (see FIG. 7, bottom panel). The epitope of this polypeptide portion is an immunogenic or antigenic epitope of a polypeptide of the invention. An "immunogenic epitope" is defined as a part of a protein that elicits an antibody response when the whole protein is the immunogen. These immunogenic epitopes are believed to be confined to a few loci on the molecule. On the other hand, a region of a protein molecule to which an antibody can bind is defined as an "antigenic epitope." The number of immunogenic epitopes of a protein generally is less than the number of antigenic epitopes. See, for instance, Geysen of al., *Proc. Natl. Acad. Sci. USA* 81:3998-4002 (1983). The production of fusion polypeptide-specific antibodies of the invention is described in further detail below.

The antibodies raised by antigenic epitope-bearing peptides or polypeptides are useful to detect a mimicked protein, and antibodies to different peptides may be used for tracking the fate of various regions of a protein precursor which undergoes post-translational processing. The peptides and anti-peptide antibodies may be used in a variety of qualitative or quantitative assays for the mimicked protein, for instance in competition assays since it has been shown that even short peptides (e.g., about 9 amino acids) can bind and displace the larger peptides in immunoprecipitation assays. See, for instance, Wilson et al., *Cell* 37: 767-778 (1984) at 777. The anti-peptide antibodies of the invention also are useful for purification of the mimicked protein, for instance, by adsorption chromatography using methods well known in the art. Immunological assay formats are described in further detail below.

Recombinant mutant ROS kinase polypeptides are also within the scope of the present invention, and may be producing using fusion polynucleotides of the invention, as described in Section B above. For example, the invention provides a method for producing a recombinant SLC34A2-ROS fusion polypeptide by culturing a recombinant host cell (as described above) under conditions suitable for the expression of the fusion polypeptide and recovering the polypeptide. Culture conditions suitable for the growth of host cells and the expression of recombinant polypeptides from such cells are well known to those of skill in the art.

E. Mutant-Specific Reagents

Mutant ROS polypeptide-specific reagents useful in the practice of the disclosed methods include, among others, fusion polypeptide specific antibodies and AQUA peptides (heavy-isotope labeled peptides) corresponding to, and suitable for detection and quantification of, SLC34A2-ROS fusion polypeptide expression in a biological sample. A fusion polypeptide-specific reagent is any reagent, biological or chemical, capable of specifically binding to, detecting and/or quantifying the presence/level of expressed SLC34A2-ROS fusion polypeptide in a biological sample. The term includes, but is not limited to, the preferred antibody and AQUA peptide reagents discussed below, and equivalent reagents are within the scope of the present invention.

Antibodies.

Reagents suitable for use in practice of the methods of the invention include a SLC34A2-ROS fusion polypeptide-specific antibody. A fusion-specific antibody of the invention is an isolated antibody or antibodies that specifically bind(s) a SLC34A2-ROS fusion polypeptide of the invention (e.g. SEQ ID NO: 1 or 3) but does not substantially bind either wild type SLC34A2 or wild type ROS. Other suitable reagents include epitope-specific antibodies that specifically bind to an epitope in the extracelluar domain of wild type ROS protein sequence (which domain is not present in the truncated ROS kinase disclosed herein), and are therefore capable of detecting the presence (or absence) of wild type ROS in a sample.

Human SLC34A2-ROS fusion polypeptide-specific antibodies may also bind to highly homologous and equivalent epitopic peptide sequences in other mammalian species, for example murine or rabbit, and vice versa. Antibodies useful in practicing the methods of the invention include (a) monoclonal antibodies, (b) purified polyclonal antibodies that specifically bind to the target polypeptide (e.g. the fusion junction of SLC34A2-ROS fusion polypeptide (see FIG. 7, bottom panel), (c) antibodies as described in (a)-(b) above that bind equivalent and highly homologous epitopes or phosphorylation sites in other non-human species (e.g. mouse, rat), and (d) fragments of (a)-(c) above that bind to the antigen (or more preferably the epitope) bound by the exemplary antibodies disclosed herein.

The term "antibody" or "antibodies" as used herein refers to all types of immunoglobulins, including IgG, IgM, IgA, IgD, and IgE. The antibodies may be monoclonal or polyclonal and may be of any species of origin, including (for example) mouse, rat, rabbit, horse, or human, or may be chimeric antibodies. See, e.g., M. Walker et al., *Molec. Immunol.* 26: 403-11 (1989); Morrision et al., *Proc. Nat'l. Acad. Sci.* 81: 6851 (1984); Neuberger et al., *Nature* 312: 604 (1984)). The antibodies may be recombinant monoclonal antibodies produced according to the methods disclosed in U.S. Pat. No. 4,474,893 (Reading) or U.S. Pat. No. 4,816,567 (Cabilly et al.) The antibodies may also be chemically constructed specific antibodies made according to the method disclosed in U.S. Pat. No. 4,676,980 (Segel et al.)

The preferred epitopic site of a SLC34A2-ROS fusion polypeptide specific antibody of the invention is a peptide fragment consisting essentially of about 11 to 17 amino acids of a human SLC34A2-ROS fusion polypeptide sequence (SEQ ID NOs: 1 or 3) which fragment encompasses the fusion junction (which occurs at residue 126 in the first and second fusion protein variants (see FIG. 1 (panel C) and FIG. 7 (bottom panel)). It will be appreciated that antibodies that specifically binding shorter or longer peptides/epitopes encompassing the fusion junction of a SLC34A2-ROS fusion polypeptide are within the scope of the present invention.

The invention is not limited to use of antibodies, but includes equivalent molecules, such as protein binding domains or nucleic acid aptamers, which bind, in a fusion-protein or truncated-protein specific manner, to essentially the same epitope to which a SLC34A2-ROS fusion polypeptide-specific antibody or ROS truncation point epitope-specific antibody useful in the methods of the invention binds. See, e.g., Neuberger et al., *Nature* 312: 604 (1984). Such equivalent non-antibody reagents may be suitably employed in the methods of the invention further described below.

Polyclonal antibodies useful in practicing the methods of the invention may be produced according to standard techniques by immunizing a suitable animal (e.g., rabbit, goat, etc.) with an antigen encompassing a desired fusion-protein specific epitope (e.g. the fusion junction (see FIG. 7, bottom panel), collecting immune serum from the animal, and separating the polyclonal antibodies from the immune serum, and purifying polyclonal antibodies having the desired specificity, in accordance with known procedures. The antigen may be a synthetic peptide antigen comprising the desired epitopic sequence, selected and constructed in accordance with well-known techniques. See, e.g., ANTIBODIES: A LABORATORY MANUAL, Chapter 5, p. 75-76, Harlow & Lane Eds., Cold Spring Harbor Laboratory (1988); Czernik, *Methods In Enzymology*, 201: 264-283 (1991); Merrifield, *J. Am. Chem. Soc.* 85: 21-49 (1962)). Polyclonal antibodies produced as described herein may be screened and isolated as further described below.

Monoclonal antibodies may also be beneficially employed in the methods of the invention, and may be produced in hybridoma cell lines according to the well-known technique of Kohler and Milstein. *Nature* 265: 495-97 (1975); Kohler and Milstein, *Eur. J. Immunol.* 6: 511 (1976); see also, CURRENT PROTOCOLS IN MOLECULAR BIOLOGY, Ausubel et al. Eds. (1989). Monoclonal antibodies so produced are highly specific, and improve the selectivity and specificity of assay methods provided by the invention. For example, a solution containing the appropriate antigen (e.g. a synthetic peptide comprising the fusion junction of SLC34A2-ROS fusion polypeptide) may be injected into a mouse and, after a sufficient time (in keeping with conventional techniques), the mouse sacrificed and spleen cells obtained. The spleen cells are then immortalized by fusing them with myeloma cells, typically in the presence of polyethylene glycol, to produce hybridoma cells. Rabbit fusion hybridomas, for example, may be produced as described in U.S. Pat. No. 5,675,063, C. Knight, Issued Oct. 7, 1997. The hybridoma cells are then grown in a suitable selection media, such as hypoxanthine-aminopterin-thymidine (HAT), and the supernatant screened for monoclonal antibodies having the desired specificity, as described below. The secreted antibody may be recovered from tissue culture supernatant by conventional methods such as precipitation, ion exchange or affinity chromatography, or the like.

Monoclonal Fab fragments may also be produced in *Escherichia coli* by recombinant techniques known to those skilled in the art. See, e.g., W. Huse, *Science* 246: 1275-81 (1989); Mullinax et al., *Proc. Nat'l Acad. Sci.* 87: 8095 (1990). If monoclonal antibodies of one isotype are preferred for a particular application, particular isotypes can be prepared directly, by selecting from the initial fusion, or prepared secondarily, from a parental hybridoma secreting a monoclonal antibody of different isotype by using the sib selection technique to isolate class-switch variants (Steplewski, et al., *Proc. Nat'l. Acad. Sci.*, 82: 8653 (1985); Spira et al., *J. Immunol. Methods*, 74: 307 (1984)). The antigen combining site of the monoclonal antibody can be cloned by PCR and single-chain antibodies produced as phage-displayed recombinant antibodies or soluble antibodies in *E. coli* (see, e.g., ANTIBODY ENGINEERING PROTOCOLS, 1995, Humana Press, Sudhir Paul editor.)

Further still, U.S. Pat. No. 5,194,392, Geysen (1990) describes a general method of detecting or determining the sequence of monomers (amino acids or other compounds) which is a topological equivalent of the epitope (i.e., a "mimotope") which is complementary to a particular paratope (antigen binding site) of an antibody of interest. More generally, this method involves detecting or determining a sequence of monomers which is a topographical equivalent of a ligand which is complementary to the ligand binding site of a particular receptor of interest. Similarly, U.S. Pat. No. 5,480,971, Houghten et al. (1996) discloses linear $C_1$-C-alkyl peralkylated oligopeptides and sets and libraries of such peptides, as well as methods for using such oligopeptide sets and libraries for determining the sequence of a peralkylated oligopeptide that preferentially binds to an acceptor molecule of interest. Thus, non-peptide analogs of the epitope-bearing peptides of the invention also can be made routinely by these methods.

Antibodies useful in the methods of the invention, whether polyclonal or monoclonal, may be screened for epitope and fusion protein specificity according to standard techniques. See, e.g. Czemik et al., *Methods in Enzymology*, 201: 264-283 (1991). For example, the antibodies may be screened against a peptide library by ELISA to ensure specificity for both the desired antigen and, if desired, for reactivity only with a SLC34A2-ROS fusion polypeptide of the invention and not with wild type SLC34A2 or wild type ROS. The antibodies may also be tested by Western blotting against cell preparations containing target protein to confirm reactivity with the only the desired target and to ensure no appreciable binding to other fusion proteins involving ROS. The production, screening, and use of fusion protein-specific antibodies is known to those of skill in the art, and has been described. See, e.g., U.S. Patent Publication No. 20050214301, Wetzel et al., Sep. 29, 2005.

Fusion polypeptide-specific antibodies useful in the methods of the invention may exhibit some limited cross-reactivity with similar fusion epitopes in other fusion proteins or with the epitopes in wild type SLC34A2 and wild type ROS that form the fusion junction. This is not unexpected as most antibodies exhibit some degree of cross-reactivity, and anti-peptide antibodies will often cross-react with epitopes having high homology or identity to the immunizing peptide. See, e.g., Czemik, supra. Cross-reactivity with other fusion proteins is readily characterized by Western blotting alongside markers of known molecular weight. Amino acid sequences of cross-reacting proteins may be examined to identify sites highly homologous or identical to the SLC34A2-ROS fusion polypeptide sequence to which the antibody binds. Undesirable cross-reactivity can be removed by negative selection using antibody purification on peptide columns (e.g. selecting out antibodies that bind either wild type SLC34A2 and/or wild type ROS).

SLC34A2-ROS fusion polypeptide-specific antibodies of the invention that are useful in practicing the methods disclosed herein are ideally specific for human fusion polypeptide, but are not limited only to binding the human species, per se. The invention includes the production and use of antibodies that also bind conserved and highly homologous or identical epitopes in other mammalian species (e.g. mouse, rat, monkey). Highly homologous or identical sequences in other species can readily be identified by standard sequence comparisons, such as using BLAST, with the human SLC34A2-ROS fusion polypeptide sequences disclosed herein (SEQ ID NOs: 1 and 3).

Antibodies employed in the methods of the invention may be further characterized by, and validated for, use in a particular assay format, for example FC, IHC, and/or ICC. The use of SLC34A2-ROS fusion polypeptide-specific antibodies in such methods is further described in Section F below. Antibodies may also be advantageously conjugated to fluorescent dyes (e.g. Alexa488, PE), or labels such as quantum dots, for use in multi-parametric analyses along with other signal transduction (phospho-AKT, phospho-Erk 1/2) and/or cell marker (cytokeratin) antibodies, as further described in Section F below.

In practicing the methods of the invention, the expression and/or activity of wild type SLC34A2 and/or wild type ROS in a given biological sample may also be advantageously examined using antibodies (either phospho-specific or total) for these wild type proteins. For example, CSF receptor phosphorylation-site specific antibodies are commercially available (see CELL SIGNALING TECHNOLOGY, INC., Beverly Mass., 2005/06 Catalogue, #'s 3151, 3155, and 3154; and Upstate Biotechnology, 2006 Catalogue, #06-457). Such antibodies may also be produced according to standard methods, as described above. The amino acid sequences of both human SLC34A2 and ROS are published (see FIGS. 3 and 4, and referenced SwissProt Accession Nos.), as are the sequences of these proteins from other species.

Detection of wild type SLC34A2 and wild type ROS expression and/or activation, along with SLC34A2-ROS fusion polypeptide expression, in a biological sample (e.g. a tumor sample) can provide information on whether the fusion protein alone is driving the tumor, or whether wild type ROS is also activated and driving the tumor. Such information is clinically useful in assessing whether targeting the fusion protein or the wild type protein(s), or both, or is likely to be most beneficial in inhibiting progression of the tumor, and in selecting an appropriate therapeutic or combination thereof. Antibodies specific for the wild type ROS kinase extracellular domain, which is not present in the truncated ROS kinase disclosed herein, may be particularly useful for determining the presence/absence of the mutant ROS kinase.

It will be understood that more than one antibody may be used in the practice of the above-described methods. For example, one or more SLC34A2-ROS fusion polypeptide-specific antibodies together with one or more antibodies specific for another kinase, receptor, or kinase substrate that is suspected of being, or potentially is, activated in a cancer in which SLC34A2-ROS fusion polypeptide is expressed may be simultaneously employed to detect the activity of such other signaling molecules in a biological sample comprising cells from such cancer.

Those of skill in the art will appreciate that SLC34A2-ROS fusion polypeptides of the present invention and the fusion junction epitope-bearing fragments thereof described above can be combined with parts of the constant domain of immunoglobulins (IgG), resulting in chimeric polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EPA 394,827; Traunecker et al., *Nature* 331: 84-86 (1988)). Fusion proteins that have a disulfide-linked dimeric structure due to the IgG part can also be more efficient in binding and neutralizing other molecules than the monomeric SLC34A2-ROS fusion polypeptide alone (Fountoulakis et al., *J Biochem* 270: 3958-3964 (1995)).

Heavy-Isotope Labeled Peptides (AQUA Peptides).

SLC34A2-ROS fusion polypeptide-specific reagents useful in the practice of the disclosed methods may also comprise heavy-isotope labeled peptides suitable for the absolute quantification of expressed SLC34A2-ROS fusion polypeptide in a biological sample. The production and use of AQUA peptides for the absolute quantification of proteins (AQUA) in complex mixtures has been described. See WO/03016861, "Absolute Quantification of Proteins and Modified Forms Thereof by Multistage Mass Spectrometry," Gygi et al. and also Gerber et al. *Proc. Natl. Acad. Sci. U.S.A.* 100: 6940-5 (2003) (the teachings of which are hereby incorporated herein by reference, in their entirety).

The AQUA methodology employs the introduction of a known quantity of at least one heavy-isotope labeled peptide standard (which has a unique signature detectable by LC-SRM chromatography) into a digested biological sample in order to determine, by comparison to the peptide standard, the absolute quantity of a peptide with the same sequence and protein modification in the biological sample. Briefly, the AQUA methodology has two stages: peptide internal standard selection and validation and method development; and implementation using validated peptide internal standards to detect and quantify a target protein in sample. The method is a powerful technique for detecting and quantifying a given peptide/protein within a complex biological mixture, such as a cell lysate, and may be employed, e.g., to quantify change in protein phosphorylation as a result of drug treatment, or to quantify differences in the level of a protein in different biological states.

Generally, to develop a suitable internal standard, a particular peptide (or modified peptide) within a target protein sequence is chosen based on its amino acid sequence and the particular protease to be used to digest. The peptide is then generated by solid-phase peptide synthesis such that one residue is replaced with that same residue containing stable isotopes ($^{13}$C, $^{15}$N). The result is a peptide that is chemically identical to its native counterpart formed by proteolysis, but is easily distinguishable by MS via a 7-Da mass shift. The newly synthesized AQUA internal standard peptide is then evaluated by LC-MS/MS. This process provides qualitative information about peptide retention by reverse-phase chromatography, ionization efficiency, and fragmentation via collision-induced dissociation. Informative and abundant fragment ions for sets of native and internal standard peptides are chosen and then specifically monitored in rapid succession as a function of chromatographic retention to form a selected reaction monitoring (LC-SRM) method based on the unique profile of the peptide standard.

The second stage of the AQUA strategy is its implementation to measure the amount of a protein or modified protein from complex mixtures. Whole cell lysates are typically fractionated by SDS-PAGE gel electrophoresis, and regions of the gel consistent with protein migration are excised. This process is followed by in-gel proteolysis in the presence of the AQUA peptides and LC-SRM analysis. (See Gerber et al. supra.) AQUA peptides are spiked in to the complex peptide mixture obtained by digestion of the whole cell lysate with a proteolytic enzyme and subjected to immunoaffinity purification as described above. The retention time and fragmentation pattern of the native peptide formed by digestion (e.g. trypsinization) is identical to that of the AQUA internal standard peptide determined previously; thus, LC-MS/MS analysis using an SRM experiment results in the highly specific and sensitive measurement of both internal standard and analyte directly from extremely complex peptide mixtures.

Since an absolute amount of the AQUA peptide is added (e.g. 250 fmol), the ratio of the areas under the curve can be used to determine the precise expression levels of a protein or phosphorylated form of a protein in the original cell lysate. In addition, the internal standard is present during in-gel digestion as native peptides are formed, such that peptide extraction efficiency from gel pieces, absolute losses during sample handling (including vacuum centrifugation), and variability during introduction into the LC-MS system do not affect the determined ratio of native and AQUA peptide abundances.

An AQUA peptide standard is developed for a known sequence previously identified by the IAP-LC-MS/MS method within in a target protein. If the site is modified, one AQUA peptide incorporating the modified form of the particular residue within the site may be developed, and a second AQUA peptide incorporating the unmodified form of the residue developed. In this way, the two standards may be used to detect and quantify both the modified an unmodified forms of the site in a biological sample.

Peptide internal standards may also be generated by examining the primary amino acid sequence of a protein and determining the boundaries of peptides produced by protease cleavage. Alternatively, a protein may actually be digested with a protease and a particular peptide fragment produced can then sequenced. Suitable proteases include, but are not limited to, serine proteases (e.g. trypsin, hepsin), metallo proteases (e.g. PUMP1), chymotrypsin, cathepsin, pepsin, thermolysin, carboxypeptidases, etc.

A peptide sequence within a target protein is selected according to one or more criteria to optimize the use of the peptide as an internal standard. Preferably, the size of the peptide is selected to minimize the chances that the peptide sequence will be repeated elsewhere in other non-target proteins. Thus, a peptide is preferably at least about 6 amino acids. The size of the peptide is also optimized to maximize ionization frequency. Thus, peptides longer than about 20 amino acids are not preferred. The preferred ranged is about 7 to 15 amino acids. A peptide sequence is also selected that is not likely to be chemically reactive during mass spectrometry, thus sequences comprising cysteine, tryptophan, or methionine are avoided.

A peptide sequence that does not include a modified region of the target region may be selected so that the peptide internal standard can be used to determine the quantity of all forms of the protein. Alternatively, a peptide internal standard encompassing a modified amino acid may be desirable to detect and quantify only the modified form of the target protein. Peptide standards for both modified and unmodified regions can be used together, to determine the extent of a modification in a particular sample (i.e. to determine what fraction of the total amount of protein is represented by the modified form). For example, peptide standards for both the phosphorylated and unphosphorylated form of a protein known to be phosphorylated at a particular site can be used to quantify the amount of phosphorylated form in a sample.

The peptide is labeled using one or more labeled amino acids (i.e. the label is an actual part of the peptide) or less preferably, labels may be attached after synthesis according to standard methods. Preferably, the label is a mass-altering label selected based on the following considerations: The mass should be unique to shift fragments masses produced by MS analysis to regions of the spectrum with low background; the ion mass signature component is the portion of the labeling moiety that preferably exhibits a unique ion mass signature in MS analysis; the sum of the masses of the constituent atoms of the label is preferably uniquely different than the fragments of all the possible amino acids. As a result, the labeled amino acids and peptides are readily distinguished from unlabeled ones by the ion/mass pattern in the resulting mass spectrum. Preferably, the ion mass signature component imparts a mass to a protein fragment that does not match the residue mass for any of the natural amino acids.

The label should be robust under the fragmentation conditions of MS and not undergo unfavorable fragmentation. Labeling chemistry should be efficient under a range of conditions, particularly denaturing conditions, and the labeled tag preferably remains soluble in the MS buffer system of choice. The label preferably does not suppress the ionization efficiency of the protein and is not chemically reactive. The label may contain a mixture of two or more isotopically distinct species to generate a unique mass spectrometric pattern at each labeled fragment position. Stable isotopes, such as $^2H$, $^{13}C$, $^{15}N$, $^{17}O$, $^{18}O$, or $^{34}S$, are among preferred labels. Pairs of peptide internal standards that incorporate a different isotope label may also be prepared. Preferred amino acid residues into which a heavy isotope label may be incorporated include leucine, proline, valine, and phenylalanine.

Peptide internal standards are characterized according to their mass-to-charge (m/z) ratio, and preferably, also according to their retention time on a chromatographic column (e.g. an HPLC column). Internal standards that co-elute with unlabeled peptides of identical sequence are selected as optimal internal standards. The internal standard is then analyzed by fragmenting the peptide by any suitable means, for example by collision-induced dissociation (CID) using, e.g., argon or helium as a collision gas. The fragments are then analyzed, for example by multi-stage mass spectrometry ($MS^n$) to obtain a fragment ion spectrum, to obtain a peptide fragmentation signature. Preferably, peptide fragments have significant differences in m/z ratios to enable peaks corresponding to each fragment to be well separated, and a signature is that is unique for the target peptide is obtained. If a suitable fragment signature is not obtained at the first stage, additional stages of MS are performed until a unique signature is obtained.

Fragment ions in the MS/MS and $MS^3$ spectra are typically highly specific for the peptide of interest, and, in conjunction with LC methods, allow a highly selective means of detecting and quantifying a target peptide/protein in a complex protein mixture, such as a cell lysate, containing many thousands or tens of thousands of proteins. Any biological sample potentially containing a target protein/peptide of interest may be assayed. Crude or partially purified cell extracts are preferably employed. Generally, the sample has at least 0.01 mg of protein, typically a concentration of 0.1-10 mg/mL, and may be adjusted to a desired buffer concentration and pH.

A known amount of a labeled peptide internal standard, preferably about 10 femtomoles, corresponding to a target protein to be detected/quantified is then added to a biological sample, such as a cell lysate. The spiked sample is then digested with one or more protease(s) for a suitable time period to allow digestion. A separation is then performed (e.g. by HPLC, reverse-phase HPLC, capillary electrophoresis, ion exchange chromatography, etc.) to isolate the labeled internal standard and its corresponding target peptide from other peptides in the sample. Microcapillary LC is a preferred method.

Each isolated peptide is then examined by monitoring of a selected reaction in the MS. This involves using the prior knowledge gained by the characterization of the peptide internal standard and then requiring the MS to continuously monitor a specific ion in the MS/MS or $MS^n$ spectrum for both the peptide of interest and the internal standard. After elution, the area under the curve (AUC) for both peptide standard and target peptide peaks are calculated. The ratio of the two areas provides the absolute quantification that can be normalized for the number of cells used in the analysis and the protein's molecular weight, to provide the precise number of copies of the protein per cell. Further details of the AQUA methodology are described in Gygi et al., and Gerber et al. supra.

AQUA internal peptide standards (heavy-isotope labeled peptides) may desirably be produced, as described above, to detect any quantify any unique site (e.g. the fusion junction within a SLC34A2-ROS fusion polypeptide) within a mutant ROS polypeptide of the invention. For example, an AQUA phosphopeptide may be prepared that corresponds to the fusion junction sequence of SLC34A2-ROS fusion polypeptide (see FIG. 7 (bottom panel)). Peptide standards for may be produced for the SLC34A2-ROS fusion junction and such standards employed in the AQUA methodology to detect and quantify the fusion junction (i.e. the presence of SLC34A2-ROS fusion polypeptide) in a biological sample.

For example, an exemplary AQUA peptide of the invention comprises the amino acid sequence LVGDDF (see FIG. 7, bottom panel), which corresponds to the three amino acids immediately flanking each side of the fusion junction in the second (short) variant of SLC34A2-ROS fusion polypeptide (see SEQ ID NO: 11). It will be appreciated that larger AQUA peptides comprising the fusion junction sequence (and additional residues downstream or upstream of it) may also be constructed. Similarly, a smaller AQUA peptide comprising less than all of the residues of such sequence (but still comprising the point of fusion junction itself) may alternatively be constructed. Such larger or shorter AQUA peptides are within the scope of the present invention, and the selection and production of preferred AQUA peptides may be carried out as described above (see Gygi et al., Gerber et al., supra.).

Nucleic Acid Probes.

Fusion-specific reagents provided by the invention also include nucleic acid probes and primers suitable for detection of a SLC34A2-ROS polynucleotide, as described in detail in Section B above. The specific use of such probes in assays such as fluorescence in-situ hybridization (FISH) or PCR amplification is described in Section F below.

Also provided by the invention is a kit for the detection of a SLC34A2-ROS fusion polynucleotide and/or polypeptide in a biological sample, the kit comprising at least one fusion polynucleotide- or polypeptide-specific reagent of the invention, and one or more secondary reagents. Suitable secondary reagents for employment in a kit are familiar to those of skill in the art, and include, by way of example, buffers, detectable secondary antibodies or probes, kinases, activating agents, kinase substrates, and the like.

F. Diagnostic Applications & Assay Formats.

The methods of the invention may be carried out in a variety of different assay formats known to those of skill in the art.

Immunoassays.

Immunoassays useful in the practice of the methods of the invention may be homogenous immunoassays or heterogeneous immunoassays. In a homogeneous assay the immunological reaction usually involves a mutant ROS polypeptide-specific reagent (e.g. a SLC34A2-ROS fusion polypeptide-specific antibody), a labeled analyte, and the biological sample of interest. The signal arising from the label is modified, directly or indirectly, upon the binding of the antibody to the labeled analyte. Both the immunological reaction and detection of the extent thereof are carried out in a homogeneous solution. Immunochemical labels that may be employed include free radicals, radio-isotopes, fluorescent dyes, enzymes, bacteriophages, coenzymes, and so forth. Semi-conductor nanocrystal labels, or "quantum dots", may also be advantageously employed, and their preparation and use has been well described. See generally, K. Barovsky, *Nanotech. Law & Bus.* 1(2): Article 14 (2004) and patents cited therein.

In a heterogeneous assay approach, the reagents are usually the biological sample, a mutant ROS kinase polypeptide-specific reagent (e.g., an antibody), and suitable means for producing a detectable signal. Biological samples as further described below may be used. The antibody is generally immobilized on a support, such as a bead, plate or slide, and contacted with the sample suspected of containing the antigen in a liquid phase. The support is then separated from the liquid phase and either the support phase or the liquid phase is examined for a detectable signal employing means for producing such signal. The signal is related to the presence of the analyte in the biological sample. Means for producing a detectable signal include the use of radioactive labels, fluorescent labels, enzyme labels, quantum dots, and so forth. For example, if the antigen to be detected contains a second binding site, an antibody which binds to that site can be conjugated to a detectable group and added to the liquid phase reaction solution before the separation step. The presence of the detectable group on the solid support indicates the presence of the antigen in the test sample. Examples of suitable immunoassays are the radioimmunoassay, immunofluorescence methods, enzyme-linked immunoassays, and the like.

Immunoassay formats and variations thereof, which may be useful for carrying out the methods disclosed herein, are well known in the art. See generally E. Maggio, Enzyme-Immunoassay, (1980) (CRC Press, Inc., Boca Raton, Fla.); see also, e.g., U.S. Pat. No. 4,727,022 (Skold et al., "Methods for Modulating Ligand-Receptor Interactions and their Application"); U.S. Pat. No. 4,659,678 (Forrest et al., "Immunoassay of Antigens"); U.S. Pat. No. 4,376,110 (David et al., "Immunometric Assays Using Monoclonal Antibodies"). Conditions suitable for the formation of reagent-antibody complexes are well known to those of skill in the art. See id. SLC34A2-ROS fusion polypeptide-specific monoclonal antibodies may be used in a "two-site" or "sandwich" assay, with a single hybridoma cell line serving as a source for both the labeled monoclonal antibody and the bound monoclonal antibody. Such assays are described in U.S. Pat. No. 4,376, 110. The concentration of detectable reagent should be sufficient such that the binding of SLC34A2-ROS fusion polypeptide is detectable compared to background.

Antibodies useful in the practice of the methods disclosed herein may be conjugated to a solid support suitable for a diagnostic assay (e.g., beads, plates, slides or wells formed from materials such as latex or polystyrene) in accordance with known techniques, such as precipitation. Antibodies or other SLC34A2-ROS fusion polypeptide-binding reagents may likewise be conjugated to detectable groups such as radiolabels (e.g., $^{35}$S, $^{125}$I, $^{131}$I), enzyme labels (e.g., horseradish peroxidase, alkaline phosphatase), and fluorescent labels (e.g., fluorescein) in accordance with known techniques.

Cell-based assays, such flow cytometry (FC), immunohistochemistry (IHC), or immunofluorescence (IF) are particularly desirable in practicing the methods of the invention, since such assay formats are clinically-suitable, allow the detection of mutant ROS polypeptide expression in vivo, and avoid the risk of artifact changes in activity resulting from manipulating cells obtained from, e.g. a tumor sample in order to obtain extracts. Accordingly, in some preferred embodiment, the methods of the invention are implemented in a flow-cytometry (FC), immuno-histochemistry (IHC), or immunofluorescence (IF) assay format.

Flow cytometry (FC) may be employed to determine the expression of mutant ROS polypeptide in a mammalian tumor before, during, and after treatment with a drug targeted at inhibiting ROS kinase activity. For example, tumor cells from a fine needle aspirate may be analyzed by flow cytometry for SLC34A2-ROS fusion polypeptide expression and/or activation, as well as for markers identifying cancer cell types, etc., if so desired. Flow cytometry may be carried out according to standard methods. See, e.g. Chow et al., *Cytometry (Communications in Clinical Cytometry)* 46: 72-78 (2001). Briefly and by way of example, the following protocol for cytometric analysis may be employed: fixation of the cells with 2% paraformaldehyde for 10 minutes at 37° C. followed by permeabilization in 90% methanol for 30 minutes on ice. Cells may then be stained with the primary SLC34A2-ROS fusion polypeptide-specific antibody, washed and labeled with a fluorescent-labeled secondary antibody. The cells would then be analyzed on a flow cytometer (e.g. a Beckman Coulter FC500) according to the specific protocols of the instrument used. Such an analysis would identify the level of expressed SLC34A2-ROS fusion polypeptide in the tumor. Similar analysis after treatment of the tumor with a ROS-inhibiting therapeutic would reveal the responsiveness of a SLC34A2-ROS fusion polypeptide-expressing tumor to the targeted inhibitor of ROS kinase.

Immunohistochemical (IHC) staining may be also employed to determine the expression and/or activation status of mutant ROS kinase polypeptide in a mammalian cancer (e.g. NSCLC) before, during, and after treatment with a drug targeted at inhibiting ROS kinase activity. IHC may be carried out according to well-known techniques. See, e.g., ANTIBODIES: A LABORATORY MANUAL, Chapter 10, Harlow & Lane Eds., Cold Spring Harbor Laboratory (1988). Briefly, and by way of example, paraffin-embedded tissue (e.g. tumor tissue from a biopsy) is prepared for immunohistochemical staining by deparaffinizing tissue sections with xylene followed by ethanol; hydrating in water then PBS; unmasking antigen by heating slide in sodium citrate buffer; incubating sections in hydrogen peroxide; blocking in blocking solution; incubating slide in primary anti-SLC34A2-ROS fusion polypeptide antibody and secondary antibody; and finally detecting using ABC avidin/biotin method according to manufacturer's instructions.

Immunofluorescence (IF) assays may be also employed to determine the expression and/or activation status of SLC34A2-ROS fusion polypeptide in a mammalian cancer before, during, and after treatment with a drug targeted at inhibiting ROS kinase activity. IF may be carried out according to well-known techniques. See, e.g., J. M. polak and S. Van Noorden (1997) INTRODUCTION TO IMMUNOCYTOCHEMISTRY, 2nd Ed.; ROYAL MICROSCOPY SOCIETY MICROSCOPY HANDBOOK 37, BioScientific/Springer-Verlag. Briefly, and by way of example, patient samples may be fixed in paraformaldehyde followed by methanol, blocked with a blocking solution such as horse serum, incubated with the primary antibody against SLC34A2-ROS fusion polypeptide followed by a secondary antibody labeled with a fluorescent dye such as Alexa 488 and analyzed with an epifluorescent microscope.

Antibodies employed in the above-described assays may be advantageously conjugated to fluorescent dyes (e.g. Alexa488, PE), or other labels, such as quantum dots, for use in multi-parametric analyses along with other signal transduction (EGFR, phospho-AKT, phospho-Erk 1/2) and/or cell marker (cytokeratin) antibodies.

A variety of other protocols, including enzyme-linked immunosorbent assay (ELISA), radio-immunoassay (RIA), and fluorescent-activated cell sorting (FACS), for measuring mutant ROS kinase polypeptides are known in the art and provide a basis for diagnosing altered or abnormal levels of SLC34A2-ROS fusion polypeptide expression. Normal or standard values for SLC34A2-ROS fusion polypeptide expression are established by combining body fluids or cell extracts taken from normal mammalian subjects, preferably human, with antibody to SLC34A2-ROS fusion polypeptide under conditions suitable for complex formation. The amount of standard complex formation may be quantified by various methods, but preferably by photometric means. Quantities of SLC34A2-ROS fusion polypeptide expressed in subject, control, and disease samples from biopsied tissues are compared with the standard values. Deviation between standard and subject values establishes the parameters for diagnosing disease.

Peptide & Nucleotide Assays.

Similarly, AQUA peptides for the detection/quantification of expressed mutant ROS polypeptide in a biological sample comprising cells from a tumor may be prepared and used in standard AQUA assays, as described in detail in Section E above. Accordingly, in some preferred embodiments of the methods of the invention, the SLC34A2-ROS fusion polypeptide-specific reagent comprises a heavy isotope labeled phosphopeptide (AQUA peptide) corresponding to a peptide sequence comprising the fusion junction of SLC34A2-ROS fusion polypeptide, as described above in Section E.

Mutant ROS kinase polypeptide-specific reagents useful in practicing the methods of the invention may also be mRNA, oligonucleotide or DNA probes that can directly hybridize to, and detect, fusion or truncated polypeptide expression transcripts in a biological sample. Such probes are discussed in detail in Section B above. Briefly, and by way of example, formalin-fixed, paraffin-embedded patient samples may be probed with a fluorescein-labeled RNA probe followed by washes with formamide, SSC and PBS and analysis with a fluorescent microscope.

Polynucleotides encoding mutant ROS kinase polypeptide may also be used for diagnostic purposes. The polynucleotides that may be used include oligonucleotide sequences, antisense RNA and DNA molecules, and PNAs. The polynucleotides may be used to detect and quantitate gene expression in biopsied tissues in which expression of SLC34A2-ROS fusion polypeptide or truncated ROS polypeptide may be correlated with disease. The diagnostic assay may be used to distinguish between absence, presence, and excess expression of SLC34A2-ROS fusion polypeptide, and to monitor regulation of SLC34A2-ROS fusion polypeptide levels during therapeutic intervention.

In one preferred embodiment, hybridization with PCR probes which are capable of detecting polynucleotide sequences, including genomic sequences, encoding SLC34A2-ROS fusion polypeptide or truncated ROS kinase polypeptide or closely related molecules, may be used to identify nucleic acid sequences that encode mutant ROS polypeptide. The construction and use of such probes is described in Section B above. The specificity of the probe, whether it is made from a highly specific region, e.g., 10 unique nucleotides in the fusion junction, or a less specific region, e.g., the 3' coding region, and the stringency of the hybridization or amplification (maximal, high, intermediate, or low) will determine whether the probe identifies only naturally occurring sequences encoding mutant ROS kinase polypeptide, alleles, or related sequences.

Probes may also be used for the detection of related sequences, and should preferably contain at least 50% of the nucleotides from any of the mutant ROS polypeptide encoding sequences. The hybridization probes of the subject invention may be DNA or RNA and derived from the nucleotide sequences of SEQ ID NOs: 2 or 4, most preferably encompassing the fusion junction (see FIG. 7, bottom panel), or from genomic sequence including promoter, enhancer elements, and introns of the naturally occurring SLC34A2 and ROS polypeptides, as further described in Section B above.

A SLC34A2-ROS fusion polynucleotide or truncated ROS polynucleotide of the invention may be used in Southern or northern analysis, dot blot, or other membrane-based technologies; in PCR technologies; or in dip stick, pin, ELISA or chip assays utilizing fluids or tissues from patient biopsies to detect altered mutant ROS kinase polypeptide expression. Such qualitative or quantitative methods are well known in the art. In a particular aspect, the nucleotide sequences encoding mutant ROS polypeptide may be useful in assays that detect activation or induction of various cancers, including cancers of the lung including NSCLC. Mutant ROS polynucleotides may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequences have hybridized with nucleotide sequences in the sample, and the presence of altered levels of nucleotide sequences encoding SLC34A2-ROS fusion polypeptide or truncated ROS kinase polypeptide in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease characterized by expression of mutant ROS polypeptide, a normal or standard profile for expression is established. This may be accomplished by combining body fluids or cell extracts taken from normal subjects, either animal or human, with a sequence, or a fragment thereof, which encodes SLC34A2-ROS fusion polypeptide or truncated ROS kinase polypeptide, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

Additional diagnostic uses for mutant ROS polynucleotides of the invention may involve the use of polymerase chain reaction (PCR), another preferred assay format that is standard to those of skill in the art. See, e.g., MOLECULAR CLONING, A LABORATORY MANUAL, 2nd. edition, Sambrook, J., Fritsch, E. F. and Maniatis, T., eds., Cold Spring Harbor Laboratory Press, Cold Spring Harbor, N.Y. (1989). PCR oligomers may be chemically synthesized, generated enzymatically, or produced from a recombinant source. Oligomers will preferably consist of two nucleotide sequences, one with sense orientation (5' to 3') and another with antisense (3' to 5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of SLC34A2-ROS fusion polypeptide or truncated ROS kinase polypeptide include radiolabeling or biotinylating nucleotides, coamplification of a control nucleic acid, and standard curves onto which the experimental results are interpolated (Melby et al., *J. Immunol. Methods,* 159: 235-244 (1993); Duplaa et al. *Anal. Biochem.* 229-236 (1993)). The speed of quantitation of multiple samples may be accelerated by running the assay in an ELISA format where the oligomer of interest is presented in various dilutions and a spectrophotometric or colorimetric response gives rapid quantitation.

In another embodiment of the invention, the mutant ROS polynucleotides of the invention may be used to generate hybridization probes which are useful for mapping the naturally occurring genomic sequence. The sequences may be mapped to a particular chromosome or to a specific region of the chromosome using well known techniques. Such techniques include fluorescence in-situ hybridization (FISH), FACS, or artificial chromosome constructions, such as yeast artificial chromosomes, bacterial artificial chromosomes, bacterial P1 constructions or single chromosome cDNA libraries, as reviewed in Price, C. M., *Blood Rev.* 7: 127-134 (1993), and Trask, B. J., *Trends Genet.* 7: 149-154 (1991).

In one preferred embodiment, FISH is employed (as described in Verma et al. HUMAN CHROMOSOMES: A MANUAL OF BASIC TECHNIQUES, Pergamon Press, New York, N.Y. (1988)) and may be correlated with other physical chromosome mapping techniques and genetic map data. Examples of genetic map data can be found in the 1994 Genome Issue of *Science* (265: 1981f). Correlation between the location of the gene encoding SLC34A2-ROS fusion polypeptide or truncated ROS polypeptide on a physical chromosomal map and a specific disease, or predisposition to a specific disease, may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22-23 (Gatti et al., *Nature* 336: 577-580 (1988)), any sequences mapping to that area may represent associated or regulatory genes for further investigation. The nucleotide sequence of the subject invention may also be used to detect differences in the chromosomal location due to translocation, inversion, etc., among normal, carrier, or affected individuals.

Biological Samples

Biological samples useful in the practice of the methods of the invention may be obtained from any mammal in which a cancer characterized by the presence of a SLC34A2-ROS fusion polypeptide is or might be present or developing. In one embodiment, the mammal is a human, and the human may be a candidate for a ROS-inhibiting therapeutic, for the treatment of a lung cancer, e.g. NSCLC. The human candidate may be a patient currently being treated with, or considered for treatment with, a ROS kinase inhibitor. In another embodiment, the mammal is large animal, such as a horse or cow, while in other embodiments, the mammal is a small animal, such as a dog or cat, all of which are known to develop cancers, including lung cancers.

Any biological sample comprising cells (or extracts of cells) from a mammalian cancer is suitable for use in the methods of the invention. In one embodiment, the biological sample comprises cells obtained from a tumor biopsy. The biopsy may be obtained, according to standard clinical techniques, from primary tumors occurring in an organ of a mammal, or by secondary tumors that have metastasized in other tissues. In another embodiment, the biological sample comprises cells obtained from a fine needle aspirate taken from a tumor, and techniques for obtaining such aspirates are well known in the art (see Cristallini et al., *Acta Cytol.* 36(3): 416-22 (1992))

The biological sample may also comprise cells obtained from an effusion, such as a pleural effusion. Pleural effusions (liquid that forms outside the lung in the thoracic cavity and which contains cancerous cells) are known to form in many patients with advanced lung cancer (including NSCLC), and the presence of such effusion is predictive of a poor outcome and short survival time. Standard techniques for obtaining pleural effusion samples have been described and are well known in the art (see Sahn, *Clin Chest Med.* 3(2): 443-52 (1982)). Circulating tumor cells may also be obtained from serum using tumor markers, cytokeratin protein markers or other methods of negative selection as described (see Ma et al., *Anticancer Res.* 23(1A): 49-62 (2003)). Serum and bone marrow samples may be particularly preferred for patients with leukemia. Aberrant expression of ROS has been observed in a glioblastoma. See Charest et al., supra.

A biological sample may comprise cells (or cell extracts) from a cancer in which SLC34A2-ROS fusion polypeptide or truncated ROS kinase polypeptide is expressed and/or activated but wild type ROS kinase is not. Alternatively, the sample may comprise cells from a cancer in which both mutant ROS polypeptide and wild type ROS kinase are expressed and/or activated, or in which wild type ROS kinase and/or SLC34A2 are expressed and/or active, but mutant ROS polypeptide is not.

Cellular extracts of the foregoing biological samples may be prepared, either crude or partially (or entirely) purified, in accordance with standard techniques, and used in the methods of the invention. Alternatively, biological samples comprising whole cells may be utilized in preferred assay formats such as immunohistochemistry (IHC), flow cytometry (FC), and immunofluorescence (IF), as further described above. Such whole-cell assays are advantageous in that they minimize manipulation of the tumor cell sample and thus reduce the risks of altering the in vivo signaling/activation state of the cells and/or introducing artifact signals. Whole cell assays are also advantageous because they characterize expression and signaling only in tumor cells, rather than a mixture of tumor and normal cells.

In practicing the disclosed method for determining whether a compound inhibits progression of a tumor characterized by a SLC34A2-ROS translocation and/or fusion polypeptide, biological samples comprising cells from mammalian xenografts (or bone marrow transplants) may also be advantageously employed. Preferred xenografts (or transplant recipients) are small mammals, such as mice, harboring human tumors (or leukemias) that express a mutant ROS kinase polypeptide. Xenografts harboring human tumors are well known in the art (see Kal, *Cancer Treat Res.* 72: 155-69 (1995)) and the production of mammalian xenografts harboring human tumors is well described (see Winograd et al., *In Vivo.* 1(1): 1-13 (1987)). Similarly the generation and use of bone marrow transplant models is well described (see, e.g., Schwaller, et al., *EMBO J.* 17: 5321-333 (1998); Kelly et al., *Blood* 99: 310-318 (2002)). By "cancer characterized by" a SLC34A2-ROS translocation and/or fusion polypeptide is meant a cancer in which such mutant ROS gene and/or expressed polypeptide are present, as compared to a cancer in which such translocation and/or fusion polypeptide are not present.

In assessing mutant ROS polynucleotide presence or polypeptide expression in a biological sample comprising cells from a mammalian cancer tumor, a control sample representing a cell in which such translocation and/or fusion protein do not occur may desirably be employed for comparative purposes. Ideally, the control sample comprises cells from a subset of the particular cancer (e.g. NSCLC) that is representative of the subset in which the mutation (e.g. SLC34A2-ROS translocation) does not occur and/or the fusion polypeptide is not expressed. Comparing the level in the control sample versus the test biological sample thus identifies whether the mutant polynucleotide and/or polypeptide is/are present. Alternatively, since SLC34A2-ROS fusion polynucleotide and/or polypeptide may not be present in the majority of cancers, any tissue that similarly does not express mutant ROS polypeptide (or harbor the mutant polynucleotide) may be employed as a control.

The methods described below will have valuable diagnostic utility for cancers characterized by mutant ROS polynucleotide and/or polypeptide, and treatment decisions pertaining to the same. For example, biological samples may be obtained from a subject that has not been previously diagnosed as having a cancer characterized by since a SLC34A2-ROS translocation and/or fusion polypeptide, nor has yet undergone treatment for such cancer, and the method is employed to diagnostically identify a tumor in such subject as belonging to a subset of tumors (e.g. NSCLC tumors) in which mutant ROS polynucleotide and/or polypeptide is present/expressed.

Alternatively, a biological sample may be obtained from a subject that has been diagnosed as having a cancer driven by one type of kinase, such as EFGR, and has been receiving therapy, such as EGFR inhibitor therapy (e.g. Tarceva™, Iressa™) for treatment of such cancer, and the method of the invention is employed to identify whether the subject's tumor is also characterized by a SLC34A2-ROS translocation and/or fusion polypeptide, and is therefore likely to fully respond to the existing therapy and/or whether alternative or additional ROS kinase-inhibiting therapy is desirable or warranted. The methods of the invention may also be employed to monitor the progression or inhibition of a mutant ROS polypeptide-expressing cancer following treatment of a subject with a composition comprising a ROS kinase-inhibiting therapeutic or combination of therapeutics.

Such diagnostic assay may be carried out subsequent to or prior to preliminary evaluation or surgical surveillance procedures. The identification method of the invention may be advantageously employed as a diagnostic to identify patients having cancer, such as NSCLC, driven by the SLC34A2-ROS fusion protein, which patients would be most likely to respond to therapeutics targeted at inhibiting ROS kinase activity. The ability to select such patients would also be useful in the clinical evaluation of efficacy of future ROS-targeted therapeutics as well as in the future prescription of such drugs to patients.

Diagnostics.

The ability to selectively identify cancers in which a SLC34A2-ROS translocation and/or fusion polypeptide is/are present enables important new methods for accurately identifying such tumors for diagnostic purposes, as well as obtaining information useful in determining whether such a tumor is likely to respond to a ROS-inhibiting therapeutic composition, or likely to be partially or wholly non-responsive to an inhibitor targeting a different kinase when administered as a single agent for the treatment of the caner.

Accordingly, in one embodiment, the invention provides a method for detecting the presence of a mutant ROS polynucleotide and/or polypeptide in a cancer, the method comprising the steps of:

(a) obtaining a biological sample from a patient having cancer; and (b) utilizing at least one reagent that detects a mutant ROS polynucleotide or polypeptide of the invention to determine whether a SLC34A2-ROS fusion polynucleotide and/or polypeptide is/are present in the biological sample.

In some preferred embodiments, the cancer is a lung cancer, such as non-small cell lung carcinoma (NSCLC). In other preferred embodiments, the presence of a mutant ROS kinase polypeptide identifies a cancer that is likely to respond to a composition comprising at least one ROS kinase-inhibiting therapeutic.

In some preferred embodiments, the diagnostic methods of the invention are implemented in a flow-cytometry (FC), immuno-histochemistry (IHC), or immuno-fluorescence (IF) assay format. In another preferred embodiment, the activity of the SLC34A2-ROS fusion polypeptide is detected. In other preferred embodiments, the diagnostic methods of the invention are implemented in a fluorescence in situ hybridization (FISH) or polymerase chain reaction (PCR) assay format.

The invention further provides a method for determining whether a compound inhibits the progression of a cancer characterized by a SLC34A2-ROS fusion polynucleotide or polypeptide, said method comprising the step of determining whether said compound inhibits the expression and/or activity of said SLC34A2-ROS fusion in said cancer. In one preferred embodiment, inhibition of expression and/or activity of the SLC34A2-ROS fusion polypeptide is determined using at least one reagent that detects an SLC34A2-ROS fusion polynucleotide or polypeptide of the invention. Compounds suitable for inhibition of ROS kinase activity are discussed in more detail in Section G below.

Mutant ROS polynucleotide probes and polypeptide-specific reagents useful in the practice of the methods of the invention are described in further detail in sections B and D above. In one preferred embodiment, the SLC34A2-ROS fusion polypeptide-specific reagent comprises a fusion polypeptide-specific antibody. In another preferred embodiment, the fusion polypeptide-specific reagent comprises a heavy-isotope labeled phosphopeptide (AQUA peptide) corresponding to the fusion junction of SLC34A2-ROS fusion polypeptide (see FIG. 7 (bottom panel)).

The methods of the invention described above may also optionally comprise the step of determining the level of expression or activation of other kinases, such as wild type ROS and EGFR, or other downstream signaling molecules in said biological sample. Profiling both SLC34A2-ROS fusion polypeptide expression/activation and expression/activation of other kinases and pathways in a given biological sample can provide valuable information on which kinase(s) and pathway(s) is/are driving the disease, and which therapeutic regime is therefore likely to be of most benefit.

Compound Screening.

The discovery of the novel SLC34A2-ROS fusion polypeptides described herein also enables the development of new compounds that inhibit the activity of these mutant ROS proteins, particularly their ROS kinase activity. Accordingly, the invention also provides, in part, a method for determining whether a compound inhibits the progression of a cancer characterized by a SLC34A2-ROS fusion polynucleotide and/or polypeptide, said method comprising the step of determining whether said compound inhibits the expression and/or activity of said SLC34A2-ROS fusion polypeptide in said cancer. In one preferred embodiment, inhibition of expression and/or activity of the SLC34A2-ROS fusion polypeptide is determined using at least one reagent that detects a mutant ROS polynucleotide and/or mutant ROS polypeptide of the invention. Preferred reagents of the invention have been described above. Compounds suitable for the inhibition of ROS kinase activity are described in more detail in Section G below.

The compound may, for example, be a kinase inhibitor, such as a small molecule or antibody inhibitor. It may be a pan-kinase inhibitor with activity against several different kinases, or a kinase-specific inhibitor. ROS kinase-inhibiting compounds are discussed in further detail in Section G below. Patient biological samples may be taken before and after treatment with the inhibitor and then analyzed, using methods described above, for the biological effect of the inhibitor on ROS kinase activity, including the phosphorylation of downstream substrate protein. Such a pharmacodynamic assay may be useful in determining the biologically active dose of the drug that may be preferable to a maximal tolerable dose. Such information would also be useful in submissions for drug approval by demonstrating the mechanism of drug action. Identifying compounds with such desired inhibitory characteristics is further described in Section G below.

G. Therapeutic Inhibition of Cancers.

In accordance with the present invention, it has now been shown that the SLC34A2-ROS fusion polypeptide occurs in at least one subgroup of human NSCLC. Accordingly, the progression of a mammalian cancer (e.g. NSCLC) in which SLC34A2-ROS fusion protein is expressed may be inhibited, in vivo, by inhibiting the activity of ROS kinase in such cancer. ROS activity in cancers characterized by expression of a mutant ROS kinase may be inhibited by contacting the cancer (e.g. a tumor) with a ROS kinase-inhibiting therapeutic. Accordingly, the invention provides, in part, a method for inhibiting the progression of a SLC34A2-ROS fusion polypeptide-expressing cancer by inhibiting the expression and/or activity of ROS kinase in the cancer.

A ROS kinase-inhibiting therapeutic may be any composition comprising at least one compound, biological or chemical, which inhibits, directly or indirectly, the expression and/or activity of ROS kinase in vivo, including the exemplary classes of compounds described below. Such compounds include therapeutics that act directly on ROS kinase itself, or on proteins or molecules that modify the activity of ROS, or that act indirectly by inhibiting the expression of ROS. Such compositions also include compositions comprising only a single ROS kinase inhibiting compound, as well as compositions comprising multiple therapeutics (including those against other RTKs), which may also include a non-specific therapeutic agent like a chemotherapeutic agent or general transcription inhibitor.

Small-Molecule Inhibitors.

In some preferred embodiments, a ROS-inhibiting therapeutic useful in the practice of the methods of the invention is a targeted, small molecule inhibitor. Small molecule targeted inhibitors are a class of molecules that typically inhibit the activity of their target enzyme by specifically, and often irreversibly, binding to the catalytic site of the enzyme, and/or binding to an ATP-binding cleft or other binding site within the enzyme that prevents the enzyme from adopting a conformation necessary for its activity. An exemplary small-molecule targeted kinase inhibitor is Gleevec® (Imatinib, STI-571), which inhibits CSF1R and BCR-ABL, and its properties have been well described. See Dewar et al., *Blood* 105(8): 3127-32 (2005).

Small molecule inhibitors may be rationally designed using X-ray crystallographic or computer modeling of ROS kinase three-dimensional structure, or may found by high throughput screening of compound libraries for inhibition of ROS. Such methods are well known in the art, and have been described. Specificity of ROS inhibition may be confirmed, for example, by examining the ability of such compound to inhibit ROS activity, but not other kinase activity, in a panel of kinases, and/or by examining the inhibition of ROS activity in a biological sample comprising NSCLC tumor cells, as described above. Such screening methods are further described below.

Antibody Inhibitors.

ROS kinase-inhibiting therapeutics useful in the methods of the invention may also be targeted antibodies that specifically bind to critical catalytic or binding sites or domains required for ROS activity, and inhibit the kinase by blocking access of ligands, substrates or secondary molecules to a and/or preventing the enzyme from adopting a conformation necessary for its activity. The production, screening, and therapeutic use of humanized target-specific antibodies has been well-described. See Merluzzi et al., *Adv Clin Path.* 4(2): 77-85 (2000). Commercial technologies and systems, such as Morphosys, Inc.'s Human Combinatorial Antibody Library (HuCAL®), for the high-throughput generation and screening of humanized target-specific inhibiting antibodies are available.

The production of various anti-receptor kinase targeted antibodies and their use to inhibit activity of the targeted receptor has been described. See, e.g. U.S. Patent Publication No. 20040202655, "Antibodies to IGF-I Receptor for the Treatment of Cancers," Oct. 14, 2004, Morton et al.; U.S. Patent Publication No. 20040086503, "Human anti-Epidermal Growth Factor Receptor Single-Chain Antibodies," Apr. 15, 2004, Raisch et al.; U.S. Patent Publication No. 20040033543, "Treatment of Renal Carcinoma Using Antibodies Against the EGFr," Feb. 19, 2004, Schwab et. al. Standardized methods for producing, and using, receptor tyrosine kinase activity-inhibiting antibodies are known in the art. See, e.g., European Patent No. EP1423428, "Antibodies that Block Receptor Tyrosine Kinase Activation, Methods of Screening for and Uses Thereof," Jun. 2, 2004, Borges et al.

Phage display approaches may also be employed to generate ROS-specific antibody inhibitors, and protocols for bacteriophage library construction and selection of recombinant antibodies are provided in the well-known reference text CURRENT PROTOCOLS IN IMMUNOLOGY, Colligan et al. (Eds.), John Wiley & Sons, Inc. (1992-2000), Chapter 17, Section 17.1. See also U.S. Pat. No. 6,319,690, Nov. 20, 2001, Little et al.; U.S. Pat. No. 6,300,064, Oct. 9, 2001, Knappik et al.; U.S. Pat. No. 5,840,479, Nov. 24, 1998, Little et al.; U.S. Patent Publication No. 20030219839, Nov. 27, 2003, Bowdish et al.

A library of antibody fragments displayed on the surface of bacteriophages may be produced (see, e.g. U.S. Pat. No. 6,300,064, Oct. 9, 2001, Knappik et al.) and screened for binding to a soluble dimeric form of a receptor protein tyrosine kinase (like ROS). An antibody fragment that binds to the soluble dimeric form of the RTK used for screening is identified as a candidate molecule for blocking constitutive activation of the target RTK in a cell. See European Patent No. EP1423428, Borges et al., supra.

ROS-binding targeted antibodies identified in screening of antibody libraries as describe above may then be further screened for their ability to block the activity of ROS, both in vitro kinase assay and in vivo in cell lines and/or tumors. ROS inhibition may be confirmed, for example, by examining the ability of such antibody therapeutic to inhibit ROS kinase activity, but not other kinase activity, in a panel of kinases, and/or by examining the inhibition of ROS activity in a biological sample comprising cancer cells, as described above. Methods for screening such compounds for ROS kinase inhibition are further described above.

Indirect Inhibitors.

ROS-inhibiting compounds useful in the practice of the disclosed methods may also be compounds that indirectly inhibit ROS activity by inhibiting the activity of proteins or molecules other than ROS kinase itself. Such inhibiting therapeutics may be targeted inhibitors that modulate the activity of key regulatory kinases that phosphorylate or de-phosphorylate (and hence activate or deactivate) ROS itself, or interfere with binding of ligands. As with other receptor tyrosine kinases, ROS regulates downstream signaling through a network of adaptor proteins and downstream kinases. As a result, induction of cell growth and survival by ROS activity may be inhibited by targeting these interacting or downstream proteins.

ROS kinase activity may also be indirectly inhibited by using a compound that inhibits the binding of an activating molecule necessary for ROS to adopt its active conformation. For example, the production and use of anti-PDGF antibodies has been described. See U.S. Patent Publication No. 20030219839, "Anti-PDGF Antibodies and Methods for Producing Engineered Antibodies," Bowdish et al. Inhibition of ligand (PDGF) binding to the receptor directly down-regulates the receptor activity.

Indirect inhibitors of ROS activity may be rationally designed using X-ray crystallographic or computer modeling of ROS three dimensional structure, or may found by high throughput screening of compound libraries for inhibition of key upstream regulatory enzymes and/or necessary binding molecules, which results in inhibition of ROS kinase activity. Such approaches are well known in the art, and have been described. ROS inhibition by such therapeutics may be confirmed, for example, by examining the ability of the compound to inhibit ROS activity, but not other kinase activity, in a panel of kinases, and/or by examining the inhibition of ROS activity in a biological sample comprising cancer cells, e.g. NSCLC cells, as described above. Methods for identifying compounds that inhibit a cancer characterized by a SLC34A2-ROS translocation and/or fusion polypeptide, and/or truncated ROS polynucleotide and/or polypeptide, are further described below.

Anti-Sense and/or Transcription Inhibitors.

ROS inhibiting therapeutics may also comprise anti-sense and/or transcription inhibiting compounds that inhibit ROS kinase activity by blocking transcription of the gene encoding ROS and/or the SLC34A2-ROS fusion gene. The inhibition of various receptor kinases, including VEGFR, EGFR, and IGFR, and FGFR, by antisense therapeutics for the treatment of cancer has been described. See, e.g., U.S. Pat. Nos. 6,734,017; 6, 710,174, 6,617,162; 6,340,674; 5,783,683; 5,610, 288.

Antisense oligonucleotides may be designed, constructed, and employed as therapeutic agents against target genes in accordance with known techniques. See, e.g. Cohen, J., *Trends in Pharmacol. Sci.* 10(11): 435-437 (1989); Marcus-Sekura, *Anal. Biochem.* 172: 289-295 (1988); Weintraub, H., *Sci. AM.* pp. 40-46 (1990); Van Der Krol et al., *Bio Techniques* 6(10): 958-976 (1988); Skorski et al., *Proc. Natl. Acad. Sci. USA* (1994) 91: 4504-4508. Inhibition of human carcinoma growth in vivo using an antisense RNA inhibitor of EGFR has recently been described. See U.S. Patent Publication No. 20040047847, "Inhibition of Human Squamous Cell Carcinoma Growth In vivo by Epidermal Growth Factor Receptor Antisense RNA Transcribed from a Pol III Promoter," Mar. 11, 2004, He et al. Similarly, a ROS-inhibiting therapeutic comprising at least one antisense oligonucleotide against a mammalian ROS gene (see FIG. 4 (SEQ ID NO: 8) or SLC34A2-ROS fusion polynucleotide or truncated ROS polynucleotide (see FIG. 2 (SEQ ID NOs: 2 or 4) or truncated may be prepared according to methods described above. Pharmaceutical compositions comprising ROS-inhibiting antisense compounds may be prepared and administered as further described below.

Small Interfering RNA.

Small interfering RNA molecule (siRNA) compositions, which inhibit translation, and hence activity, of ROS through the process of RNA interference, may also be desirably employed in the methods of the invention. RNA interference, and the selective silencing of target protein expression by introduction of exogenous small double-stranded RNA molecules comprising sequence complimentary to mRNA encoding the target protein, has been well described. See, e.g. U.S. Patent Publication No. 20040038921, "Composition and Method for Inhibiting Expression of a Target Gene," Feb. 26, 2004, Kreutzer et al.; U.S. Patent Publication No. 20020086356, "RNA Sequence-Specific Mediators of RNA Interference," Jun. 12, 2003, Tuschl et al.; U.S. Patent Publication 20040229266, "RNA Interference Mediating Small RNA Molecules," Nov. 18, 2004, Tuschl et. al.

For example, as described in Example 3, siRNA-mediated silencing of expression of the SLC34A2-ROS fusion protein may be effected in a human NSCLC cell line expressing the fusion protein.

Double-stranded RNA molecules (dsRNA) have been shown to block gene expression in a highly conserved regulatory mechanism known as RNA interference (RNAi). Briefly, the RNAse III Dicer processes dsRNA into small interfering RNAs (siRNA) of approximately 22 nucleotides, which serve as guide sequences to induce target-specific mRNA cleavage by an RNA-induced silencing complex RISC (see Hammond et al., *Nature* (2000) 404: 293-296). RNAi involves a catalytic-25° type reaction whereby new siRNAs are generated through successive cleavage of longer dsRNA. Thus, unlike antisense, RNAi degrades target RNA in a non-stoichiometric manner. When administered to a cell or organism, exogenous dsRNA has been shown to direct the sequence-specific degradation of endogenous messenger RNA (mRNA) through RNAi.

A wide variety of target-specific siRNA products, including vectors and systems for their expression and use in mammalian cells, are now commercially available. See, e.g. Promega, Inc. (www.promega.com); Dharmacon, Inc. (www.dharmacon.com). Detailed technical manuals on the design, construction, and use of dsRNA for RNAi are available. See, e.g. Dharmacon's "RNAi Technical Reference & Application Guide"; Promega's "RNAi: A Guide to Gene Silencing." ROS-inhibiting siRNA products are also commercially available, and may be suitably employed in the method of the invention. See, e.g. Dharmacon, Inc., Lafayette, Colo. (Cat Nos. M-003162-03, MU-003162-03, D-003162-07 thru -10 (siGENOME™ SMARTselection and SMARTpool® siRNAs).

It has recently been established that small dsRNA less than 49 nucleotides in length, and preferably 19-25 nucleotides, comprising at least one sequence that is substantially identical to part of a target mRNA sequence, and which dsRNA optimally has at least one overhang of 1-4 nucleotides at an end, are most effective in mediating RNAi in mammals. See U.S. Patent Publication No. 20040038921, Kreutzer et al., supra; U.S. Patent Publication No. 20040229266, Tuschl et al., supra. The construction of such dsRNA, and their use in pharmaceutical preparations to silence expression of a target protein, in vivo, are described in detail in such publications.

If the sequence of the gene to be targeted in a mammal is known, 21-23 nt RNAs, for example, can be produced and tested for their ability to mediate RNAi in a mammalian cell, such as a human or other primate cell. Those 21-23 nt RNA molecules shown to mediate RNAi can be tested, if desired, in an appropriate animal model to further assess their in vivo effectiveness. Target sites that are known, for example target sites determined to be effective target sites based on studies with other nucleic acid molecules, for example ribozymes or antisense, or those targets known to be associated with a disease or condition such as those sites containing mutations or deletions, can be used to design siRNA molecules targeting those sites as well.

Alternatively, the sequences of effective dsRNA can be rationally designed/predicted screening the target mRNA of interest for target sites, for example by using a computer folding algorithm. The target sequence can be parsed in silico into a list of all fragments or subsequences of a particular length, for example 23 nucleotide fragments, using a custom Perl script or commercial sequence analysis programs such as Oligo, MacVector, or the GCG Wisconsin Package.

Various parameters can be used to determine which sites are the most suitable target sites within the target RNA sequence. These parameters include but are not limited to secondary or tertiary RNA structure, the nucleotide base composition of the target sequence, the degree of homology between various regions of the target sequence, or the relative position of the target sequence within the RNA transcript. Based on these determinations, any number of target sites within the RNA transcript can be chosen to screen siRNA molecules for efficacy, for example by using in vitro RNA cleavage assays, cell culture, or animal models. See, e.g., U.S. Patent Publication No. 20030170891, Sep. 11, 2003, McSwiggen J. An algorithm for identifying and selecting RNAi target sites has also recently been described. See U.S. Patent Publication No. 20040236517, "Selection of Target Sites for Antisense Attack of RNA," Nov. 25, 2004, Drlica et al.

Commonly used gene transfer techniques include calcium phosphate, DEAE-dextran, electroporation and microinjection and viral methods (Graham et al. (1973) *Virol.* 52: 456; McCutchan et al., (1968), *J. Natl. Cancer Inst.* 41: 351; Chu et al. (1987), *Nucl. Acids Res.* 15: 1311; Fraley et al. (1980), *J. Biol. Chem.* 255: 10431; Capecchi (1980), *Cell* 22: 479). DNA may also be introduced into cells using cationic liposomes (Feigner et al. (1987), *Proc. Natl. Acad. Sci. USA* 84: 7413). Commercially available cationic lipid formulations include Tfx 50 (Promega) or Lipofectamin 200 (Life Technologies). Alternatively, viral vectors may be employed to deliver dsRNA to a cell and mediate RNAi. See U.S. Patent Publication No. 20040023390, "siRNA-mediated Gene Silencing with Viral Vectors," Feb. 4, 2004, Davidson et al.

Transfection and vector/expression systems for RNAi in mammalian cells are commercially available and have been well described. See, e.g. Dharmacon, Inc., DharmaFECT™ system; Promega, Inc., siSTRIKE™ U6 Hairpin system; see also Gou et al. (2003) *FEBS.* 548, 113-118; Sui, G. et al. A DNA vector-based RNAi technology to suppress gene expression in mammalian cells (2002) *Proc. Natl. Acad. Sci.* 99, 5515-5520; Yu et al. (2002) *Proc. Natl. Acad. Sci.* 99, 6047-6052; Paul, C. et al. (2002) *Nature Biotechnology* 19, 505-508; McManus et al. (2002) *RNA* 8, 842-850.

siRNA interference in a mammal using prepared dsRNA molecules may then be effected by administering a pharmaceutical preparation comprising the dsRNA to the mammal. The pharmaceutical composition is administered in a dosage sufficient to inhibit expression of the target gene. dsRNA can typically be administered at a dosage of less than 5 mg dsRNA per kilogram body weight per day, and is sufficient to inhibit or completely suppress expression of the target gene. In general a suitable dose of dsRNA will be in the range of 0.01 to 2.5 milligrams per kilogram body weight of the recipient per day, preferably in the range of 0.1 to 200 micrograms per kilogram body weight per day, more preferably in the range of 0.1 to 100 micrograms per kilogram body weight per day, even more preferably in the range of 1.0 to 50 micrograms per kilogram body weight per day, and most preferably in the range of 1.0 to 25 micrograms per kilogram body weight per day. A pharmaceutical composition comprising the dsRNA is administered once daily, or in multiple sub-doses, for example, using sustained release formulations well known in the art. The preparation and administration of such pharmaceutical compositions may be carried out accordingly to standard techniques, as further described below.

Such dsRNA may then be used to inhibit ROS expression and activity in a cancer, by preparing a pharmaceutical preparation comprising a therapeutically-effective amount of such dsRNA, as described above, and administering the preparation to a human subject having a cancer expressing SLC34A2-ROS fusion protein or truncated ROS kinase polypeptide, for example, via direct injection to the tumor. The similar inhibition of other receptor tyrosine kinases, such as VEGFR and EGFR using siRNA inhibitors has recently been described. See U.S. Patent Publication No. 20040209832, Oct. 21, 2004, McSwiggen et al.; U.S. Patent Publication No. 20030170891, Sep. 11, 2003, McSwiggen; U.S. Patent Publication No. 20040175703, Sep. 9, 2004, Kreutzer et al.

Therapeutic Compositions; Administration.

ROS kinase-inhibiting therapeutic compositions useful in the practice of the methods of the invention may be administered to a mammal by any means known in the art including, but not limited to oral or peritoneal routes, including intravenous, intramuscular, intraperitoneal, subcutaneous, transdermal, airway (aerosol), rectal, vaginal and topical (including buccal and sublingual) administration.

For oral administration, a ROS-inhibiting therapeutic will generally be provided in the form of tablets or capsules, as a powder or granules, or as an aqueous solution or suspension. Tablets for oral use may include the active ingredients mixed with pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

Capsules for oral use include hard gelatin capsules in which the active ingredient is mixed with a solid diluent, and soft gelatin capsules wherein the active ingredients is mixed with water or an oil such as peanut oil, liquid paraffin or olive oil. For intramuscular, intraperitoneal, subcutaneous and intravenous use, the pharmaceutical compositions of the invention will generally be provided in sterile aqueous solutions or suspensions, buffered to an appropriate pH and isotonicity. Suitable aqueous vehicles include Ringer's solution and isotonic sodium chloride. The carrier may consists exclusively of an aqueous buffer ("exclusively" means no auxiliary agents or encapsulating substances are present which might affect or mediate uptake of the ROS-inhibiting therapeutic). Such substances include, for example, micellar structures, such as liposomes or capsids, as described below. Aqueous suspensions may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

ROS kinase-inhibiting therapeutic compositions may also include encapsulated formulations to protect the therapeutic (e.g. a dsRNA compound) against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811; PCT publication WO 91/06309; and European patent publication EP-A-43075. An encapsulated formulation may comprise a viral coat protein. The viral coat protein may be derived from or associated with a virus, such as a polyoma virus, or it may be partially or entirely artificial. For example, the coat protein may be a Virus Protein 1 and/or Virus Protein 2 of the polyoma virus, or a derivative thereof.

ROS-inhibiting compositions can also comprise a delivery vehicle, including liposomes, for administration to a subject, carriers and diluents and their salts, and/or can be present in pharmaceutically acceptable formulations. For example, methods for the delivery of nucleic acid molecules are described in Akhtar et al., 1992, *Trends Cell Bio.*, 2, 139; DELIVERY STRATEGIES FOR ANTISENSE OLIGONUCLEOTIDE THERAPEUTICS, ed. Akbtar, 1995, Maurer et al., 1999, *Mol. Membr. Biol.*, 16, 129-140; Hofland and Huang, 1999, *Handb. Exp. Pharmacol.*, 137, 165-192; and Lee et al., 2000, ACS Symp. Ser., 752, 184-192. Beigelman et al., U.S. Pat. No. 6,395,713 and Sullivan et al., PCT WO 94/02595 further describe the general methods for delivery of nucleic acid molecules. These protocols can be utilized for the delivery of virtually any nucleic acid molecule.

ROS-inhibiting therapeutics can be administered to a mammalian tumor by a variety of methods known to those of skill in the art, including, but not restricted to, encapsulation in liposomes, by iontophoresis, or by incorporation into other vehicles, such as hydrogels, cyclodextrins, biodegradable nanocapsules, and bioadhesive microspheres, or by proteinaceous vectors (O'Hare and Normand, International PCT Publication No. WO 00/53722). Alternatively, the therapeutic/vehicle combination is locally delivered by direct injection or by use of an infusion pump. Direct injection of the composition, whether subcutaneous, intramuscular, or intradermal, can take place using standard needle and syringe methodologies, or by needle-free technologies such as those described in Conry et al., 1999, *Clin. Cancer Res.*, 5, 2330-2337 and Barry et al., International PCT Publication No. WO 99/31262.

Pharmaceutically acceptable formulations of ROS kinase-inhibitory therapeutics include salts of the above described compounds, e.g., acid addition salts, for example, salts of hydrochloric, hydrobromic, acetic acid, and benzene sulfonic acid. A pharmacological composition or formulation refers to a composition or formulation in a form suitable for administration, e.g., systemic administration, into a cell or patient, including for example a human. Suitable forms, in part, depend upon the use or the route of entry, for example oral, transdermal, or by injection. Such forms should not prevent the composition or formulation from reaching a target cell. For example, pharmacological compositions injected into the blood stream should be soluble. Other factors are known in the art, and include considerations such as toxicity and forms that prevent the composition or formulation from exerting its effect.

Administration routes that lead to systemic absorption (i.e. systemic absorption or accumulation of drugs in the blood stream followed by distribution throughout the entire body), are desirable and include, without limitation: intravenous, subcutaneous, intraperitoneal, inhalation, oral, intrapulmonary and intramuscular. Each of these administration routes exposes the ROS-inhibiting therapeutic to an accessible diseased tissue or tumor. The rate of entry of a drug into the circulation has been shown to be a function of molecular weight or size. The use of a liposome or other drug carrier comprising the compounds of the instant invention can potentially localize the drug, for example, in certain tissue types, such as the tissues of the reticular endothelial system (RES). A liposome formulation that can facilitate the association of drug with the surface of cells, such as, lymphocytes and macrophages is also useful. This approach can provide enhanced delivery of the drug to target cells by taking advantage of the specificity of macrophage and lymphocyte immune recognition of abnormal cells, such as cancer cells.

By "pharmaceutically acceptable formulation" is meant, a composition or formulation that allows for the effective distribution of the nucleic acid molecules of the instant invention in the physical location most suitable for their desired activity. Nonlimiting examples of agents suitable for formulation with the nucleic acid molecules of the instant invention include: P-glycoprotein inhibitors (such as Pluronic P85), which can enhance entry of drugs into the CNS (Jolliet-Riant and Tillement, 1999, *Fundam. Clin. Pharmacol.*, 13, 16-26); biodegradable polymers, such as poly (DL-lactide-coglycolide) microspheres for sustained release delivery after intracerebral implantation (Emerich et al, 1999, *Cell Transplant*, 8, 47-58) (Alkermes, Inc. Cambridge, Mass.); and loaded nanoparticles, such as those made of polybutylcyanoacrylate, which can deliver drugs across the blood brain barrier and can alter neuronal uptake mechanisms (*Prog Neuro-psychopharmacol Biol Psychiatry*, 23, 941-949, 1999). Other non-limiting examples of delivery strategies for the ROS-inhibiting compounds useful in the method of the invention include material described in Boado et al., 1998, *J. Pharm. Sci.*, 87, 1308-1315; Tyler et al., 1999, *FEBS Lett.*, 421, 280-284; Pardridge et al., 1995, *PNAS USA.*, 92, 5592-5596; Boado, 1995, *Adv. Drug Delivery Rev.*, 15, 73-107; Aldrian-Herrada et al., 1998, *Nucleic Acids Res.*, 26, 4910-4916; and Tyler et al., 1999, *PNAS USA.*, 96, 7053-7058.

Therapeutic compositions comprising surface-modified liposomes containing poly (ethylene glycol) lipids (PEG-modified, or long-circulating liposomes or stealth liposomes) may also be suitably employed in the methods of the invention. These formulations offer a method for increasing the accumulation of drugs in target tissues. This class of drug carriers resists opsonization and elimination by the mononuclear phagocytic system (MPS or RES), thereby enabling longer blood circulation times and enhanced tissue exposure for the encapsulated drug (Lasic et al. Chem. Rev. 1995, 95, 2601-2627; Ishiwata et al., Chem. Pharm. Bull. 1995, 43, 1005-1011). Such liposomes have been shown to accumulate selectively in tumors, presumably by extravasation and capture in the neovascularized target tissues (Lasic et al., Science 1995, 267, 1275-1276; Oku et al., 1995, Biochim. Biophys. Acta, 1238, 86-90). The long-circulating liposomes enhance the pharmacokinetics and pharmacodynamics of DNA and RNA, particularly compared to conventional cationic liposomes which are known to accumulate in tissues of the MPS (Liu et al., J. Biol. Chem. 1995, 42, 24864-24870; Choi et al., International PCT Publication No. WO 96/10391; Ansell et al., International PCT Publication No. WO 96/10390; Holland et al., International PCT Publication No. WO 96/10392). Long-circulating liposomes are also likely to protect drugs from nuclease degradation to a greater extent compared to cationic liposomes, based on their ability to avoid accumulation in metabolically aggressive MPS tissues such as the liver and spleen.

Therapeutic compositions may include a pharmaceutically effective amount of the desired compounds in a pharmaceutically acceptable carrier or diluent. Acceptable carriers or diluents for therapeutic use are well known in the pharmaceutical art, and are described, for example, in REMINGTON'S PHARMACEUTICAL SCIENCES, Mack Publishing Co. (A. R. Gennaro edit. 1985). For example, preservatives, stabilizers, dyes and flavoring agents can be provided. These include sodium benzoate, sorbic acid and esters of p-hydroxybenzoic acid. In addition, antioxidants and suspending agents can be used.

A pharmaceutically effective dose is that dose required to prevent, inhibit the occurrence, or treat (alleviate a symptom to some extent, preferably all of the symptoms) of a disease state. The pharmaceutically effective dose depends on the type of disease, the composition used, the route of administration, the type of mammal being treated, the physical characteristics of the specific mammal under consideration, concurrent medication, and other factors that those skilled in the medical arts will recognize. Generally, an amount between 0.1 mg/kg and 100 mg/kg body weight/day of active ingredients is administered dependent upon potency of the negatively charged polymer.

Dosage levels of the order of from about 0.1 mg to about 140 mg per kilogram of body weight per day are useful in the treatment of the above-indicated conditions (about 0.5 mg to about 7 g per patient per day). The amount of active ingredient that can be combined with the carrier materials to produce a single dosage form varies depending upon the host treated and the particular mode of administration. Dosage unit forms generally contain between from about 1 mg to about 500 mg of an active ingredient. It is understood that the specific dose level for any particular patient depends upon a variety of factors including the activity of the specific compound employed, the age, body weight, general health, sex, diet, time of administration, route of administration, and rate of excretion, drug combination and the severity of the particular disease undergoing therapy.

For administration to non-human animals, the composition can also be added to the animal feed or drinking water. It can be convenient to formulate the animal feed and drinking water compositions so that the animal takes in a therapeutically appropriate quantity of the composition along with its diet. It can also be convenient to present the composition as a premix for addition to the feed or drinking water.

A ROS-inhibiting therapeutic useful in the practice of the invention may comprise a single compound as described above, or a combination of multiple compounds, whether in the same class of inhibitor (i.e. antibody inhibitor), or in different classes (i.e antibody inhibitors and small-molecule inhibitors). Such combination of compounds may increase the overall therapeutic effect in inhibiting the progression of a fusion protein-expressing cancer. For example, the therapeutic composition may a small molecule inhibitor, such as STI-571 (Gleevec®) alone, or in combination with other Gleevec® analogues targeting ROS activity and/or small molecule inhibitors of EGFR, such as Tarceva™ or Iressa™. The therapeutic composition may also comprise one or more non-specific chemotherapeutic agent in addition to one or more targeted inhibitors. Such combinations have recently been shown to provide a synergistic tumor killing effect in many cancers. The effectiveness of such combinations in inhibiting ROS activity and tumor growth in vivo can be assessed as described below.

Identification of Mutant ROS Kinase-Inhibiting Compounds.

The invention also provides, in part, a method for determining whether a compound inhibits the progression of a cancer characterized by a SLC34A2-ROS translocation and/or fusion polypeptide, by determining whether the compound inhibits the activity of SLC34A2-ROS fusion polypeptide in the cancer. In some preferred embodiments, inhibition of activity of ROS is determined by examining a biological sample comprising cells from bone marrow, blood, or a tumor. In another preferred embodiment, inhibition of activity of ROS is determined using at least one mutant ROS polynucleotide or polypeptide-specific reagent of the invention.

The tested compound may be any type of therapeutic or composition as described above. Methods for assessing the efficacy of a compound, both in vitro and in vivo, are well established and known in the art. For example, a composition may be tested for ability to inhibit ROS in vitro using a cell or cell extract in which ROS kinase is activated. A panel of compounds may be employed to test the specificity of the compound for ROS (as opposed to other targets, such as EGFR or PDGFR).

Another technique for drug screening which may be used provides for high throughput screening of compounds having suitable binding affinity to a protein of interest, as described in published PCT application WO84/03564. In this method, as applied to mutant ROS polypeptides, large numbers of different small test, compounds are synthesized on a solid substrate, such as plastic pins or some other surface. The test compounds are reacted with mutant ROS polypeptide, or fragments thereof, and washed. Bound mutant polypeptide (e.g. SLC34A2-ROS fusion polypeptide) is then detected by methods well known in the art. Purified mutant ROS polypeptide can also be coated directly onto plates for use in the aforementioned drug screening techniques. Alternatively, non-neutralizing antibodies can be used to capture the peptide and immobilize it on a solid support.

A compound found to be an effective inhibitor of ROS activity in vitro may then be examined for its ability to inhibit the progression of a cancer expressing SLC34A2-ROS fusion polypeptide, in vivo, using, for example, mammalian xenografts harboring human NSCLC tumors that are driven by SLC34A2-ROS fusion protein. In this procedure, cell lines known to be driven by SLC34A2-ROS fusion protein are placed subcutaneously in the mouse. The cells then grow into a tumor mass that may be visually monitored. The mouse may then be treated with the drug. The effect of the drug treatment on tumor size may be externally observed. The mouse is then sacrificed and the tumor removed for analysis by IHC and Western blot. Similarly, mammalian bone marrow transplants may be prepared, by standard methods, to examine drug response in hematological tumors expressing a mutant ROS kinase. In this way, the effects of the drug may be observed in a biological setting most closely resembling a patient. The drug's ability to alter signaling in the tumor cells or surrounding stromal cells may be determined by analysis with phosphorylation-specific antibodies. The drug's effectiveness in inducing cell death or inhibition of cell proliferation may also be observed by analysis with apoptosis specific markers such as cleaved caspase 3 and cleaved PARP.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred.

The teachings of all references cited above and below are hereby incorporated herein by reference. The following Examples are provided only to further illustrate the invention, and are not intended to limit its scope, except as provided in the claims appended hereto. The present invention encompasses modifications and variations of the methods taught herein which would be obvious to one of ordinary skill in the art.

EXAMPLE 1

Identification of ROS Kinase Activity in an NSCLC Cell Line by Global Phosphopeptide Profiling The global phosphorylation profile of kinase activation in several human NSCLC cell lines, including HCC78, were examined using a recently described and powerful technique for the isolation and mass spectrometric characterization of modified peptides from complex mixtures (the "IAP" technique, see Rush et al., supra). The IAP technique was performed using a phosphotyrosine-specific antibody (CELL SIGNALING TECHNOLOGY, INC., Beverly, Mass., 2003/04 Cat. #9411) to isolate, and subsequently characterize, phosphotyrosine-containing peptides from extracts of the NSCLC cell lines.

Specifically, the IAP approach was employed go facilitate the identification of activated tyrosine kinases in the NSCLC cell lines, in order to identify novel drivers of this disease.
Cell Culture.

HCC78 cells were obtained from DSMZ (the German National Resource Centre for Biological Material), grown in RPMI-1640 medium (Invitrogen) with 10% fetal bovine serum (FBS) (Sigma).
Phosphopeptide Immunoprecipitation.

A total of $2 \times 10^8$ cells were lysed in urea lysis buffer (20 mM HEPES pH 8.0, 9M urea, 1 mM sodium vanadate, 2.5 mM sodium pyrophosphate, 1 mM beta-glycerophosphate) at $1.25 \times 10^8$ cells/ml and sonicated. Sonicated lysates were cleared by centrifugation at 20,000×g, and proteins were reduced and alkylated as described previously (see Rush et al., Nat. Biotechnol. 23(1): 94-101 (2005)). Samples were diluted with 20 mM HEPES pH 8.0 to a final urea concentration of 2M. Trypsin (1 mg/ml in 0.001 M HCl) was added to the clarified lysate at 1:100 v/v. Samples were digested overnight at room temperature.

Following digestion, lysates were acidified to a final concentration of 1% TFA. Peptide purification was carried out using Sep-Pak $C_{18}$ columns as described previously (see Rush et al., supra.). Following purification, all elutions (8%, 12%, 15%, 18%, 22%, 25%, 30%, 35% and 40% acetonitrile in 0.1% TFA) were combined and lyophilized. Dried peptides were resuspended in 1.4 ml MOPS buffer (50 mM MOPS/NaOH pH 7.2, 10 mM $Na_2HPO_4$, 50 mM NaCl) and insoluble material removed by centrifugation at 12,000×g for 10 minutes.

The phosphotyrosine monoclonal antibody P-Tyr-100 (Cell Signaling Technology) from ascites fluid was coupled non-covalently to protein G agarose beads (Roche) at 4 mg/ml beads overnight at 4° C. After coupling, antibody-resin was washed twice with PBS and three times with MOPS buffer. Immobilized antibody (40 µl, 160 µg) was added as a 1:1 slurry in MOPS IP buffer to the solubilized peptide fraction, and the mixture was incubated overnight at 4° C. The immobilized antibody beads were washed three times with MOPS buffer and twice with $ddH_2O$. Peptides were eluted twice from beads by incubation with 40 µl of 0.1% TFA for 20 minutes each, and the fractions were combined.
Analysis by LC-MS/MS Mass Spectrometry.

Peptides in the IP eluate (40 µl) were concentrated and separated from eluted antibody using Stop and Go extraction tips (StageTips) (see Rappsilber et al., Anal. Chem., 75(3): 663-70 (2003)). Peptides were eluted from the microcolumns with 1 µl of 60% MeCN, 0.1% TFA into 7.6 µl of 0.4% acetic acid/0.005% heptafluorobutyric acid (HFBA). The sample was loaded onto a 10 cm×75 µm PicoFrit capillary column (New Objective) packed with Magic C18 AQ reversed-phase resin (Michrom Bioresources) using a Famos autosampler with an inert sample injection valve (Dionex). The column was developed with a 45-min linear gradient of acetonitrile in 0.4% acetic acid, 0.005% HFBA delivered at 280 nl/min (Ultimate, Dionex).

Tandem mass spectra were collected in a data-dependent manner with an LCQ Deca XP Plus ion trap mass spectrometer (ThermoFinnigan), using a top-four method, a dynamic exclusion repeat count of 1, and a repeat duration of 0.5 min.
Database Analysis & Assignments.

MS/MS spectra were evaluated using TurboSequest (ThermoFinnigan) (in the Sequest Browser package (v. 27, rev. 12) supplied as part of BioWorks 3.0). Individual MS/MS spectra were extracted from the raw data file using the Sequest Browser program CreateDta, with the following settings: bottom MW, 700; top MW, 4,500; minimum number of ions, 20; minimum TIC, $4 \times 10^5$; and precursor charge state, unspecified. Spectra were extracted from the beginning of the raw data file before sample injection to the end of the eluting gradient. The IonQuest and VuDta programs were not used to further select MS/MS spectra for Sequest analysis. MS/MS spectra were evaluated with the following TurboSequest parameters: peptide mass tolerance, 2.5; fragment ion tolerance, 0.0; maximum number of differential amino acids per modification, 4; mass type parent, average; mass type fragment, average; maximum number of internal cleavage sites, 10; neutral losses of water and ammonia from b and y ions were considered in the correlation analysis. Proteolytic enzyme was specified except for spectra collected from elastase digests.

Searches were done against the NCBI human database released on Aug. 24, 2004 containing 27,175 proteins allowing oxidized methionine (M+16) and phosphorylation (Y+80) as dynamic modifications.

In proteomics research, it is desirable to validate protein identifications based solely on the observation of a single peptide in one experimental result, in order to indicate that the protein is, in fact, present in a sample. This has led to the development of statistical methods for validating peptide assignments, which are not yet universally accepted, and guidelines for the publication of protein and peptide identification results (see Carr et al., *Mol. Cell. Proteomics* 3: 531-533 (2004)), which were followed in this Example. However, because the immunoaffinity strategy separates phosphorylated peptides from unphosphorylated peptides, observing just one phosphopeptide from a protein is a common result, since many phosphorylated proteins have only one tyrosine-phosphorylated site.

For this reason, it is appropriate to use additional criteria to validate phosphopeptide assignments. Assignments are likely to be correct if any of these additional criteria are met: (i) the same sequence is assigned to co-eluting ions with different charge states, since the MS/MS spectrum changes markedly with charge state; (ii) the site is found in more than one peptide sequence context due to sequence overlaps from incomplete proteolysis or use of proteases other than trypsin; (iii) the site is found in more than one peptide sequence context due to homologous but not identical protein isoforms; (iv) the site is found in more than one peptide sequence context due to homologous but not identical proteins among species; and (v) sites validated by MS/MS analysis of synthetic phosphopeptides corresponding to assigned sequences, since the ion trap mass spectrometer produces highly reproducible MS/MS spectra. The last criterion is routinely employed to confirm novel site assignments of particular interest.

All spectra and all sequence assignments made by Sequest were imported into a relational database. Assigned sequences were accepted or rejected following a conservative, two-step process. In the first step, a subset of high-scoring sequence assignments was selected by filtering for XCorr values of at least 1.5 for a charge state of +1, 2.2 for +2, and 3.3 for +3, allowing a maximum RSp value of 10. Assignments in this subset were rejected if any of the following criteria were satisfied: (i) the spectrum contained at least one major peak (at least 10% as intense as the most intense ion in the spectrum) that could not be mapped to the assigned sequence as an a, b, or y ion, as an ion arising from neutral-loss of water or ammonia from a b or y ion, or as a multiply protonated ion; (ii) the spectrum did not contain a series of b or y ions equivalent to at least six uninterrupted residues; or (iii) the sequence was not observed at least five times in all the studies we have conducted (except for overlapping sequences due to incomplete proteolysis or use of proteases other than trypsin). In the second step, assignments with below-threshold scores were accepted if the low-scoring spectrum showed a high degree of similarity to a high-scoring spectrum collected in another study, which simulates a true reference library-searching strategy. All spectra supporting the final list of assigned sequences (not shown here) were reviewed by at least three scientists to establish their credibility.

The foregoing IAP analysis identified 454 non-redundant phosphotyrosine-containing peptides, 395 phosphotyrosine sites, and 240 tyrosine phosphorylated proteins, the majority of which are novel, from HCC78 cells (data not shown). Among tyrosine phosphorylated kinases were several of those detected are not normally detected by MS analysis in other NSCLC cell lines (unpublished data), including ROS kinase.

EXAMPLE 2

Western Blot Analysis of ROS Kinase Expression in a NSCLC Cell Line

The observation that the HCC78 NSCLC cell line—but not the other NSCLC cell lines—expresses activated ROS kinase was confirmed by Western blot analysis of cell extracts using antibodies specific for ROS and other receptor tyrosine kinases (RTKs) and downstream kinases.

HCC78 cells were lysed in 1× cell lysis buffer (Cell Signaling Technology) supplemented with Protease Arrest™ (G Biosciences) and separated by electrophoresis. All antibodies and reagents for immunoblotting were from Cell Signaling Technology, Inc. (Beverly, Mass.). Western blotting was carried out as described in "Western Immunoblotting Protocol" (Cell Signaling Technology, Inc., 2005-2006 catalogue). Anti-ROS antibody was obtain from Santa Cruz Biotechnology, Inc.

FIG. 5 shows the western blot results. Only HCC78 express ROS protein among many different NSCLC cell lines. ROS protein in HCC78 has much smaller molecular weight than wild type ROS protein, which indicates of a fusion protein.

Western blot confirms ROS fusion protein is tyrosine phosphorylated. Protein lysate from HCC78 cells was immunoprecipitated by phospho-tyrosine antibody, and immunoblotted with total ROS antibody. The same bands were detected from pY-IP as from total lysate by ROS antibody, with IPed bands having a little slower migration, which also indicates phosphorylation of the protein.

EXAMPLE 3

Growth Inhibition of Abnormal ROS Kinase-Expressing Mammalian NSCLC Cell Lines Using siRNA In order to confirm that the truncated form of ROS is driving cell growth and survival in the HCC78 cell line, the ability of siRNA silencing to inhibit growth of these cells was examined. The expression of ROS was down regulated by RNA interference. The following ROS siRNA was ordered from Proligo, Inc., with corresponding ROS sequences indicated in parentheses:

```
                                        (SEQ ID NO: 23)
    5'AAGCCCGGAUGGCAACGUUTT3'  (ROS1(6318-6340);

(SEQ ID NO: 24)
    5'AAGCCUGAAGGCCUGAACUTT3'  (ROS1(7181-7203).
```

$2 \times 10^5$ cells were seeded in 12 well plates the day before the transfection. 100 nM ROS1 siRNA was transfected using Mirus TransIT-TKO Transfection Reagent. 48 hours after transfection, cells were switched to starvation medium for additional 24 hours. Cells were harvested by trypsinization and counted then, and cell lysate was used in WB to check ROS protein level.

Figure 10:
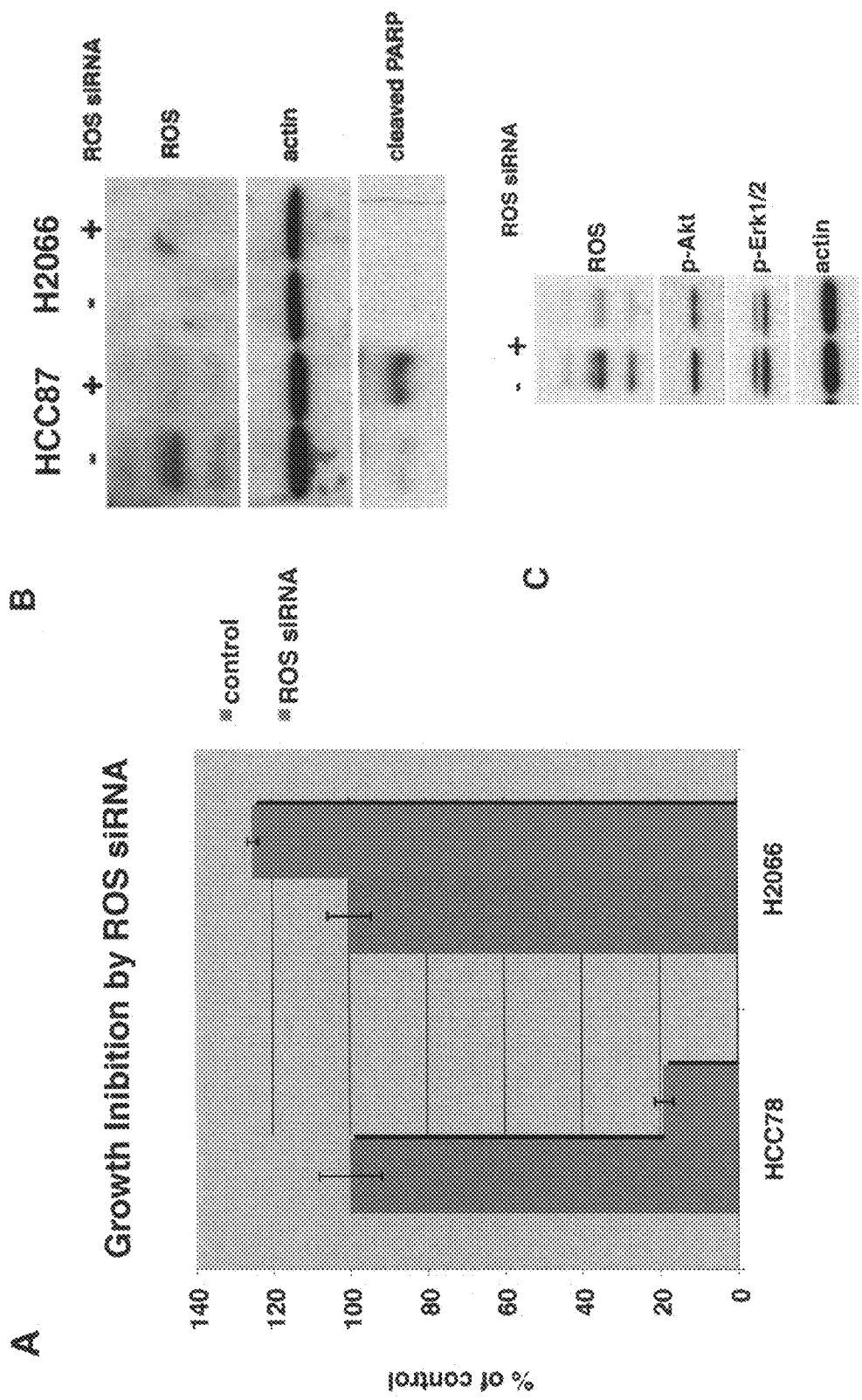
FIG. 10—presents shows siRNA inhibition of mutant ROS kinase in a human NSCLC cell lines: Panel A shows a graph of cell inhibition following siRNA transfection, Panel B is an immunoblot showing specific knock-down of ROS and increased apoptosis (in the mutant ROS-driven cell line), and Panel C is an immunoblot showing decreased activity of signaling molecules downstream of ROS.

Immunoblot analysis revealed the expression of ROS was specifically and significantly reduced at 72 hours following transfection of the siRNA into HCC78 cells, and control cell line H2066 does not express ROS protein (see FIG. 10, panel B). This was accompanied by a decrease in the phosphorylation of downstream substrates, such as p-Erk1/2 and p-Akt, as expected (see FIG. 10, panel C). Moreover, as expected, treatment with ROS siRNA resulted in increased apoptosis of the HCC78 cell line (but not in the control cell line H2066) as determined by detection of cleaved PARP (see FIG. 10, panel B). 80% of the cells were killed 3 days following transfection with ROS siRNA as shown in FIG. 10, panel A. Such results indicate that the mutant/truncated ROS kinase in the HCC78 cell line is driving the proliferation and growth of these NSCLC cells, and that such that growth and proliferation may be inhibited by using siRNA to inhibit ROS kinase expression.

EXAMPLE 4

Isolation & Sequencing of SLC34A2-ROS Fusion Gene

Given the presence of the truncated form of ROS kinase detected in an NSCLC cell line (HCC78), 5' rapid amplification of cDNA ends on the sequence encoding the kinase domain of ROS was conducted in order to determine whether a chimeric ROS transcript was present.

Rapid Amplification of Complementary DNA Ends

RNeasy Mini Kit (Qiagen) was used to extract RNA from HCC78 cell line. DNA was extracted with the use of DNeasy Tissue Kit (Qiagen). Rapid amplification of cDNA ends was performed with the use of 5' RACE system (Invitrogen) with primers ROS-GSP1 for cDNA synthesis and ROS-GSP2 and ROS-GSP3 for a nested PCR reaction.

PCR Assay

For RT-PCR, first-strand cDNA was synthesized from 2.5 µg of total RNA with the use of SuperScript™ III first-strand synthesis system (Invitrogen) with oligo $(dT)_{20}$. Then, the SLC34A2-ROS fusion gene was amplified with the use of primer pairs SLCROS-F1 and SLCROS-R1, SLCROS-F2 and SLCROS-R2.

Constructs

The open reading frame of the SLC34A2-ROS fusion gene was amplified by PCR from cDNA of HCC78 cells with the use of Platinum Taq DNA polymerase high fidelity (Invitrogen) and primer pairs SLC-Fb and ROS-Rb (with Bgl II restriction site). This PCR product was cloned in the retroviral vector MSCV-Neo. Primers were:

```
ROS-GSP1:
ACCCTTCTCGGTTCTTCGTTTCCA         (SEQ ID NO: 13)

ROS-GSP2:
GCAGCTCAGCCAACTCTTTGTCTT         (SEQ ID NO: 14)

ROS-GSP3:
TGCCAGACAAAGGTCAGTGGGATT         (SEQ ID NO: 15)

SLCROS-F1:
TCCATCCCAGCACCTGCGGAG            (SEQ ID NO: 17)

SLCROS-R1:
CTCAACTCTCTATTTCCCAAACAACGC      (SEQ ID NO: 18)

SLCROS-F2:
CATGGCTCCCTGGCCTGAATTG           (SEQ ID NO: 19)

SLCROS-R2:
CAACGCTATTAATCAGACCCATCTCC       (SEQ ID NO: 20)

SLC-Fb:
GAAGATCTCTGACCATGGCTCCCTGGCCTGAA (SEQ ID NO: 21)

ROS-Rb:
GAAGATCTACGCTATTAATCAGACCCATCTCC (SEQ ID NO: 22)
```

FIG. 7 shows the detection of the PCR amplification product after 2 rounds. Sequence analysis of the resultant product revealed that the c-terminal of ROS was fused to SLC34A2 gene N-terminus (see FIG. 1, panel B and C): The SLC34A2-ROS fusion gene was in-frame and fused the first 126 amino acids of SLC34A2 to the last 598 or 495 amino acids of ROS (see FIG. 1, panel B), respectively resulting in two variant fusion protein (long, short). SLC34A2 was located on chromosome 4p15, whereas ROS was on chromosome 6q22. Thus, the fusion gene was created by t(4; 6)(p15;q22). See FIG. 8, top panel.

The fusion of SLC34A2 and ROS was confirmed by reverse-transcriptase-PCR on RNA.

EXAMPLE 5

SLC34A2-ROS Fusion Protein Drives Growth and Survival of Transfected 293 Cells In order to confirm that expression of the SLC34A2-ROS fusion protein can transform normal cells into a cancerous phenotype, human embryonic kidney cells (293 cells) were transfected with the cDNA construct described above, encoding the long variant of SLC34A2-ROS fusion protein.

Figure 9:
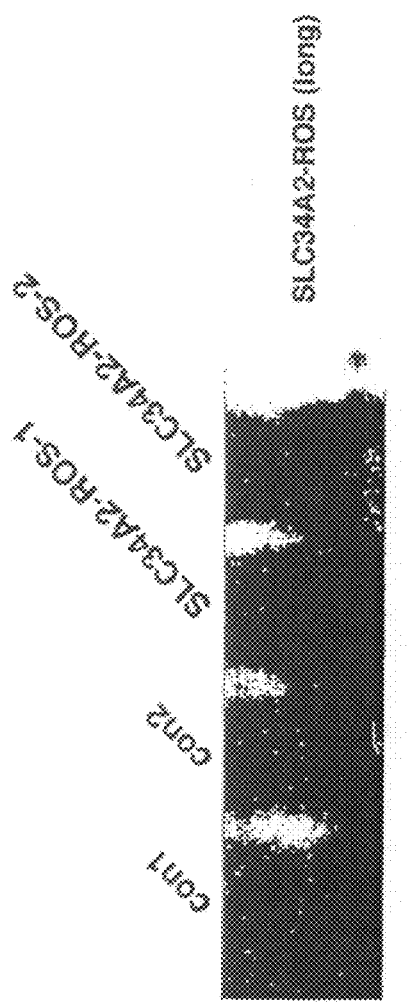
FIG. 9—is a gel showing expression of the SLC34A2-ROS fusion protein (first (long) variant) in transfected 293 cells (human embryonic kidney), as compared to controls (lanes 1 and 2).

The SLC34A2-ROS cDNA construct described above (encoding the long variant fusion protein) was inserted into a MSCV virus vector and transfected into HEK293 cells using SuperFect transfection reagent (Qiagen). 48 hours later, transfected HEK293 cells were harvested and checked by Western blot to confirm the expression of the recombinant SLC34A2-ROS fusion protein (long variant) of the expected molecular weight (see FIG. 9).

EXAMPLE 6

SLC34A2-ROS Fusion Protein Drives Growth and Survival of Transformed Mammalian Cell Line In order to confirm that expression of the SLC34A2-ROS fusion protein can transform normal cells into a cancerous phenotype, 3T3 cells may be transformed with a cDNA construct described above. Cells are maintained in DMEM medium (Invitrogen) with 10% fetal calf serum (FCS) (Invitrogen).

Production of retroviral supernatant and transduction are carried out as previously described. See Schwaller et al., Embo J. 17(18): 5321-33 (1998). 3T3 cells are transduced with retroviral supernatant containing either the MSCV-Neo or MSCV-Neo/SLC34A2-ROS (long) or MSCV-Neo/ROS (short) vectors, respectively, and selected for G418 (500 ug/ml). Stably transfected cells will be used in soft agar assay to confirm SLC34A2-ROS will transform 3T3 cells.

Such analysis would confirm whether the expression of SLC34A2-ROS fusion protein transforms 3T3 cells so that the cell growth will become attachment independent. Western blot analysis is then performed to check phosphorylation status of ROS, SLC34A2, SHP-1 and other possible ROS downstream targets.

EXAMPLE 7

Detection of SLC34A2-ROS Fusion Protein Expression in a Human Cancer Sample Using FISH Assay The presence of the SLC34A2-ROS fusion protein in human NSCLC tumor samples was detected using a fluorescence in situ hybridization (FISH) assay, as previously described. See, e.g., Verma et al. HUMAN CHROMOSOMES: A MANUAL OF BASIC TECHNIQUES, Pergamon Press, New York, N.Y. (1988). Over 200 paraffin-embedded human NSCLC tumor samples were examined.

For analyzing rearrangements involving ROS, a dual color break-apart probe was designed. A proximal probe (BAC clone RP1-179P9) and two distal probes (BAC clone RP11-323017, RP1-94G16) were labeled with Spectrum Orange dUTP or Spectrum Green dUTP, respectively. Labeling of the probes by nick translation and interphase FISH using FFPE tissue sections were done according to the manufactures instructions (Vysis) with the following modifications. In brief, paraffin embedded tissue sections were re-hydrated and subjected to microwave antigen retrieval in 0.01M Citrate buffer (pH 6.0) for 11 minutes. Sections were digested with Protease (4 mg/ml Pepsin, 2000-3000 U/mg) for 25 minutes at 37° C., dehydrated and hybridized with the FISH probe set at 37° C. for 18 hours. After washing, 4',6-diamidino-2-phenylindole (DAPI; mg/ml) in Vectashield mounting medium (Vector Laboratories, Burlingame, Calif.) was applied for nuclear counterstaining.

Figure 11:
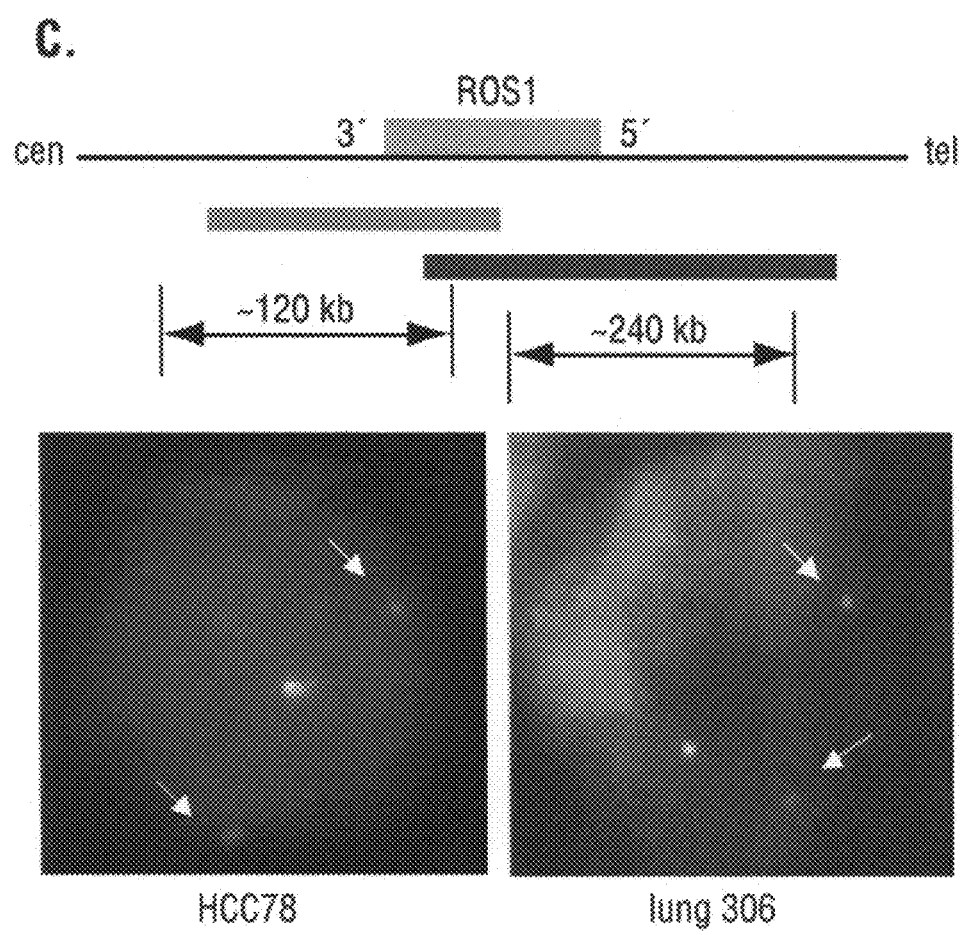
FIG. 11—is an image showing specific detection of the SLC34A2-ROS fusion/translocation (in a human NSCLC cell line) by FISH using a 2-color break-a-part probe.

The ROS rearrangement probe contains two differently labeled probes on opposite sides of the breakpoint of the ROS gene in the wild type sequence (see FIG. 4B and FIG. 1). When hybridized, the native ROS region will appear as an orange/green fusion signal, while rearrangement at this locus (as occurs in the SLC34A2-ROS fusion protein) will result in separate orange and green signals. See FIG. 11.

The FISH analysis revealed a low incidence of this ROS mutation in the sample population studied. Two out of 123 tumors or 1.6% of tumors contained the fusion mutation. However, given the high incidence of NSCLC worldwide (over 151,00 new cases in the U.S. annually, alone), there are expected to be a significant number of patients that harbor this mutant ROS, which patients may benefit from a ROS-inhibiting therapeutic regime.

EXAMPLE 8

Detection of Mutant ROS Kinase Expression in a Human Cancer Sample Using PCR Assay The presence of truncated ROS kinase and/or SLC34A2-ROS fusion protein in a human cancer sample may be detected using either genomic or reverse transcriptase (RT) polymerase chain reaction (PCR), previously described. See, e.g., Cools et al., *N. Engl. J. Med.* 348: 1201-1214 (2003).

Briefly and by way of example, tumor or pleural effusion samples may be obtained from a patient having NSCLC using standard techniques. PCR probes against truncated ROS kinase or SLC34A2-ROS fusion protein are constructed. RNeasy Mini Kit (Qiagen) may be used to extract RNA from the tumor or pleural effusion samples. DNA may be extracted with the use of DNeasy Tissue Kit (Qiagen). For RT-PCR, first-strand cDNA is synthesized from, e.g., 2.5 µg of total RNA with the use, for example, of SuperScript™ III first-strand synthesis system (Invitrogen) with oligo (dT)$_{20}$. Then, the SLC34A2-ROS fusion gene is amplified with the use of primer pairs, e.g. SLC34A2-F1 and ROS-P3 (see Example 4 above). For genomic PCR, amplification of the fusion gene may be performed with the use of Platinum Taq DNA polymerase high fidelity (Invitrogen) with primer pairs, e.g. gSLC34A2-F1 and gROS—R1, or GsIc34A2-F1 and gROS—R2 (see Example 4, above).

Such an analysis will identify a patient having a cancer characterized by expression of the truncated ROS kinase (and/or SLC34A2-ROS fusion protein), which patient is a candidate for treatment using a ROS-inhibiting therapeutic.

EXAMPLE 9

Detection of Mutant ROS Kinase Expression in a Human Cancer Sample Using Global Phosphopeptide Profiling In order to further confirm the incidence of the ROS fusion mutation in human NSCLC, a group of 34 human NSCLC tumors were examined, using the IAP technique of global phosphopeptide profiling described above (see Example 1), to identify ROS phosphopeptides in these tumors. Tumor samples (dissected tumors snap frozen and kept in liquid nitrogen) were obtained from a clinical collaborator in China.

About 300 milligrams of frozen tissue were homogenized in 3 mL of Urea lysis buffer using a Polytron homogenizer. Cell lysate was cleared, reduced, alkylated, and then digested with trypsin overnight at room temperature. These 34 tumors were prescreened for phospho-tyrosine signaling by immunohistocytochemistry, using standard protocols, to be positive.

Global phosphotyrosine profiling of these samples was carried out as described in Example 1 above. The results of the profiling showed one out of the 34 samples have both ROS phospho-peptides and SLC34A2 phospho-peptides (see Table 1 below (other detected phosphopeptides not shown) and also downstream molecules like IRS-1 and IRS-2 phosphopeptides. The tyrosine profiling signature of this tumor is very similar to that of NSCLC cell line HCC78 (see Table 1), as expected. FISH analysis also showed that the tumor has a ROS translocation (see Example 7). RT-PCR, DNA sequencing assay can be used to further confirm that ROS activation in this patient (and other patients harboring the ROS translocation) is due to the aberrant transcript of SLC34A2/ROS.

TABLE 1

Phosphopeptide Profiling of Human NSCLC Tumors.

| Name | Accession | Site | Peptides | HCC78 (cell line) | cs042 (tumor) |
|------|-----------|------|----------|-------------------|---------------|
| ROS | P08922 | 1923 | GLAAGVGLANACyAIHTLPTQEEIENLPAFPR | 1 | 1 |
| ROS | P08922 | 2110 | DIyKNDYYR; DIyKNDYyR; DIyKNDyYR; DIyKNDyyRKRGEGLLPVR | 12 | 4 |
| ROS | P08922 | 2114 | DIYKNDyYR; DIyKNDyYR; DIyKNDyyRKRGEGLLPVR | 11 | 3 |
| ROS | P08922 | 2115 | DIyKNDYyR; DIyKNDyyRKRGEGLLPVR | 1 | 1 |
| ROS | P08922 | 2274 | EGLNyMVLATECGQGEEK; NREGLNyMVLATECGQGEEK; EGLNyMVLATECGQGEEKSEGPLGSQESESCGLR; NREGLNyMVLATECGQGEEKSEGPLGSQESESCGLR | 20 | |
| ROS | P08922 | 2323 | QVAyCPSGKPEGUNYACLTHSGYGDGSD; QVAyCPSGKPEGLNYACLTHSGyGDGSD; QVAyCPSGKPEGLNyACLTHSGYGDGSD | 4 | 1 |

TABLE 1-continued

Phosphopeptide Profiling of Human NSCLC Tumors.

| Name | Accession | Site | Peptides | HCC78 (cell line) | cs042 (tumor) |
|---|---|---|---|---|---|
| ROS | P08922 | 2334 | QVAYCPSGKPEGLNyACLTHSGYGDGSD; QVAYCPSGKPEGLNyACLTHSGyGDGSD; QVAyCPSGKPEGLNyACLTHSGYGDGSD | 7 | 2 |
| ROS | P08922 | 2342 | QVAYCPSGKPEGLNyACLTHSGyGDGSD; QVAyCPSGKPEGLNYACLTHSGyGDGSD | 3 | |
| IRS-1 | P35568 | 612 | GGHHRPDSSTLHTDDGyMPMSPGVAPVPSGR | | 1 |
| IRS-1 | P35568 | 632 | KGSGDyMPMSPK VDPNGyMMMSPSGGCSPDIGGGPSSSSSSSNAVPSGT | 2 | 1 |
| IRS-1 | P35568 | 662 | SYGK | 3 | |
| IRS-2 | Q9Y4H2 | 598 | QRPVPQPSSASLDEyTLMR | | 1 |
| IRS-2 | Q9Y4H2 | 653 | SSSSNLGADDGyMPMTPGAALAGSGSGSCR | 4 | 5 |
| IRS-2 | Q9Y4H2 | 675 | SDDyMPMSPASVSAPK | 3 | 4 |
| IRS-2 | Q9Y4H2 | 742 | ASSPAESSPEDSGyMR | 3 | 3 |
| IRS-2 | Q9Y4H2 | 823 | APYTCGGDSDQyVLMSSPVGR; SYKAPYTCGGDSDQyVLMSSPVGR | 2 | 5 |
| SLC34A2 | O95436 | 54 | IELLPSySTATLIDEPTEVDDPWNLPTLQDSGIK | 1 | 1 |

---

What is claimed is:

1. An isolated polynucleotide comprising a nucleotide sequence at least 95% identical to a sequence selected from the group consisting of:
   (a) a nucleotide sequence encoding a SLC34A2-ROS fusion polypeptide comprising the N-terminal amino acid sequence of SLC34A2 (residues 1-126 of SEQ ID NO: 5) and the kinase domain of ROS (residues 1945-2222 of SEQ ID NO: 7), and
   (b) a nucleotide sequence complementary to the nucleotide sequence of (a), wherein said isolated polynucleotide encode a SLC34A2-ROS fusion polypeptide.

2. The isolated polynucleotide of claim 1, wherein said nucleotide sequence of (a) comprises the coding nucleotide sequence of the cDNA clone contained in ATCC Deposit No. PTA-7877.

3. An isolated polynucleotide comprising a nucleotide sequence selected from the group consisting of:
   (a) a nucleotide sequence encoding a SLC34A2-ROS fusion polypeptide comprising the N-terminal amino acid sequence of SLC34A2 (residues 1-126 of SEQ ID NO: 5) and the kinase domain of ROS (residues 1945-2222 of SEQ ID NO: 7), and
   (b) a nucleotide sequence complementary to the nucleotide sequence of (a).

4. A recombinant vector comprising the isolated nucleic acid molecule of claim 1 or claim 3.

5. A recombinant host cell comprising the recombinant vector of claim 4.

* * * * *

SEQUENCE LISTING

<160> NUMBER OF SEQ ID NOS: 21

<210> SEQ ID NO 1
<211> LENGTH: 724
<212> TYPE: PRT
<213> ORGANISM: Homo sapiens

<400> SEQUENCE: 1

Met Ala Pro Trp Pro Glu Leu Gly Asp Ala Gln Pro Asn Pro Asp Lys
1               5                   10                  15

Tyr Leu Glu Gly Ala Ala Gly Gln Gln Pro Thr Ala Pro Asp Lys Ser
            20                  25                  30

Lys Glu Thr Asn Lys Thr Asp Asn Thr Glu Ala Pro Val Thr Lys Ile
        35                  40                  45

Glu Leu Leu Pro Ser Tyr Ser Thr Ala Thr Leu Ile Asp Glu Pro Thr
    50                  55                  60

Glu Val Asp Asp Pro Trp Asn Leu Pro Thr Leu Gln Asp Ser Gly Ile
65                  70                  75                  80

Lys Trp Ser Glu Arg Asp Thr Lys Gly Lys Ile Leu Cys Phe Phe Gln
                85                  90                  95

Gly Ile Gly Arg Leu Ile Leu Leu Leu Gly Phe Leu Tyr Phe Phe Val
            100                 105                 110

Cys Ser Leu Asp Ile Leu Ser Ser Ala Phe Gln Leu Val Gly Ala Gly
        115                 120                 125

Val Pro Asn Lys Pro Gly Ile Pro Lys Leu Leu Glu Gly Ser Lys Asn
    130                 135                 140

Ser Ile Gln Trp Glu Lys Ala Glu Asp Asn Gly Cys Arg Ile Thr Tyr
145                 150                 155                 160

```
Tyr Ile Leu Glu Ile Arg Lys Ser Thr Ser Asn Asn Leu Gln Asn Gln
                165                 170                 175

Asn Leu Arg Trp Lys Met Thr Phe Asn Gly Ser Cys Ser Ser Val Cys
            180                 185                 190

Thr Trp Lys Ser Lys Asn Leu Lys Gly Ile Phe Gln Phe Arg Val Val
        195                 200                 205

Ala Ala Asn Asn Leu Gly Phe Gly Glu Tyr Ser Gly Ile Ser Glu Asn
    210                 215                 220

Ile Ile Leu Val Gly Asp Asp Phe Trp Ile Pro Glu Thr Ser Phe Ile
225                 230                 235                 240

Leu Thr Ile Ile Val Gly Ile Phe Leu Val Val Thr Ile Pro Leu Thr
                245                 250                 255

Phe Val Trp His Arg Arg Leu Lys Asn Gln Lys Ser Ala Lys Glu Gly
            260                 265                 270

Val Thr Val Leu Ile Asn Glu Asp Lys Glu Leu Ala Glu Leu Arg Gly
        275                 280                 285

Leu Ala Ala Gly Val Gly Leu Ala Asn Ala Cys Tyr Ala Ile His Thr
    290                 295                 300

Leu Pro Thr Gln Glu Glu Ile Glu Asn Leu Pro Ala Phe Pro Arg Glu
305                 310                 315                 320

Lys Leu Thr Leu Arg Leu Leu Gly Ser Gly Ala Phe Gly Glu Val
                325                 330                 335

Tyr Glu Gly Thr Ala Val Asp Ile Leu Gly Val Gly Ser Gly Glu Ile
            340                 345                 350

Lys Val Ala Val Lys Thr Leu Lys Lys Gly Ser Thr Asp Gln Glu Lys
        355                 360                 365

Ile Glu Phe Leu Lys Glu Ala His Leu Met Ser Lys Phe Asn His Pro
    370                 375                 380

Asn Ile Leu Lys Gln Leu Gly Val Cys Leu Leu Asn Glu Pro Gln Tyr
385                 390                 395                 400

Ile Ile Leu Glu Leu Met Glu Gly Gly Asp Leu Leu Thr Tyr Leu Arg
                405                 410                 415

Lys Ala Arg Met Ala Thr Phe Tyr Gly Pro Leu Leu Thr Leu Val Asp
            420                 425                 430

Leu Val Asp Leu Cys Val Asp Ile Ser Lys Gly Cys Val Tyr Leu Glu
        435                 440                 445

Arg Met His Phe Ile His Arg Asp Leu Ala Ala Arg Asn Cys Leu Val
    450                 455                 460

Ser Val Lys Asp Tyr Thr Ser Pro Arg Ile Val Lys Ile Gly Asp Phe
465                 470                 475                 480

Gly Leu Ala Arg Asp Ile Tyr Lys Asn Asp Tyr Tyr Arg Lys Arg Gly
                485                 490                 495

Glu Gly Leu Leu Pro Val Arg Trp Met Ala Pro Glu Ser Leu Met Asp
            500                 505                 510

Gly Ile Phe Thr Thr Gln Ser Asp Val Trp Ser Phe Gly Ile Leu Ile
        515                 520                 525

Trp Glu Ile Leu Thr Leu Gly His Gln Pro Tyr Pro Ala His Ser Asn
    530                 535                 540

Leu Asp Val Leu Asn Tyr Val Gln Thr Gly Gly Arg Leu Glu Pro Pro
545                 550                 555                 560

Arg Asn Cys Pro Asp Asp Leu Trp Asn Leu Met Thr Gln Cys Trp Ala
                565                 570                 575

Gln Glu Pro Asp Gln Arg Pro Thr Phe His Arg Ile Gln Asp Gln Leu
            580                 585                 590
```

```
Gln Leu Phe Arg Asn Phe Phe Leu Asn Ser Ile Tyr Lys Ser Arg Asp
        595                 600                 605

Glu Ala Asn Asn Ser Gly Val Ile Asn Glu Ser Phe Glu Gly Glu Asp
    610                 615                 620

Gly Asp Val Ile Cys Leu Asn Ser Asp Asp Ile Met Pro Val Ala Leu
625                 630                 635                 640

Met Glu Thr Lys Asn Arg Glu Gly Leu Asn Tyr Met Val Leu Ala Thr
                645                 650                 655

Glu Cys Gly Gln Gly Glu Glu Lys Ser Glu Gly Pro Leu Gly Ser Gln
            660                 665                 670

Glu Ser Glu Ser Cys Gly Leu Arg Lys Glu Glu Lys Glu Pro His Ala
        675                 680                 685

Asp Lys Asp Phe Cys Gln Glu Lys Gln Val Ala Tyr Cys Pro Ser Gly
    690                 695                 700

Lys Pro Glu Gly Leu Asn Tyr Ala Cys Leu Thr His Ser Gly Tyr Gly
705                 710                 715                 720

Asp Gly Ser Asp
```

<210> SEQ ID NO 2
<211> LENGTH: 2175
<212> TYPE: DNA
<213> ORGANISM: Homo sapiens

<400> SEQUENCE: 2

```
atggctccct ggcctgaatt gggagatgcc cagcccaacc ccgataagta cctcgaaggg      60
gccgcaggtc agcagcccac tgcccctgat aaaagcaaag agaccaacaa aacagataac     120
actgaggcac ctgtaaccaa gattgaactt ctgccgtcct actccacggc tacactgata     180
gatgagccca ctgaggtgga tgaccctgg aacctaccca ctcttcagga ctcggggatc      240
aagtggtcag agagagacac caaagggaag attctctgtt tcttccaagg gattgggaga     300
ttgattttac ttctcggatt tctctacttt ttcgtgtgct ccctggatat tcttagtagc     360
gccttccagc tggttggagc tggagtccca aataaaccag gcattcccaa attactagaa     420
gggagtaaaa attcaataca gtgggagaaa gctgaagata tggatgtag aattacatac     480
tatatccttg agataagaaa gagcacttca ataatttac agaaccagaa tttaaggtgg      540
aagatgacat ttaatggatc ctgcagtagt gttttgcacat ggaagtccaa aaacctgaaa    600
ggaatatttc agttcagagt agtagctgca ataatctag gtttggtga atatagtgga      660
atcagtgaga atattatatt agttggagat gatttttgga taccagaaac aagtttcata     720
cttactatta tagttggaat atttctggtt gttacaatcc cactgacctt tgtctggcat     780
agaagattaa agaatcaaaa aagtgccaag gaaggggtga cagtgctat aaacgaagac      840
aaagagttgg ctgagctgcg aggtctggca gccggagtag gcctggctaa tgcctgctat     900
gcaatacata ctcttccaac ccaagaggag attgaaaatc ttcctgcctt ccctcgggaa     960
aaactgactc tgcgtctctt gctgggaagt ggagcctttg agaagtgta tgaaggaaca    1020
gcagtggaca tcttaggagt tggaagtgga gaaatcaaag tagcagtgaa gactttgaag    1080
aagggttcca cagaccagga gaagattgaa ttcctgaagg aggcacatct gatgagcaaa    1140
tttaatcatc ccaacattct gaagcagctt ggagtttgtc tgctgaatga accccaatac    1200
attatcctgg aactgatgga gggaggagac cttcttactt atttgcgtaa agcccggatg    1260
gcaacgtttt atggtccttt actcaccttg gttgaccttg tagacctgtg tgtagatatt    1320
tcaaaaggct gtgtctactt ggaacggatg catttcattc acagggatct ggcagctaga    1380
```

```
aattgccttg tttccgtgaa agactatacc agtccacgga tagtgaagat tggagacttt    1440
ggactcgcca gagacatcta taaaaatgat tactatagaa agagagggga aggcctgctc    1500
ccagttcggt ggatggctcc agaaagtttg atggatggaa tcttcactac tcaatctgat    1560
gtatggtctt ttggaattct gatttgggag attttaactc ttggtcatca gccttatcca    1620
gctcattcca accttgatgt gttaaactat gtgcaaacag agggagact  ggagccacca    1680 agaaattgtc ctgatgatct gtggaattta atgacccagt gctgggctca agaacccgac    1740
caaagaccta cttttcatag aattcaggac caacttcagt tattcagaaa ttttttctta    1800
aatagcattt ataagtccag agatgaagca acaacagtg  gagtcataaa tgaaagcttt    1860
gaaggtgaag atggcgatgt gatttgtttg aattcagatg acattatgcc agttgcttta    1920
atggaaacga agaaccgaga agggttaaac tatatggtac ttgctacaga atgtggccaa    1980
ggtgaagaaa agtctgaggg tcctctaggc tcccaggaat ctgaatcttg tggtctgagg    2040
aaagaagaga aggaaccaca tgcagacaaa gatttctgcc aagaaaaaca agtggcttac    2100
tgcccttctg gcaagcctga aggcctgaac tatgcctgtc tcactcacag tggatatgga    2160
gatgggtctg attaa                                                    2175

<210> SEQ ID NO 3
<211> LENGTH: 621
<212> TYPE: PRT
<213> ORGANISM: Homo sapiens

<400> SEQUENCE: 3

Met Ala Pro Trp Pro Glu Leu Gly Asp Ala Gln Pro Asn Pro Asp Lys
1               5                   10                  15

Tyr Leu Glu Gly Ala Ala Gly Gln Gln Pro Thr Ala Pro Asp Lys Ser
            20                  25                  30

Lys Glu Thr Asn Lys Thr Asp Asn Thr Glu Ala Pro Val Thr Lys Ile
        35                  40                  45

Glu Leu Leu Pro Ser Tyr Ser Thr Ala Thr Leu Ile Asp Glu Pro Thr
    50                  55                  60

Glu Val Asp Asp Pro Trp Asn Leu Pro Thr Leu Gln Asp Ser Gly Ile
65                  70                  75                  80

Lys Trp Ser Glu Arg Asp Thr Lys Gly Lys Ile Leu Cys Phe Phe Gln
                85                  90                  95

Gly Ile Gly Arg Leu Ile Leu Leu Gly Phe Leu Tyr Phe Phe Val
            100                 105                 110

Cys Ser Leu Asp Ile Leu Ser Ser Ala Phe Gln Leu Val Gly Asp Asp
        115                 120                 125

Phe Trp Ile Pro Glu Thr Ser Phe Ile Leu Thr Ile Val Gly Ile
    130                 135                 140

Phe Leu Val Val Thr Ile Pro Leu Thr Phe Val Trp His Arg Arg Leu
145                 150                 155                 160

Lys Asn Gln Lys Ser Ala Lys Glu Gly Val Thr Val Leu Ile Asn Glu
                165                 170                 175

Asp Lys Glu Leu Ala Glu Leu Arg Gly Leu Ala Ala Gly Val Gly Leu
            180                 185                 190

Ala Asn Ala Cys Tyr Ala Ile His Thr Leu Pro Thr Gln Glu Glu Ile
        195                 200                 205

Glu Asn Leu Pro Ala Phe Pro Arg Glu Lys Leu Thr Leu Arg Leu Leu
    210                 215                 220

Leu Gly Ser Gly Ala Phe Gly Glu Val Tyr Glu Gly Thr Ala Val Asp
```

```
                225                 230                 235                 240
Ile Leu Gly Val Gly Ser Gly Glu Ile Lys Val Ala Val Lys Thr Leu
                245                 250                 255
Lys Lys Gly Ser Thr Asp Gln Glu Lys Ile Glu Phe Leu Lys Glu Ala
            260                 265                 270
His Leu Met Ser Lys Phe Asn His Pro Asn Ile Leu Lys Gln Leu Gly
        275                 280                 285
Val Cys Leu Leu Asn Glu Pro Gln Tyr Ile Ile Leu Glu Leu Met Glu
    290                 295                 300
Gly Gly Asp Leu Leu Thr Tyr Leu Arg Lys Ala Arg Met Ala Thr Phe
305                 310                 315                 320
Tyr Gly Pro Leu Leu Thr Leu Val Asp Leu Val Asp Leu Cys Val Asp
                325                 330                 335
Ile Ser Lys Gly Cys Val Tyr Leu Glu Arg Met His Phe Ile His Arg
            340                 345                 350
Asp Leu Ala Ala Arg Asn Cys Leu Val Ser Val Lys Asp Tyr Thr Ser
        355                 360                 365
Pro Arg Ile Val Lys Ile Gly Asp Phe Gly Leu Ala Arg Asp Ile Tyr
    370                 375                 380
Lys Asn Asp Tyr Tyr Arg Lys Arg Gly Glu Gly Leu Leu Pro Val Arg
385                 390                 395                 400
Trp Met Ala Pro Glu Ser Leu Met Asp Gly Ile Phe Thr Thr Gln Ser
                405                 410                 415
Asp Val Trp Ser Phe Gly Ile Leu Ile Trp Glu Ile Leu Thr Leu Gly
            420                 425                 430
His Gln Pro Tyr Pro Ala His Ser Asn Leu Asp Val Leu Asn Tyr Val
        435                 440                 445
Gln Thr Gly Gly Arg Leu Glu Pro Pro Arg Asn Cys Pro Asp Asp Leu
    450                 455                 460
Trp Asn Leu Met Thr Gln Cys Trp Ala Gln Glu Pro Asp Gln Arg Pro
465                 470                 475                 480
Thr Phe His Arg Ile Gln Asp Gln Leu Gln Leu Phe Arg Asn Phe Phe
                485                 490                 495
Leu Asn Ser Ile Tyr Lys Ser Arg Asp Glu Ala Asn Asn Ser Gly Val
            500                 505                 510
Ile Asn Glu Ser Phe Glu Gly Glu Asp Gly Asp Val Ile Cys Leu Asn
        515                 520                 525
Ser Asp Asp Ile Met Pro Val Ala Leu Met Glu Thr Lys Asn Arg Glu
    530                 535                 540
Gly Leu Asn Tyr Met Val Leu Ala Thr Glu Cys Gly Gln Gly Glu Glu
545                 550                 555                 560
Lys Ser Glu Gly Pro Leu Gly Ser Gln Glu Ser Glu Ser Cys Gly Leu
                565                 570                 575
Arg Lys Glu Glu Lys Glu Pro His Ala Asp Lys Asp Phe Cys Gln Glu
            580                 585                 590
Lys Gln Val Ala Tyr Cys Pro Ser Gly Lys Pro Glu Gly Leu Asn Tyr
        595                 600                 605
Ala Cys Leu Thr His Ser Gly Tyr Gly Asp Gly Ser Asp
610                 615                 620

<210> SEQ ID NO 4
<211> LENGTH: 1866
<212> TYPE: DNA
<213> ORGANISM: Homo sapiens
```

<400> SEQUENCE: 4

```
atggctccct ggcctgaatt gggagatgcc cagcccaacc ccgataagta cctcgaaggg    60
gccgcaggtc agcagcccac tgcccctgat aaaagcaaag agaccaacaa aacagataac   120
actgaggcac ctgtaaccaa gattgaactt ctgccgtcct actccacggc tacactgata   180
gatgagccca ctgaggtgga tgacccctgg aacctaccca ctcttcagga ctcggggatc   240
aagtggtcag agagagacac caaagggaag attctctgtt tcttccaagg gattgggaga   300
ttgattttac ttctcggatt tctctacttt ttcgtgtgct ccctggatat tcttagtagc   360
gccttccagc tggttggaga tgattttttgg ataccagaaa caagtttcat acttactatt   420
atagttggaa tatttctggt tgttacaatc ccactgacct ttgtctggca tagaagatta   480
aagaatcaaa aaagtgccaa ggaaggggtg acagtgctta taacgaaga caaagagttg   540
gctgagctgc gaggtctggc agccggagta ggcctggcta atgcctgcta tgcaatacat   600
actcttccaa cccaagagga gattgaaaat cttcctgcct tccctcggga aaaactgact   660
ctgcgtctct tgctgggaag tggagccttt ggagaagtgt atgaaggaac agcagtggac   720
atcttaggag ttggaagtgg agaaatcaaa gtagcagtga agacttttgaa gaagggttcc   780
acagaccagg agaagattga attcctgaag gaggcacatc tgatgagcaa atttaatcat   840
cccaacattc tgaagcagct ggagtttgt ctgctgaatg aaccccaata cattatcctg   900
gaactgatgg agggaggaga ccttcttact tatttgcgta agcccggat ggcaacgttt   960
tatggtcctt tactcacctt ggttgacctt gtagacctgt gtgtagatat ttcaaaaggc  1020
tgtgtctact tggaacggat gcatttcatt cacagggatc tggcagctag aaattgcctt  1080
gtttccgtga aagactatac cagtccacgg atagtgaaga ttggagactt tggactcgcc  1140
agagacatct ataaaaatga ttactataga agagagggg aaggcctgct cccagttcgg  1200
tggatggctc cagaaagttt tgatggatgga atcttcacta ctcaatctga tgtatggtct  1260
tttggaattc tgatttggga gatttttaact cttggtcatc agccttatcc agctcattcc  1320
aaccttgatg tgttaaacta tgtgcaaaca ggagggagac tggagccacc aagaaattgt  1380
cctgatgatc tgtggaattt aatgacccag tgctgggctc aagaacccga ccaaagacct  1440
acttttcata gaattcagga ccaacttcag ttattcagaa attttttctt aaatagcatt  1500
tataagtcca gagatgaagc aaacaacagt ggagtcataa atgaaagctt tgaaggtgaa  1560
gatggcgatg tgatttgttt gaattcagat gacattatgc cagttgcttt aatggaaacg  1620
aagaaccgag aagggttaaa ctatatggta cttgctacag aatgtggcca aggtgaagaa  1680
aagtctgagg gtcctctagg ctcccaggaa tctgaatctt gtggtctgag gaagaagag  1740
aaggaaccac atgcagacaa agatttctgc caagaaaaac aagtggctta ctgcccttct  1800
ggcaagcctg aaggcctgaa ctatgcctgt ctcactcaca gtggatatgg agatgggtct  1860
gattaa                                                              1866
```

<210> SEQ ID NO 5
<211> LENGTH: 690
<212> TYPE: PRT
<213> ORGANISM: Homo sapiens

<400> SEQUENCE: 5

```
Met Ala Pro Trp Pro Glu Leu Gly Asp Ala Gln Pro Asn Pro Asp Lys
1               5                  10                  15
Tyr Leu Glu Gly Ala Ala Gly Gln Gln Pro Thr Ala Pro Asp Lys Ser
            20                  25                  30
```

```
            -continued

Lys Glu Thr Asn Lys Thr Asp Asn Thr Glu Ala Pro Val Thr Lys Ile
            35                  40                  45

Glu Leu Leu Pro Ser Tyr Ser Thr Ala Thr Leu Ile Asp Glu Pro Thr
 50                  55                  60

Glu Val Asp Asp Pro Trp Asn Leu Pro Thr Leu Gln Asp Ser Gly Ile
 65                  70                  75                  80

Lys Trp Ser Glu Arg Asp Thr Lys Gly Lys Ile Leu Cys Phe Phe Gln
                 85                  90                  95

Gly Ile Gly Arg Leu Ile Leu Leu Gly Phe Leu Tyr Phe Phe Val
                100                 105                 110

Cys Ser Leu Asp Ile Leu Ser Ser Ala Phe Gln Leu Val Gly Gly Lys
                115                 120                 125

Met Ala Gly Gln Phe Phe Ser Asn Ser Ser Ile Met Ser Asn Pro Leu
            130                 135                 140

Leu Gly Leu Val Ile Gly Val Leu Val Thr Val Leu Gln Ser Ser
145                 150                 155                 160

Ser Thr Ser Thr Ser Ile Val Val Ser Met Val Ser Ser Leu Leu
                165                 170                 175

Thr Val Arg Ala Ala Ile Pro Ile Ile Met Gly Ala Asn Ile Gly Thr
                180                 185                 190

Ser Ile Thr Asn Thr Ile Val Ala Leu Met Gln Val Gly Asp Arg Ser
            195                 200                 205

Glu Phe Arg Arg Ala Phe Ala Gly Ala Thr Val His Asp Phe Phe Asn
210                 215                 220

Trp Leu Ser Val Leu Val Leu Leu Pro Val Glu Val Ala Thr His Tyr
225                 230                 235                 240

Leu Glu Ile Ile Thr Gln Leu Ile Val Glu Ser Phe His Phe Lys Asn
                245                 250                 255

Gly Glu Asp Ala Pro Asp Leu Leu Lys Val Ile Thr Lys Pro Phe Thr
            260                 265                 270

Lys Leu Ile Val Gln Leu Asp Lys Lys Val Ile Ser Gln Ile Ala Met
        275                 280                 285

Asn Asp Glu Lys Ala Lys Asn Lys Ser Leu Val Lys Ile Trp Cys Lys
290                 295                 300

Thr Phe Thr Asn Lys Thr Gln Ile Asn Val Thr Val Pro Ser Thr Ala
305                 310                 315                 320

Asn Cys Thr Ser Pro Ser Leu Cys Trp Thr Asp Gly Ile Gln Asn Trp
                325                 330                 335

Thr Met Lys Asn Val Thr Tyr Lys Glu Asn Ile Ala Lys Cys Gln His
            340                 345                 350

Ile Phe Val Asn Phe His Leu Pro Asp Leu Ala Val Gly Thr Ile Leu
        355                 360                 365

Leu Ile Leu Ser Leu Leu Val Leu Cys Gly Cys Leu Ile Met Ile Val
    370                 375                 380

Lys Ile Leu Gly Ser Val Leu Lys Gly Gln Val Ala Thr Val Ile Lys
385                 390                 395                 400

Lys Thr Ile Asn Thr Asp Phe Pro Phe Pro Phe Ala Trp Leu Thr Gly
                405                 410                 415

Tyr Leu Ala Ile Leu Val Gly Ala Gly Met Thr Phe Ile Val Gln Ser
            420                 425                 430

Ser Ser Val Phe Thr Ser Ala Leu Thr Pro Leu Ile Gly Ile Gly Val
        435                 440                 445

Ile Thr Ile Glu Arg Ala Tyr Pro Leu Thr Leu Gly Ser Asn Ile Gly
    450                 455                 460
```

```
Thr Thr Thr Thr Ala Ile Leu Ala Ala Leu Ala Ser Pro Gly Asn Ala
465                 470                 475                 480

Leu Arg Ser Ser Leu Gln Ile Ala Leu Cys His Phe Phe Asn Ile
            485                 490                 495

Ser Gly Ile Leu Leu Trp Tyr Pro Ile Pro Phe Thr Arg Leu Pro Ile
            500                 505                 510

Arg Met Ala Lys Gly Leu Gly Asn Ile Ser Ala Lys Tyr Arg Trp Phe
            515                 520                 525

Ala Val Phe Tyr Leu Ile Ile Phe Phe Leu Ile Pro Leu Thr Val
        530                 535                 540

Phe Gly Leu Ser Leu Ala Gly Trp Arg Val Leu Val Gly Val Gly Val
545                 550                 555                 560

Pro Val Val Phe Ile Ile Leu Val Leu Cys Leu Arg Leu Leu Gln
                565                 570                 575

Ser Arg Cys Pro Arg Val Leu Pro Lys Lys Leu Gln Asn Trp Asn Phe
            580                 585                 590

Leu Pro Leu Trp Met Arg Ser Leu Lys Pro Trp Asp Ala Val Val Ser
        595                 600                 605

Lys Phe Thr Gly Cys Phe Gln Met Arg Cys Cys Tyr Cys Cys Arg Val
    610                 615                 620

Cys Cys Arg Ala Cys Cys Leu Leu Cys Gly Cys Pro Lys Cys Cys Arg
625                 630                 635                 640

Cys Ser Lys Cys Cys Glu Asp Leu Glu Glu Ala Gln Glu Gly Gln Asp
            645                 650                 655

Val Pro Val Lys Ala Pro Glu Thr Phe Asp Asn Ile Thr Ile Ser Arg
            660                 665                 670

Glu Ala Gln Gly Glu Val Pro Ala Ser Asp Ser Lys Thr Glu Cys Thr
            675                 680                 685

Ala Leu
    690

<210> SEQ ID NO 6
<211> LENGTH: 2280
<212> TYPE: DNA
<213> ORGANISM: Homo sapiens

<400> SEQUENCE: 6
cgggccaggt ttccaggctc ggccgccgcc tccatcccag cacctgcgga gggagcgctg     60
accatggctc cctggcctga attgggagat gcccagccca ccccgataag tacctcgaa    120
ggggccgcag gtcagcagcc cactgcccct gataaaagca agagaccaa caaacagat    180
aacactgagg cacctgtaac caagattgaa cttctgccgt cctactccac ggctacactg    240
atagatgagc ccactgaggt ggatgacccc tggaacctac ccactcttca ggactcgggg    300
atcaagtggt cagagagaga caccaaaggg aagattctct gtttcttcca agggattggg    360
agattgattt tacttctcgg atttctctac ttttttcgtgt gctccctgga tattcttagt    420
agcgccttcc agctggttgg aggaaaaatg caggacagt tcttcagcaa cagctctatt    480
atgtccaacc ctttgttggg gctggtgatc ggggtgctgg tgaccgtctt ggtgcagagc    540
tccagcacct caacgtccat cgttgtcagc atggtgtcct cttcattgct cactgttcgg    600
gctgccatcc ccattatcat gggggccaac attggaacgt caatcaccaa cactattgtt    660
gcgctcatgc aggtgggaga tcggagtgag ttcagaagag cttttgcagg agccactgtc    720
catgacttct tcaactggct gtccgtgttg gtgctcttgc ccgtggaggt ggccacccat    780
```

```
tacctcgaga tcataaccca gcttatagtg gagagcttcc acttcaagaa tggagaagat    840
gccccagatc ttctgaaagt catcactaag cccttcacaa agctcattgt ccagctggat    900
aaaaaagtta tcagccaaat tgcaatgaac gatgaaaaag cgaaaaacaa gagtcttgtc    960
aagatttggt gcaaaacttt taccaacaag acccagatta acgtcactgt tccctcgact   1020
gctaactgca cctccccttc cctctgttgg acggatggca tccaaaactg gaccatgaag   1080
aatgtgacct acaaggagaa catcgccaaa tgccagcata tctttgtgaa tttccacctc   1140
ccggatcttg ctgtgggcac atcttgctc atactctccc tgctggtcct ctgtggttgc    1200
ctgatcatga ttgtcaagat cctgggctct gtgctcaagg gcaggtcgc cactgtcatc    1260
aagaagacca tcaacactga tttcccctttt ccctttgcat ggttgactgg ctacctggcc   1320
atcctcgtcg gggcaggcat gaccttcatc gtacagagca gctctgtgtt cacgtcggcc    1380
ttgaccccccc tgattggaat cggcgtgata accattgaga gggcttatcc actcacgctg   1440
ggctccaaca tcggcaccac caccaccgcc atcctggccg ccttagccag ccctggcaat   1500
gcattgagga gttcactcca gatcgccctg tgccactttt tcttcaacat ctccggcatc   1560
ttgctgtggt acccgatccc gttcactcgc ctgcccatcc gcatggccaa ggggctgggc   1620
aacatctctg ccaagtatcg ctggttcgcc gtcttctacc tgatcatctt cttcttcctg   1680
atcccgctga cggtgtttgg cctctcgctg gccggctggc gggtgctggt tggtgtcggg   1740
gttcccgtcg tcttcatcat catcctggta ctgtgcctcc gactcctgca gtctcgctgc   1800
ccacgcgtcc tgccgaagaa actccagaac tggaacttcc tgccgctgtg gatgcgctcg   1860
ctgaagccct gggatgccgt cgtctccaag ttcaccggct gcttccagat gcgctgctgc   1920
tactgctgcc gcgtgtgctg ccgcgcgtgc tgcttgctgt gtggctgccc caagtgctgc   1980
cgctgcagca agtgctgcga ggacttggag gaggcgcagg aggggcagga tgtccctgtc   2040
aaggctcctg agacctttga taacataacc attagcagag aggctcaggg tgaggtccct   2100
gcctcggact caaagaccga atgcacggcc ttgtagggga cgcccagat tgtcagggat   2160
gggggggatgg tccttgagtt ttgcatgctc tcctccctcc cacttctgca cccttttcacc   2220
acctcgagga gatttgctcc ccattagcga atgaaattga tgcagtccta aaaaaaaaaa   2280
```

<210> SEQ ID NO 7  
<211> LENGTH: 2347  
<212> TYPE: PRT  
<213> ORGANISM: Homo sapiens

<400> SEQUENCE: 7

```
Met Lys Asn Ile Tyr Cys Leu Ile Pro Lys Leu Val Asn Phe Ala Thr
1               5                   10                  15

Leu Gly Cys Leu Trp Ile Ser Val Val Gln Cys Thr Val Leu Asn Ser
            20                  25                  30

Cys Leu Lys Ser Cys Val Thr Asn Leu Gly Gln Gln Leu Asp Leu Gly
        35                  40                  45

Thr Pro His Asn Leu Ser Glu Pro Cys Ile Gln Gly Cys His Phe Trp
    50                  55                  60

Asn Ser Val Asp Gln Lys Asn Cys Ala Leu Lys Cys Arg Glu Ser Cys
65                  70                  75                  80

Glu Val Gly Cys Ser Ser Ala Glu Gly Ala Tyr Glu Glu Val Leu
                85                  90                  95

Glu Asn Ala Asp Leu Pro Thr Ala Pro Phe Ala Ser Ser Ile Gly Ser
            100                 105                 110

His Asn Met Thr Leu Arg Trp Lys Ser Ala Asn Phe Ser Gly Val Lys
```

```
                    115                 120                 125
Tyr Ile Ile Gln Trp Lys Tyr Ala Gln Leu Leu Gly Ser Trp Thr Tyr
                130                 135                 140
Thr Lys Thr Val Ser Arg Pro Ser Tyr Val Lys Pro Leu His Pro
145                 150                 155                 160
Phe Thr Glu Tyr Ile Phe Arg Val Val Trp Ile Phe Thr Ala Gln Leu
                165                 170                 175
Gln Leu Tyr Ser Pro Pro Ser Pro Ser Tyr Arg Thr His Pro His Gly
                180                 185                 190
Val Pro Glu Thr Ala Pro Leu Ile Arg Asn Ile Glu Ser Ser Ser Pro
                195                 200                 205
Asp Thr Val Glu Val Ser Trp Asp Pro Pro Gln Phe Pro Gly Gly Pro
210                 215                 220
Ile Leu Gly Tyr Asn Leu Arg Leu Ile Ser Lys Asn Gln Lys Leu Asp
225                 230                 235                 240
Ala Gly Thr Gln Arg Thr Ser Phe Gln Phe Tyr Ser Thr Leu Pro Asn
                245                 250                 255
Thr Ile Tyr Arg Phe Ser Ile Ala Ala Val Asn Glu Val Gly Glu Gly
                260                 265                 270
Pro Glu Ala Glu Ser Ser Ile Thr Thr Ser Ser Ser Ala Val Gln Gln
                275                 280                 285
Glu Glu Gln Trp Leu Phe Leu Ser Arg Lys Thr Ser Leu Arg Lys Arg
                290                 295                 300
Ser Leu Lys His Leu Val Asp Glu Ala His Cys Leu Arg Leu Asp Ala
305                 310                 315                 320
Ile Tyr His Asn Ile Thr Gly Ile Ser Val Asp Val His Gln Gln Ile
                325                 330                 335
Val Tyr Phe Ser Glu Gly Thr Leu Ile Trp Ala Lys Lys Ala Ala Asn
                340                 345                 350
Met Ser Asp Val Ser Asp Leu Arg Ile Phe Tyr Arg Gly Ser Gly Leu
                355                 360                 365
Ile Ser Ser Ile Ser Ile Asp Trp Leu Tyr Gln Arg Met Tyr Phe Ile
370                 375                 380
Met Asp Glu Leu Val Cys Val Cys Asp Leu Glu Asn Cys Ser Asn Ile
385                 390                 395                 400
Glu Glu Ile Thr Pro Pro Ser Ile Ser Ala Pro Gln Lys Ile Val Ala
                405                 410                 415
Asp Ser Tyr Asn Gly Tyr Val Phe Tyr Leu Leu Arg Asp Gly Ile Tyr
                420                 425                 430
Arg Ala Asp Leu Pro Val Pro Ser Gly Arg Cys Ala Glu Ala Val Arg
                435                 440                 445
Ile Val Glu Ser Cys Thr Leu Lys Asp Phe Ala Ile Lys Pro Gln Ala
450                 455                 460
Lys Arg Ile Ile Tyr Phe Asn Asp Thr Ala Gln Val Phe Met Ser Thr
465                 470                 475                 480
Phe Leu Asp Gly Ser Ala Ser His Leu Ile Leu Pro Arg Ile Pro Phe
                485                 490                 495
Ala Asp Val Lys Ser Phe Ala Cys Glu Asn Asn Asp Phe Leu Val Thr
                500                 505                 510
Asp Gly Lys Val Ile Phe Gln Gln Asp Ala Leu Ser Phe Asn Glu Phe
                515                 520                 525
Ile Val Gly Cys Asp Leu Ser His Ile Glu Glu Phe Gly Phe Gly Asn
530                 535                 540
```

```
Leu Val Ile Phe Gly Ser Ser Gln Leu His Pro Leu Pro Gly Arg
545                 550                 555                 560

Pro Gln Glu Leu Ser Val Leu Phe Gly Ser His Gln Ala Leu Val Gln
            565                 570                 575

Trp Lys Pro Pro Ala Leu Ala Ile Gly Ala Asn Val Ile Leu Ile Ser
        580                 585                 590

Asp Ile Ile Glu Leu Phe Glu Leu Gly Pro Ser Ala Trp Gln Asn Trp
                595                 600                 605

Thr Tyr Glu Val Lys Val Ser Thr Gln Asp Pro Glu Val Thr His
610                 615                 620

Ile Phe Leu Asn Ile Ser Gly Thr Met Leu Asn Val Pro Glu Leu Gln
625                 630                 635                 640

Ser Ala Met Lys Tyr Lys Val Ser Val Arg Ala Ser Ser Pro Lys Arg
                645                 650                 655

Pro Gly Pro Trp Ser Glu Pro Ser Val Gly Thr Thr Leu Val Pro Ala
            660                 665                 670

Ser Glu Pro Pro Phe Ile Met Ala Val Lys Glu Asp Gly Leu Trp Ser
            675                 680                 685

Lys Pro Leu Asn Ser Phe Gly Pro Gly Glu Phe Leu Ser Ser Asp Ile
690                 695                 700

Gly Asn Val Ser Asp Met Asp Trp Tyr Asn Asn Ser Leu Tyr Tyr Ser
705                 710                 715                 720

Asp Thr Lys Gly Asp Val Phe Val Trp Leu Leu Asn Gly Thr Asp Ile
                725                 730                 735

Ser Glu Asn Tyr His Leu Pro Ser Ile Ala Gly Ala Gly Ala Leu Ala
            740                 745                 750

Phe Glu Trp Leu Gly His Phe Leu Tyr Trp Ala Gly Lys Thr Tyr Val
            755                 760                 765

Ile Gln Arg Gln Ser Val Leu Thr Gly His Thr Asp Ile Val Thr His
770                 775                 780

Val Lys Leu Leu Val Asn Asp Met Val Val Asp Ser Val Gly Gly Tyr
785                 790                 795                 800

Leu Tyr Trp Thr Thr Leu Tyr Ser Val Glu Ser Thr Arg Leu Asn Gly
            805                 810                 815

Glu Ser Ser Leu Val Leu Gln Thr Gln Pro Trp Phe Ser Gly Lys Lys
            820                 825                 830

Val Ile Ala Leu Thr Leu Asp Leu Ser Asp Gly Leu Leu Tyr Trp Leu
            835                 840                 845

Val Gln Asp Ser Gln Cys Ile His Leu Tyr Thr Ala Val Leu Arg Gly
            850                 855                 860

Gln Ser Thr Gly Asp Thr Thr Ile Thr Glu Phe Ala Ala Trp Ser Thr
865                 870                 875                 880

Ser Glu Ile Ser Gln Asn Ala Leu Met Tyr Tyr Ser Gly Arg Leu Phe
            885                 890                 895

Trp Ile Asn Gly Phe Arg Ile Ile Thr Thr Gln Glu Ile Gly Gln Lys
                900                 905                 910

Thr Ser Val Ser Val Leu Glu Pro Ala Arg Phe Asn Gln Phe Thr Ile
            915                 920                 925

Ile Gln Thr Ser Leu Lys Pro Leu Pro Gly Asn Phe Ser Phe Thr Pro
930                 935                 940

Lys Val Ile Pro Asp Ser Val Gln Glu Ser Ser Phe Arg Ile Glu Gly
945                 950                 955                 960

Asn Ala Ser Ser Phe Gln Ile Leu Trp Asn Gly Pro Pro Ala Val Asp
            965                 970                 975
```

```
Trp Gly Val Val Phe Tyr Ser Val Glu Phe Ser Ala His Ser Lys Phe
        980                 985                 990

Leu Ala Ser Glu Gln His Ser Leu Pro Val Phe Thr Val Glu Gly Leu
        995                 1000                1005

Glu Pro Tyr Ala Leu Phe Asn Leu Ser Val Thr Pro Tyr Thr Tyr
    1010                1015                1020

Trp Gly Lys Gly Pro Lys Thr Ser Leu Ser Leu Arg Ala Pro Glu
    1025                1030                1035

Thr Val Pro Ser Ala Pro Glu Asn Pro Arg Ile Phe Ile Leu Pro
    1040                1045                1050

Ser Gly Lys Cys Cys Asn Lys Asn Glu Val Val Glu Phe Arg
    1055                1060                1065

Trp Asn Lys Pro Lys His Glu Asn Gly Val Leu Thr Lys Phe Glu
    1070                1075                1080

Ile Phe Tyr Asn Ile Ser Asn Gln Ser Ile Thr Asn Lys Thr Cys
    1085                1090                1095

Glu Asp Trp Ile Ala Val Asn Val Thr Pro Ser Val Met Ser Phe
    1100                1105                1110

Gln Leu Glu Gly Met Ser Pro Arg Cys Phe Ile Ala Phe Gln Val
    1115                1120                1125

Arg Ala Phe Thr Ser Lys Gly Pro Gly Pro Tyr Ala Asp Val Val
    1130                1135                1140

Lys Ser Thr Thr Ser Glu Ile Asn Pro Phe Pro His Leu Ile Thr
    1145                1150                1155

Leu Leu Gly Asn Lys Ile Val Phe Leu Asp Met Asp Gln Asn Gln
    1160                1165                1170

Val Val Trp Thr Phe Ser Ala Glu Arg Val Ile Ser Ala Val Cys
    1175                1180                1185

Tyr Thr Ala Asp Asn Glu Met Gly Tyr Tyr Ala Glu Gly Asp Ser
    1190                1195                1200

Leu Phe Leu Leu His Leu His Asn Arg Ser Ser Glu Leu Phe
    1205                1210                1215

Gln Asp Ser Leu Val Phe Asp Ile Thr Val Ile Thr Ile Asp Trp
    1220                1225                1230

Ile Ser Arg His Leu Tyr Phe Ala Leu Lys Glu Ser Gln Asn Gly
    1235                1240                1245

Met Gln Val Phe Asp Val Asp Leu Glu His Lys Val Lys Tyr Pro
    1250                1255                1260

Arg Glu Val Lys Ile His Asn Arg Asn Ser Thr Ile Ile Ser Phe
    1265                1270                1275

Ser Val Tyr Pro Leu Leu Ser Arg Leu Tyr Trp Thr Glu Val Ser
    1280                1285                1290

Asn Phe Gly Tyr Gln Met Phe Tyr Tyr Ser Ile Ile Ser His Thr
    1295                1300                1305

Leu His Arg Ile Leu Gln Pro Thr Ala Thr Asn Gln Gln Asn Lys
    1310                1315                1320

Arg Asn Gln Cys Ser Cys Asn Val Thr Glu Phe Glu Leu Ser Gly
    1325                1330                1335

Ala Met Ala Ile Asp Thr Ser Asn Leu Glu Lys Pro Leu Ile Tyr
    1340                1345                1350

Phe Ala Lys Ala Gln Glu Ile Trp Ala Met Asp Leu Glu Gly Cys
    1355                1360                1365

Gln Cys Trp Arg Val Ile Thr Val Pro Ala Met Leu Ala Gly Lys
```

-continued

```
            1370                1375                1380
Thr Leu Val Ser Leu Thr Val Asp Gly Asp Leu Ile Tyr Trp Ile
        1385                1390                1395
Ile Thr Ala Lys Asp Ser Thr Gln Ile Tyr Gln Ala Lys Lys Gly
    1400                1405                1410
Asn Gly Ala Ile Val Ser Gln Val Lys Ala Leu Arg Ser Arg His
    1415                1420                1425
Ile Leu Ala Tyr Ser Ser Val Met Gln Pro Phe Pro Asp Lys Ala
    1430                1435                1440
Phe Leu Ser Leu Ala Ser Asp Thr Val Glu Pro Thr Ile Leu Asn
    1445                1450                1455
Ala Thr Asn Thr Ser Leu Thr Ile Arg Leu Pro Leu Ala Lys Thr
    1460                1465                1470
Asn Leu Thr Trp Tyr Gly Ile Thr Ser Pro Thr Pro Thr Tyr Leu
    1475                1480                1485
Val Tyr Tyr Ala Glu Val Asn Asp Arg Lys Asn Ser Ser Asp Leu
    1490                1495                1500
Lys Tyr Arg Ile Leu Glu Phe Gln Asp Ser Ile Ala Leu Ile Glu
    1505                1510                1515
Asp Leu Gln Pro Phe Ser Thr Tyr Met Ile Gln Ile Ala Val Lys
    1520                1525                1530
Asn Tyr Tyr Ser Asp Pro Leu Glu His Leu Pro Pro Gly Lys Glu
    1535                1540                1545
Ile Trp Gly Lys Thr Lys Asn Gly Val Pro Glu Ala Val Gln Leu
    1550                1555                1560
Ile Asn Thr Thr Val Arg Ser Asp Thr Ser Leu Ile Ile Ser Trp
    1565                1570                1575
Arg Glu Ser His Lys Pro Asn Gly Pro Lys Glu Ser Val Arg Tyr
    1580                1585                1590
Gln Leu Ala Ile Ser His Leu Ala Leu Ile Pro Glu Thr Pro Leu
    1595                1600                1605
Arg Gln Ser Glu Phe Pro Asn Gly Arg Leu Thr Leu Leu Val Thr
    1610                1615                1620
Arg Leu Ser Gly Gly Asn Ile Tyr Val Leu Lys Val Leu Ala Cys
    1625                1630                1635
His Ser Glu Glu Met Trp Cys Thr Glu Ser His Pro Val Thr Val
    1640                1645                1650
Glu Met Phe Asn Thr Pro Glu Lys Pro Tyr Ser Leu Val Pro Glu
    1655                1660                1665
Asn Thr Ser Leu Gln Phe Asn Trp Lys Ala Pro Leu Asn Val Asn
    1670                1675                1680
Leu Ile Arg Phe Trp Val Glu Leu Gln Lys Trp Lys Tyr Asn Glu
    1685                1690                1695
Phe Tyr His Val Lys Thr Ser Cys Ser Gln Gly Pro Ala Tyr Val
    1700                1705                1710
Cys Asn Ile Thr Asn Leu Gln Pro Tyr Thr Ser Tyr Asn Val Arg
    1715                1720                1725
Val Val Val Val Tyr Lys Thr Gly Glu Asn Ser Thr Ser Leu Pro
    1730                1735                1740
Glu Ser Phe Lys Thr Lys Ala Gly Val Pro Asn Lys Pro Gly Ile
    1745                1750                1755
Pro Lys Leu Leu Glu Gly Ser Lys Asn Ser Ile Gln Trp Glu Lys
    1760                1765                1770
```

-continued

Ala Glu Asp Asn Gly Cys Arg Ile Thr Tyr Tyr Ile Leu Glu Ile
1775                1780                1785

Arg Lys Ser Thr Ser Asn Asn Leu Gln Asn Gln Asn Leu Arg Trp
    1790            1795            1800

Lys Met Thr Phe Asn Gly Ser Cys Ser Ser Val Cys Thr Trp Lys
1805                1810            1815

Ser Lys Asn Leu Lys Gly Ile Phe Gln Phe Arg Val Val Ala Ala
    1820            1825            1830

Asn Asn Leu Gly Phe Gly Glu Tyr Ser Gly Ile Ser Glu Asn Ile
    1835            1840            1845

Ile Leu Val Gly Asp Asp Phe Trp Ile Pro Glu Thr Ser Phe Ile
1850                1855            1860

Leu Thr Ile Ile Val Gly Ile Phe Leu Val Val Thr Ile Pro Leu
1865                1870            1875

Thr Phe Val Trp His Arg Arg Leu Lys Asn Gln Lys Ser Ala Lys
1880                1885            1890

Glu Gly Val Thr Val Leu Ile Asn Glu Asp Lys Glu Leu Ala Glu
1895                1900            1905

Leu Arg Gly Leu Ala Ala Gly Val Gly Leu Ala Asn Ala Cys Tyr
    1910            1915            1920

Ala Ile His Thr Leu Pro Thr Gln Glu Glu Ile Glu Asn Leu Pro
1925                1930            1935

Ala Phe Pro Arg Glu Lys Leu Thr Leu Arg Leu Leu Leu Gly Ser
1940                1945            1950

Gly Ala Phe Gly Glu Val Tyr Glu Gly Thr Ala Val Asp Ile Leu
1955                1960            1965

Gly Val Gly Ser Gly Glu Ile Lys Val Ala Val Lys Thr Leu Lys
    1970            1975            1980

Lys Gly Ser Thr Asp Gln Glu Lys Ile Glu Phe Leu Lys Glu Ala
1985                1990            1995

His Leu Met Ser Lys Phe Asn His Pro Asn Ile Leu Lys Gln Leu
2000                2005            2010

Gly Val Cys Leu Leu Asn Glu Pro Gln Tyr Ile Ile Leu Glu Leu
2015                2020            2025

Met Glu Gly Gly Asp Leu Leu Thr Tyr Leu Arg Lys Ala Arg Met
2030                2035            2040

Ala Thr Phe Tyr Gly Pro Leu Leu Thr Leu Val Asp Leu Val Asp
2045                2050            2055

Leu Cys Val Asp Ile Ser Lys Gly Cys Val Tyr Leu Glu Arg Met
2060                2065            2070

His Phe Ile His Arg Asp Leu Ala Ala Arg Asn Cys Leu Val Ser
2075                2080            2085

Val Lys Asp Tyr Thr Ser Pro Arg Ile Val Lys Ile Gly Asp Phe
2090                2095            2100

Gly Leu Ala Arg Asp Ile Tyr Lys Asn Asp Tyr Tyr Arg Lys Arg
    2105            2110            2115

Gly Glu Gly Leu Leu Pro Val Arg Trp Met Ala Pro Glu Ser Leu
    2120            2125            2130

Met Asp Gly Ile Phe Thr Thr Gln Ser Asp Val Trp Ser Phe Gly
2135                2140            2145

Ile Leu Ile Trp Glu Ile Leu Thr Leu Gly His Gln Pro Tyr Pro
2150                2155            2160

Ala His Ser Asn Leu Asp Val Leu Asn Tyr Val Gln Thr Gly Gly
2165                2170            2175

| | | | | | | | | | |
|---|---|---|---|---|---|---|---|---|---|
|Arg|Leu|Glu|Pro|Pro|Arg|Asn|Cys|Pro|Asp|Asp|Leu|Trp|Asn|Leu|
| |2180| | | |2185| | | |2190| | | | | |

Arg Leu Glu Pro Pro Arg Asn Cys Pro Asp Asp Leu Trp Asn Leu
    2180                2185                2190

Met Thr Gln Cys Trp Ala Gln Glu Pro Asp Gln Arg Pro Thr Phe
    2195                2200                2205

His Arg Ile Gln Asn Gln Leu Gln Leu Phe Arg Asn Phe Phe Leu
    2210                2215                2220

Asn Ser Ile Tyr Gln Cys Arg Asp Glu Ala Asn Asn Ser Gly Val
    2225                2230                2235

Ile Asn Glu Ser Phe Glu Gly Glu Asp Gly Asp Val Ile Cys Leu
    2240                2245                2250

Asn Ser Asp Asp Ile Met Pro Val Val Leu Met Glu Thr Lys Asn
    2255                2260                2265

Arg Glu Gly Leu Asn Tyr Met Val Leu Ala Thr Glu Cys Gly Gln
    2270                2275                2280

Gly Glu Glu Lys Ser Glu Gly Pro Leu Gly Ser Gln Glu Ser Glu
    2285                2290                2295

Ser Cys Gly Leu Arg Lys Glu Glu Lys Glu Pro His Ala Asp Lys
    2300                2305                2310

Asp Phe Cys Gln Glu Lys Gln Val Ala Tyr Cys Pro Ser Gly Lys
    2315                2320                2325

Pro Glu Gly Leu Asn Tyr Ala Cys Leu Thr His Ser Gly Tyr Gly
    2330                2335                2340

Asp Gly Ser Asp
    2345

<210> SEQ ID NO 8
<211> LENGTH: 7368
<212> TYPE: DNA
<213> ORGANISM: Homo sapiens

<400> SEQUENCE: 8

```
caagctttca agcattcaaa ggtctaaatg aaaaaggcta agtattattt caaaaggcaa      60
gtatatccta atatagcaaa acaaacaaag caaaatccat cagctactcc tccaattgaa     120
gtgatgaagc ccaaataatt catatagcaa aatggagaaa attagaccgg ccatctaaaa     180
atctgccatt ggtgaagtga tgaagaacat ttactgtctt attccgaagc ttgtcaattt     240
tgcaactctt ggctgcctat ggatttctgt ggtgcagtgt acagttttaa atagctgcct     300
aaagtcgtgt gtaactaatc tgggccagca gcttgacctt ggcacaccac ataatctgag     360
tgaaccgtgt atccaaggat gtcacttttg aactctgta gatcagaaaa actgtgcttt      420
aaagtgtcgg gagtcgtgtg aggttggctg tagcagcgcg gaaggtgcat atgaagagga     480
agtactggaa aatgcagacc taccaactgc tcccttttgct tcttccattg aagccacaa     540
tatgacatta cgatggaaat ctgcaaactt ctctggagta aaatacatca ttcagtggaa     600
atatgcacaa cttctgggaa gctggactta tactaagact gtgtccagac cgtcctatgt     660
ggtcaagccc ctgcacccct tcactgagta cattttccga gtggtttgga tcttcacagc     720
gcagctgcag ctctactccc ctccaagtcc cagttacagg actcatcctc atggagttcc     780
tgaaactgca cctttgatta ggaatattga gagctcaagt cccgacactg tggaagtcag     840
ctgggatcca cctcaattcc caggtggacc tattttgggt tataacttaa ggctgatcag     900
caaaaatcaa aaattagatg cagggacaca gagaaccagt ttccagttttt actccacttt     960
accaaatact atctacaggt tttctattgc agcagtaaat gaagttggtg agggtccaga   1020
agcagaatct agtattacca cttcatcttc agcagttcaa caagaggaac agtggctctt   1080
```

```
tttatccaga aaaacttctc taagaaagag atctttaaaa catttagtag atgaagcaca    1140
ttgccttcgg ttggatgcta tataccataa tattacagga atatctgttg atgtccacca    1200
gcaaattgtt tatttctctg aaggaactct catatgggcg aagaaggctg ccaacatgtc    1260
tgatgtatct gacctgagaa ttttttacag aggttcagga ttaatttctt ctatctccat    1320
agattggctt tatcaaagaa tgtatttcat catggatgaa ctggtatgtg tctgtgattt    1380
agagaactgc tcaaacatcg aggaaattac tccaccctct attagtgcac ctcaaaaaat    1440
tgtggctgat tcatacaatg gtatgtctt ttacctcctg agagatggca tttatagagc     1500
agaccttcct gtaccatctg gccggtgtgc agaagctgtg cgtattgtgg agagttgcac    1560
gttaaaggac tttgcaatca agccacaagc aagcgaatc atttacttca atgacactgc     1620
ccaagtcttc atgtcaacat ttctggatgg ctctgcttcc catctcatcc tacctcgcat    1680
cccctttgct gatgtgaaaa gttttgcttg tgaaaacaat gactttcttg tcacagatgg    1740
caaggtcatt ttccaacagg atgctttgtc ttttaatgaa ttcatcgtgg atgtgacct     1800
gagtcacata aagaatttg gtttggtaa cttggtcatc tttggctcat cctcccagct      1860
gcaccctctg ccaggccgcc cgcaggagct ttcggtgctg tttggctctc accaggctct    1920
tgttcaatgg aagcctcctg cccttgccat aggagccaat gtcatcctga tcagtgatat    1980
tattgaactc tttgaattag gcccttctgc ctggcagaac tggacctatg aggtgaaagt    2040
atccacccaa gaccctcctg aagtcactca tattttcttg aacataagtg gaaccatgct    2100
gaatgtacct gagctgcaga gtgctatgaa atacaaggtt tctgtgagag caagttctcc    2160
aaagaggcca ggcccctggt cagagccctc agtgggtact accctggtgc agctagtga    2220
accaccattt atcatggctg tgaaagaaga tgggctttgg agtaaaccat taaatagctt    2280
tggcccagga gagttcttat cctctgatat aggaaatgtg tcagacatgg attggtataa    2340
caacagcctc tactacagtg acacgaaagg cgacgttttt gtgtggctgc tgaatgggac    2400
ggatatctca gagaattatc acctacccag cattgcagga gcagggctt tagcttttga     2460
gtggctgggt cactttctct actgggctgg aaagacatat gtgatacaaa ggcagtctgt    2520
gttgacggga cacacagaca ttgttaccca cgtgaagcta ttggtgaatg acatggtggt    2580
ggattcagtt ggtggatatc tctactggac cacactctat tcagtggaaa gcaccagact    2640
aaatggggaa agttcccttg tactacagac acagccttgg ttttctggga aaaggtaat    2700
tgctctaact ttagacctca gtgatgggct cctgtattgg ttggttcaag acagtcaatg    2760
tattcacctg tacacagctg ttcttcgggg acagagcact ggggatacca ccatcacaga    2820
atttgcagcc tggagtactt ctgaaatttc ccagaatgca ctgatgtact atagtggtcg    2880
gctgttctgg atcaatggct ttaggattat cacaactcaa gaaataggtc agaaaaccag    2940
tgtctctgtt ttggaaccag ccagatttaa tcagttcaca attattcaga catcccttaa    3000
gcccctgcca gggaactttt cctttacccc taaggttatt ccagattctg ttcaagagtc    3060
ttcatttagg attgaaggaa atgcttcaag ttttcaaatc ctgtggaatg gtcccccgc     3120
ggtagactgg ggtgtagttt tctacagtgt agaatttagt gctcattcta agttcttggc    3180
tagtgaacaa cactctttac ctgtatttac tgtggaagga ctggaacctt atgccttatt    3240
taatctttct gtcactcctt ataccctactg gggaaagggc cccaaaacat ctctgtcact    3300
tcgagcacct gaaacagttc catcagcacc agagaacccc agaatattta tattaccaag    3360
tggaaaatgt gcaacaagaa atgaagttgt ggtggaattt aggtgaaaca aacctaagca    3420
tgaaaatggg gtgttaacaa aatttgaaat tttctacaat atatccaatc aaagtattac    3480
```

-continued

```
aaacaaaaca tgtgaagact ggattgctgt caatgtcact ccctcagtga tgtcttttca    3540
acttgaaggc atgagtccca gatgctttat tgccttccag gttagggcct ttacatctaa    3600
ggggccagga ccatatgctg acgttgtaaa gtctacaaca tcagaaatca acccatttcc    3660
tcacctcata actcttcttg gtaacaagat agtttttta gatatggatc aaaatcaagt    3720
tgtgtggacg ttttcagcag aaagagttat cagtgccgtt tgctacacag ctgataatga    3780
gatgggatat tatgctgaag gggactcact ctttcttctg cacttgcaca atcgctctag    3840
ctctgagctt ttccaagatt cactggtttt tgatatcaca gttattacaa ttgactggat    3900
ttcaaggcac ctctactttg cactgaaaga atcacaaaat ggaatgcaag tatttgatgt    3960
tgatcttgaa cacaaggtga aatatcccag agaggtgaag attcacaata ggaattcaac    4020
aataatttct ttttctgtat atcctctttt aagtcgcttg tattggacag aagtttccaa    4080
ttttggctac cagatgttct actacagtat tatcagtcac accttgcacc gaattctgca    4140
acccacagct acaaaccaac aaaacaaaag gaatcaatgt tcttgtaatg tgactgaatt    4200
tgagttaagt ggagcaatgg ctattgatac ctctaaccta gagaaaccat tgatatactt    4260
tgccaaagca caagagatct gggcaatgga tctggaaggc tgtcagtgtt ggagagttat    4320
cacagtacct gctatgctcg caggaaaaac ccttgttagc ttaactgtgg atggagatct    4380
tatatactgg atcatcacag caaggacaga cacacagatt tatcaggcaa agaaaggaaa    4440
tggggccatc gtttcccagg tgaaggccct aaggagtagg catatcttgg cttacagttc    4500
agttatgcag cctttccag ataaagcgtt tctgtctcta gcttcagaca ctgtggaacc    4560
aactatactt aatgccacta acactagcct cacaatcaga ttacctctgg ccaagacaaa    4620
cctcacatgg tatggcatca ccagccctac tccaacatac ctggtttatt atgcagaagt    4680
taatgacagg aaaaacagct ctgacttgaa atatagaatt ctggaatttc aggacagtat    4740
agctcttatt gaagatttac aaccattttc aacatacatg atacagatag ctgtaaaaaa    4800
ttattattca gatcctttgg aacatttacc accaggaaaa gagatttggg gaaaaactaa    4860
aaatggagta ccagaggcag tgcagctcat taatacaact gtgcggtcag acaccagcct    4920
cattatatct tggagagaat ctcacaagcc aaatggacct aaagaatcag tccgttatca    4980
gttggcaatc tcacacctgg ccctaattcc tgaaactcct ctaagacaaa gtgaatttcc    5040
aaatggaagg ctcactctcc ttgttactag actgtctggt ggaaatattt atgtgttaaa    5100
ggttcttgcc tgccactctg aggaaatgtg gtgtacagag agtcatcctg tcactgtgga    5160
aatgtttaac acaccagaga aaccttattc cttggttcca gagaacacta gtttgcaatt    5220
taattggaag gctccattga atgttaacct catcagattt tgggttgagc tacagaagtg    5280
gaaatacaat gagttttacc atgttaaaac ttcatgcagc caaggtcctg cttatgtctg    5340
taatatcaca aatctacaac cttatacttc atataatgtc agagtagtgg tggtttataa    5400
gacgggagaa aatagcacct cacttccaga aagctttaag acaaaagctg gagtcccaaa    5460
taaaccaggc attcccaaat tactagaagg gagtaaaaat tcaatacagt gggagaaagc    5520
tgaagataat ggatgtagaa ttacatacta tatccttgag ataagaaaga gcacttcaaa    5580
taatttacag aaccagaatt taaggtggaa gatgacattt aatggatcct gcagtagtgt    5640
ttgcacatgg aagtccaaaa acctgaaagg aatatttcag ttcagagtag tagctgcaaa    5700
taatctaggg tttggtgaat atagtggaat cagtgagaat attatattag ttggagatga    5760
tttttggata ccagaaacaa gtttcatact tactattata gttggaatat ttctggttgt    5820
tacaatccca ctgacctttg tctggcatag aagattaaag aatcaaaaaa gtgccaagga    5880
```

```
aggggtgaca gtgcttataa acgaagacaa agagttggct gagctgcgag gtctggcagc    5940
cggagtaggc ctggctaatg cctgctatgc aatacatact cttccaaccc aagaggagat    6000
tgaaaatctt cctgccttcc ctcgggaaaa actgactctg cgtctcttgc tgggaagtgg    6060
agcctttgga gaagtgtatg aaggaacagc agtggacatc ttaggagttg aagtggaga    6120 aatcaaagta gcagtgaaga ctttgaagaa gggttccaca gaccaggaga agattgaatt    6180
cctgaaggag gcacatctga tgagcaaatt taatcatccc aacattctga agcagcttgg    6240
agtttgtctg ctgaatgaac cccaatacat tatcctggaa ctgatggagg gaggagacct    6300
tcttacttat ttgcgtaaag cccggatggc aacgttttat ggtcctttac tcaccttggt    6360
tgaccttgta gacctgtgtg tagatatttc aaaaggctgt gtctacttgg aacggatgca    6420
tttcattcac agggatctgg cagctagaaa ttgccttgtt tccgtgaaag actataccag    6480
tccacggata gtgaagattg agactttgg actcgccaga gacatctata aaaatgatta    6540
ctatagaaag agaggggaag gcctgctccc agttcgtgg atggctccag aaagtttgat    6600
ggatggaatc ttcactactc aatctgatgt atggtctttt ggaattctga tttgggagat    6660
tttaactctt ggtcatcagc cttatccagc tcattccaac cttgatgtgt aaactatgt    6720 gcaaacagga gggagactgg agccaccaag aaattgtcct gatgatctgt ggaatttaat    6780
gacccagtgc tgggctcaag aacccgacca agacctact tttcatagaa ttcaggacca    6840
acttcagtta ttcagaaatt ttttcttaaa tagcatttat aagtccagag atgaagcaaa    6900
caacagtgga gtcataaatg aaagctttga aggtgaagat ggcgatgtga tttgtttgaa    6960
ttcagatgac attatgccag ttgctttaat ggaaacgaag aaccgagaag ggttaaacta    7020
tatggtactt gctacagaat gtggccaagg tgaagaaaag tctgagggtc ctctaggctc    7080
ccaggaatct gaatcttgtg gtctgaggaa agaagagaag gaaccacatg cagacaaaga    7140
tttctgccaa gaaaaacaag tggcttactg cccttctggc aagcctgaag gcctgaacta    7200
tgcctgtctc actcacagtg gatatggaga tgggtctgat taatagcgtt gtttgggaaa    7260
tagagagttg agataaacac tctcattcag tagttactga aagaaaactc tgctagaatg    7320
ataaatgtca tggtggtcta taactccaaa taaacaatgc aacgttcc                7368

<210> SEQ ID NO 9
<211> LENGTH: 20
<212> TYPE: PRT
<213> ORGANISM: Homo sapiens

<400> SEQUENCE: 9

Ile Leu Ser Ser Ala Phe Gln Leu Val Gly Ala Gly Val Pro Asn Lys
1               5                   10                  15

Pro Gly Ile Pro
            20

<210> SEQ ID NO 10
<211> LENGTH: 60
<212> TYPE: DNA
<213> ORGANISM: Homo sapiens

<400> SEQUENCE: 10
attcttagta gcgccttcca gctggttgga gctggagtcc caaataaacc aggcattccc    60

<210> SEQ ID NO 11
<211> LENGTH: 20
<212> TYPE: PRT
<213> ORGANISM: Homo sapiens
```

<400> SEQUENCE: 11

Ile Leu Ser Ser Ala Phe Gln Leu Val Gly Asp Asp Phe Trp Ile Pro
1               5                   10                  15

Glu Thr Ser Phe
            20

<210> SEQ ID NO 12
<211> LENGTH: 60
<212> TYPE: DNA
<213> ORGANISM: Homo sapiens

<400> SEQUENCE: 12
attcttagta gcgccttcca gctggttgga gatgattttt ggataccaga aacaagtttc       60

<210> SEQ ID NO 13
<211> LENGTH: 24
<212> TYPE: DNA
<213> ORGANISM: Artificial
<220> FEATURE:
<223> OTHER INFORMATION: Primer sequence

<400> SEQUENCE: 13
acccttctcg gttcttcgtt tcca                                             24

<210> SEQ ID NO 14
<211> LENGTH: 24
<212> TYPE: DNA
<213> ORGANISM: Artificial
<220> FEATURE:
<223> OTHER INFORMATION: Primer sequence

<400> SEQUENCE: 14
gcagctcagc caactctttg tctt                                             24

<210> SEQ ID NO 15
<211> LENGTH: 24
<212> TYPE: DNA
<213> ORGANISM: Artificial
<220> FEATURE:
<223> OTHER INFORMATION: Primer sequence

<400> SEQUENCE: 15
tgccagacaa aggtcagtgg gatt                                             24

<210> SEQ ID NO 16
<211> LENGTH: 21
<212> TYPE: DNA
<213> ORGANISM: Artificial
<220> FEATURE:
<223> OTHER INFORMATION: Primer sequence

<400> SEQUENCE: 16
tccatcccag cacctgcgga g                                                21

<210> SEQ ID NO 17
<211> LENGTH: 27
<212> TYPE: DNA
<213> ORGANISM: Artificial
<220> FEATURE:
<223> OTHER INFORMATION: Primer sequence

<400> SEQUENCE: 17
ctcaactctc tatttcccaa acaacgc                                          27

```
<210> SEQ ID NO 18
<211> LENGTH: 22
<212> TYPE: DNA
<213> ORGANISM: Artificial
<220> FEATURE:
<223> OTHER INFORMATION: Primer sequence

<400> SEQUENCE: 18
catggctccc tggcctgaat tg                                               22

<210> SEQ ID NO 19
<211> LENGTH: 26
<212> TYPE: DNA
<213> ORGANISM: Artificial
<220> FEATURE:
<223> OTHER INFORMATION: Primer sequence

<400> SEQUENCE: 19
caacgctatt aatcagaccc atctcc                                           26

<210> SEQ ID NO 20
<211> LENGTH: 32
<212> TYPE: DNA
<213> ORGANISM: Artificial
<220> FEATURE:
<223> OTHER INFORMATION: Primer sequence

<400> SEQUENCE: 20
gaagatctct gaccatggct ccctggcctg aa                                    32

<210> SEQ ID NO 21
<211> LENGTH: 32
<212> TYPE: PRT
<213> ORGANISM: Artificial
<220> FEATURE:
<223> OTHER INFORMATION: Primer sequence

<400> SEQUENCE: 21

Gly Ala Ala Gly Ala Thr Cys Thr Ala Cys Gly Cys Thr Ala Thr Thr
1               5                   10                  15

Ala Ala Thr Cys Ala Gly Ala Cys Cys Cys Ala Thr Cys Thr Cys Cys
            20                  25                  30
```